(12) United States Patent
Knopf et al.

(10) Patent No.: US 8,629,109 B2
(45) Date of Patent: *Jan. 14, 2014

(54) METHOD FOR PROMOTING BONE GROWTH USING ACTIVIN-ACTRIIA ANTAGONISTS

(75) Inventors: John Knopf, Carlisle, MA (US); Jasbir Seehra, Lexington, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 71 days.

This patent is subject to a terminal disclaimer.

(21) Appl. No.: 13/176,718

(22) Filed: Jul. 5, 2011

(65) Prior Publication Data

US 2012/0058115 A1    Mar. 8, 2012

Related U.S. Application Data

(63) Continuation of application No. 12/284,862, filed on Sep. 24, 2008, now Pat. No. 8,067,360, which is a continuation of application No. 11/603,485, filed on Nov. 22, 2006, now Pat. No. 7,612,041.

(60) Provisional application No. 60/739,462, filed on Nov. 23, 2005, provisional application No. 60/783,322, filed on Mar. 17, 2006, provisional application No. 60/844,855, filed on Sep. 15, 2006.

(51) Int. Cl.
*A61K 38/00* (2006.01)
*C07K 14/51* (2006.01)

(52) U.S. Cl.
USPC ........... 514/16.7; 530/350; 530/402; 530/412

(58) Field of Classification Search
None
See application file for complete search history.

(56) References Cited

U.S. PATENT DOCUMENTS

| | | | |
|---|---|---|---|
| 4,973,577 A | 11/1990 | Vale, Jr. et al. |
| 5,118,667 A | 6/1992 | Adams et al. |
| 5,658,876 A | 8/1997 | Crowley et al. |
| 5,760,010 A | 6/1998 | Klein |
| 5,808,007 A | 9/1998 | Lee et al. |
| 5,824,637 A | 10/1998 | Crowley et al. |
| 5,847,078 A | 12/1998 | Eto et al. |
| 5,863,738 A * | 1/1999 | Dijke et al. ............... 435/7.1 |
| 5,885,794 A | 3/1999 | Mathews et al. |
| 6,004,780 A | 12/1999 | Soppet et al. |
| 6,093,547 A | 7/2000 | Jin et al. |
| 6,132,988 A | 10/2000 | Sugino et al. |
| 6,162,896 A | 12/2000 | Mathews et al. |
| 6,440,930 B1 | 8/2002 | Rinella, Jr. |
| 6,451,334 B2 | 9/2002 | Perrine |
| 6,537,966 B1 | 3/2003 | Duan et al. |
| 6,548,634 B1 | 4/2003 | Ballinger et al. |
| 6,599,876 B2 | 7/2003 | Kojima |
| 6,605,699 B1 | 8/2003 | Ni et al. |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Dunham et al. |
| 7,560,441 B2 | 7/2009 | Wolfman et al. |
| 7,612,041 B2 | 11/2009 | Knopf et al. |
| 7,988,973 B2 | 8/2011 | Sherman |
| 8,007,809 B2 | 8/2011 | Sherman |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 2001/0039036 A1 | 11/2001 | Mathews et al. |
| 2003/0083251 A1 | 5/2003 | Westenfelder |
| 2003/0144203 A1 | 7/2003 | Bowen |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0210657 A1 | 9/2006 | Chou |
| 2007/0048830 A1 | 3/2007 | Gilbert et al. |
| 2007/0149455 A1 | 6/2007 | Wolfman et al. |

(Continued)

FOREIGN PATENT DOCUMENTS

| EP | 1 174 149 | 1/2002 |
|---|---|---|
| EP | 1 362 062 B1 | 11/2003 |

(Continued)

OTHER PUBLICATIONS

Rosenzweig et al., Proc. Natl. Acad. Sci. 92: 7632-7636,1995.*
"Recombinant Human Activin RIIA/Fc Chimera," R&D Systems 340-R2. (2003).
"Recombinant Human Activin RIIB/Fc Chimera," R&D Systems 339-RB/CF (2003).
Acceleron Pharma Presents Positive Phase 1 Results Demonstrating ACE-011 Increases Markers of Bone Formation. pages 1-2 (2007) www.acceleronpharma.com/content/news/press-releases/detail.jsp/q/news-id/47>.
Akel, S., et al,, "Neutralization of Autocrine Transforming Growth Factor -β," Stem Cells, 21:557-567 (2003).
Akpan, I., et al., "The effects of a soluble activin type IIB receptor on obesity and insulin sensitivity," International Journal of Obesity, 33(11):1265-1273 (2009).

(Continued)

*Primary Examiner* — Gyan Chandra

(74) *Attorney, Agent, or Firm* — Ropes & Gray LLP

(57) ABSTRACT

In certain aspects, the present invention provides compositions and methods for promoting bone growth and increasing bone density.

129 Claims, 24 Drawing Sheets
(6 of 24 Drawing Sheet(s) Filed in Color)

(56) References Cited

U.S. PATENT DOCUMENTS

| | | |
|---|---|---|
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0183624 A1 | 7/2010 | Seehra et al. |
| 2010/0272734 A1 | 10/2010 | Berger et al. |
| 2010/0316644 A1 | 12/2010 | Seehra et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2012/0015877 A1 | 1/2012 | Seehra et al. |

FOREIGN PATENT DOCUMENTS

| | | |
|---|---|---|
| WO | WO 92/04913 A1 | 4/1992 |
| WO | WO-92/20793 | 11/1992 |
| WO | WO 94/15965 A1 | 7/1994 |
| WO | WO-95/10611 | 4/1995 |
| WO | WO 95/29685 A1 | 11/1995 |
| WO | WO 97/23613 A2 | 7/1997 |
| WO | WO-99/06559 | 2/1999 |
| WO | WO 00/18932 A2 | 4/2000 |
| WO | WO-00/43781 | 7/2000 |
| WO | WO-02/10214 | 2/2002 |
| WO | WO-02/43759 | 6/2002 |
| WO | WO-02/085306 | 10/2002 |
| WO | WO 02/094852 A2 | 11/2002 |
| WO | WO-03/006057 | 1/2003 |
| WO | WO 03/053219 A2 | 7/2003 |
| WO | WO-03/072808 A1 | 9/2003 |
| WO | WO-2004/039948 A2 | 5/2004 |
| WO | WO-2004/108157 | 12/2004 |
| WO | WO 2005/003158 A2 | 1/2005 |
| WO | WO-2005/009460 A2 | 2/2005 |
| WO | WO 2005/014650 A2 | 2/2005 |
| WO | WO-2005/028517 | 3/2005 |
| WO | WO 2005/070967 A2 | 8/2005 |
| WO | WO-2005/094871 A2 | 10/2005 |
| WO | WO-2005/097825 A2 | 10/2005 |
| WO | WO-2006/002387 A2 | 1/2006 |
| WO | WO-2006/012627 A2 | 2/2006 |
| WO | WO 2006/020884 A2 | 2/2006 |
| WO | WO-2006/039400 A2 | 4/2006 |
| WO | WO-2006/068468 A1 | 6/2006 |
| WO | WO-2006/083183 | 8/2006 |
| WO | WO-2006/088972 A2 | 8/2006 |
| WO | WO 2007/038703 A2 | 4/2007 |
| WO | WO-2007/053775 | 5/2007 |
| WO | WO-2007/062188 A2 | 5/2007 |
| WO | WO-2007/067616 | 6/2007 |
| WO | WO 2007/076127 A2 | 7/2007 |
| WO | WO-2008/031061 | 3/2008 |
| WO | WO-2008/060139 | 5/2008 |
| WO | WO 2008/072723 A1 | 6/2008 |
| WO | WO-2008/076437 A2 | 6/2008 |
| WO | WO 2008/094708 A2 | 8/2008 |
| WO | WO-2008/097541 A2 | 8/2008 |
| WO | WO-2008/100384 A2 | 8/2008 |
| WO | WO-2008/109167 | 9/2008 |
| WO | WO 2008/151078 A1 | 12/2008 |
| WO | WO 2009/009059 A1 | 1/2009 |
| WO | WO 2009/019504 A1 | 2/2009 |
| WO | WO 2009/019505 A2 | 2/2009 |
| WO | WO 2009/025651 A1 | 2/2009 |
| WO | WO 2009/137075 A1 | 11/2009 |
| WO | WO 2009/137613 A2 | 11/2009 |
| WO | WO 2009/158015 A2 | 12/2009 |
| WO | WO 2009/158025 A2 | 12/2009 |
| WO | WO 2010/019261 A1 | 2/2010 |
| WO | WO 2010/083034 A1 | 7/2010 |
| WO | WO 2010/144452 A1 | 12/2010 |
| WO | WO 2010/151426 A1 | 12/2010 |

OTHER PUBLICATIONS

Bowie, J.U., et al., "Deciphering the Message in Protein Sequences: Tolerance to Amino Acid Substitutions," Science, 347:1306-1310 (1990).

Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).

Burdette et al., "Activin A mediates growth inhibition and cell cycle arest through Smads in human breast cancer cells," Cancer Research, 65(17):7968-7975 (2005).

Burgess, W.H., et al., "Possible Dissociation of the Heparin-binding and Mitogenic Activities of Herapin-binding (Acidic Fibroblast) Growth Factor-1 from Its Receptor-binding Activities by Site-directed Mutagenesis of a Single Lysine Residue," J. Cell Biol 111:2129-2138 (1990).

Centrella et al., "Activin-A Binding and Biochemical Effects in Osteoblast-Enriched Cultures from Fetal-Rat Parietal Bone," Molecular and Cellular Biology, 11(1):250-58 (1991).

Chen, Y.G., et al. "Regulation of Cell Proliferation, Apoptosis, and Carcinogenesis by Activin," Exp. Biol. Med., 227(2):75-87 (2002).

Cirillo et al., Hematocrit, blood pressure, and hypertension. The Gubbio Population Study. Hypertension 20(3): 319-326 (1992).

Coerver, K.A., et al., "Activin Signaling through Activin Receptor Type II Causes the Cachexia-Like Symptoms in Inhibin-Deficient Mice," Molecular Endocrinology, 10(5):534-543 (1996).

Colman, P.M., "Effects of amino acid sequence changes on antibody-antigen interactions," Res. Immunology, 33-36 (1994).

Daluiski et al., "Bone Morphogenetic Protein-3 is a Negative Regulator of Bone Density," Nature Genetics 27:84-88 (2001).

Donaldson et al., "Activin and Inhibin Binding to the Soluble Extracellular Domain of Activin Receptor II," Endocrinology 140(4):1760-1766 (1999).

Donaldson et al., "Molecular Cloning and Binding Properties of the Human Type II Activin Receptor," Biochemical and Biophysical Research Corporation, 184(1):310-316 (1992).

Elisabetta del Re et al., "Reconstitution and Analysis of Soluble Inhibin and Activin Receptor Complexes in a Cell-free System," The Journal of Biological Chemistry, 279(51):53126-53135 (2004).

Fafioffe, A., et al., "Activin and inhibin receptor gene expression in the ewe pituitary throughout the oestrous cycle," Journal of Endocrinology, 182:55-68 (2004).

Frigon, N.L., et al, "Regulation of Globin Gene Expression in Human K562 Cells by Recombinant Activin A," Blood, 79(3):765-772 (1992).

Fuller et al., "Activin A Is an Essential Cofactor for Osteoclast Induction," Biochemical and Biophysical Research Communications 268:2-7 (2000).

Funaba et al., "Expression and Localization of Activin Receptors During Endochondral Bone Development," European Journal of Endocrinology, 144:63-71 (2001).

(56) References Cited

OTHER PUBLICATIONS

Gaddy-Kurten et al., "Inhibin Suppresses and Activin Stimulates Osteoblastogenesis and Osteoclastogenesis in Murine Bone Marrow Cultures," Endocrinology 143(1):74-83 (2002).
Gamer et al., "BMP-3 is a Novel Inhibitor of Both Activin and BMP-4 Signaling in Xenopus Embryos," Developmental Biology 285:156-168 (2005).
Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gonzalez-Cadavid, N.F., et al., "Organization of the human myostatin gene and expression in healthy men and HIV-infected men with muscle wasting," PNAS, 95:14938-14943 (1998).
Gray et al., "Identification of a Binding Site on the Type II Activin Receptor for Activin and Inhibin," The Journal of Biological Chemistry, 275(5):3206-3212 (2000).
Greenspan, N.S., et al., "Defining epitopes: It's not as easy as it seems," Nature Biotechnology, 17:936-937 (1999).
Greenwald, et al., "The BMP7/ActRll Extracellular Domain Complex Provides New Insights into the Cooperative Nature of Receptor Assembly," Molecular Cell, vol. 11, 6-5-617 (2003).
Gupta, V. et al., "Transforming Growth Factor-b Superfamily: Evaluation as Breast Cancer Biomarkers and Preventive Agents," Current Cancer Drug Targets, 4:165-182 (2004).
Gura, T., "Cancer Models: Systems for Identifying New Drugs Are Often Faulty," Science, 278(5340):1041-1042 (1997).
Hamrick et al., "Bone Mineral Content and Density in the Humerus of Adult Myostatin-Deficient Mice," Calcified Tissue International 71:63-68 (2002).
Hamrick, "Increased Bone Mineral Density in the Femora of GDF8 Knockout Mice," The Anatomical Record Part A 272A:388-391 (2003).
Hamrick, M.W., et al., "Femoral Morphology and Cross-sectional Geometry of Adult Myostatin-deficient Mice," Bone, 27(3):343-349 (2000).
Harrison, et al., "Antagonists of Activin Signaling: Mechanisms and Potential Biological Applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry 267(7):4999-5004 (1992).
Hemmati-Brivanlou, A., et al., "A truncated activin receptor inhibits mesoderm induction and formation of axial structures in Xenopus embryos," Nature, 359:609-614 (1992).
Herbert, J.H., et al., The Dictionary of Immunology, Fourth Edition, pp. 58-59 (1995).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Ikenoue et al., "Inhibitory Effects of Activin-A on Osteoblast Differentiatin During Cultures of Fetal Rat Calvarial Cells," Journal of Cellular Biochemistry 75:206-214 (1999).
Journal of Bone and Mineral Research 2006 Abstracts, 21(1):s1-s530 (2006).
Kaiser, J., "First Pass at Cancer Genome Reveals Complex Landscape," Science, 313:1370 (2006).
Kaspar, B.K., et al., "Retrograde Viral Delivery of IGF-1 Prolongs Survival in a Mouse ALS Model," Science, 301:839-842 (2003).
Kim, et al., Type IIa IgG-Fc Fusion Protein, Increases Hemoglobin and Hematocrit Levels in Postmenopausal Healthy Women. Blood, 112(11):1316 (2008).
Knight, "Roles of Inhibins, Activins, and Follistatin in the Female Reproductive System," Frontiers in Neuroendocrinology 17:476-509 (1996).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF—Family in Osteoclastogenesis Induced by RANKL," Cellular Signalling 14:31-36 (2002).
Krneta, J., et al., "Dissociation of Angiogenesis and Tumorigenesis in Follistatin- and Activin-Expressing Tumors," Cancer Research, 66(11):5686-5695 (2006).
Krystal et al., "Transforming Growth Factor $\beta1$ Is an Inducer of Erythroid Differentiation," J. Exp. Med., 180:851-860 (1994).
Kubanek, B., "Introduction: The Role of the Microenvironment and Cytokines on the Modulation of Erythropoiesis," Annals New York Academy of Sciences, pp. 257-258 (1994).
Lazar, E., et al., "Transforming Growth Factor $\alpha$: Mutation of Aspartic Acid 47 and Leucine 48 Results in Different Biological Activities," Molecular and Cellular Biology, 8(3):1247-1252 (1988).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS 98(16):9306-9311 (2001).
Leto et al., "Activin A Circulating Levels in Patients with Bone Metastasis from Breast or Prostate Cancer," Clin Exp Metastasis 23(2):117-122 (2006).
Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Ludlow, H., et al., "Development of a new antibody to the human inhibin/activin $\beta B$ subunit and its application to improved inhibin B ELISAs," J. Immunol. Methods, 329:102-111 (2008).
Maguer-Satta, V., et al, "Regulation of human erythropoiesis by activin A, BMP2, and BMP4, members of the TGF$\beta$ family," Experimental Cell Research, 282:110-120 (2003).
Matzuk et al., "Different phenotypes for mice deficient in either activins or activin receptor type II," Nature, 374:356-360 (1995).
McNally, E.M., "Powerful Genes—Myostatin Regulation of Human Muscle Mass," N. Engl. J. Med., 350(26):2642-2644 (2004).
McPherron, A.C., et al., "Regulation of Skeletal Muscle Mass in Mice by a Bew TGF-b Superfamily Member," Nature, 387:83-90 (1997).
McPherson, S.J., et al., "Growth inhibitory response to activin A and B by human prostate tumour cell lines LNCaP and DU1465", Journal of Endocrinology, 154:535-545 (1997).
Mickle, Ph.D., John, et al, "Genotype-Phenotype Relationships in Cystic Fibrosis," Medical Clinics of North America, vol. 84, No. 3, pp. 597-607, 2000.
Merck Manuals Online Medical Library (online). Anemia of Chronic Disease. <http://web.archive.org/web/20080610070226/http://www.merck.com/mmpe/sec11/ch130/ch130d.html> p. 1-2 and 6.(downloaded Jun. 10, 2008).
Meriggiola et al., "Follistatin Decreases Activin-Stimulated FSH Secretion with No Effect On GnRH-Stimulated FSH Secretion in Prepubertal Male Monkeys," Endocrinology 134(4):1967-1970 (1994).
Murase et al., "Possible Involvement of Protein Kinases and Smad2 Signaling Pathways on Osteoclast Differentiation Enhanced by Activin A," Journal of Cellular Physiology 188:236-242 (2001).
Nagamine et al., "Immunohistochemical Detection of Activin A, Follistatin, and Activin Receptors during Fracture Healing in the Rat," Journal of Orthopaedic Research 16:314-321 (1998).
Nakamura, K., et al, "Effect of Erythroid Differentiation Factor on Maintenance of Human Hematopoietic Cells in Co-cultures with

(56) References Cited

OTHER PUBLICATIONS

Allogenic Stromal Cells," Biochemical and Biophysical Research Communications, 194(3):1103-1110 (1993).
Ngo, J.T., et al., Computational Complexity, Protein Structure Prediction, and the Levinthal Paradox, The Protein Folding Problem and Tertiary Structure Prediction, Merz et al., eds., Birkhauser, Boston, pp. 492-495 (1994).
Ogawa et al., "Bovine Bone Activin Enhances Bone Morphogenetic Protein-Induced Ectopic Bone Formation," The Journal of Biological Chemistry 267(20):14233-14237 (1992).
Oh, S.P., et al., "Activin type IIa and IIb receptors mediate Gdf11 signaling in axial vertebral patterning," Genes & Development, 16:2749-2754 (2002).
Oue et al., "Effect of Local Injection of Activin A on Bone Formation in Newborn Rats," Bone 15(3):361-366 (1994).
Pearsall, R.S., et al., "A soluble activin Type IIA receptor induces bone formation and improves skeletal integrity", PNAS, 105(9):7082-7087 (2008).
Rebbapragada et al., "Myostatin Signals Through a Transforming Growth Fact -Like Signaling Pathway To Block Adipogenesis," Molecular and Cellular Biology 23(20):7230-7242 (2003).
Reis, F.M., et al., "Activin, Inhibin and the Human Breast," Molecular and Cellular Edocrinology, 225:77-82 (2004).
Risbridger, G.P, et al., "Activins and Inhibins in Endocrine and Other Tumors," Endocrine Reviews, 22(6):836-858 (2001).
Robinson, G.W., et al., "Inhibins and Activins Regulate Mammary Epithelial Cell Differentiation Through Mesenchymal-epithelial Interactions," Development, 124:2701-2708 (1997).
Ruzek et al., "Minimal Effects on Immune Parameters Following Chronic Anti-TGF-? Monoclonal Antibody Administration to Normal Mice," Immunopharmacology and Immunotoxicology 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone 27(1):91-96 (2000).
Sakai et al., "Involvement of Activin in the Regulation of Bone Metabolism," Molecular and Cellular Endocrinology 180:183-188 (2001).
Sakai et al., "Local Administration of Activin Promotes Fracture Healing in the Rat Fibula Fracture Model," Bone 25(2):191-196 (1999).
Sakai, et al., "Activin Release From Bone Coupled to Bone Resorption in Organ Culture of Neonatal Mouse Calvaria," Bone 26(3):235-240 (2000).
Sakai et al., "The Measurement of Activin/EDF in Mouse Serum: Evidence for Extragonadal Production," Biochemical and Biophysical Research Communications, 188(2):921-926 (1992).
Sakai, et al., "Osteogenic Activity of Activin in Young Normal Rats and Young Adult and Aged Rats after Ovarlectomy," Bone 23:(Suppl.) 467 (1998).
Satoh et al., Hemodynamic changes by recombinant erythropoietin therapy in hemodialyzed patients. Hypertension, 15(3): 262-266, 264, and table 1 (1990).
Schuelke, M., et al., "Myostatin Mutation Associated with Gross Muscle Hypertrophy in a Child," New England Journal of Medicine, 350(26):2682-2688 (2004).
Shao, L., et al., "Effect of Activin A on Globin Gene Expression in Purified Human Erythroid Progenitors," Blood, 79(3):773-781 (1992).
Shav-Tal, Y., et al., "The Role of Activin A in Regulation of Hemopoiesis," Stem Cells, 20:493-500 (2002).
Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shuto et al., "Osteoblasts Express Types I and II Activin Receptors During Early Intramembranous and Endochondral Bone Formation," Journal of Bone Mineral Research 12(3):403-411 (1997).
Song, J., et al., "The Type II Activin Receptors Are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S29-S75 (2007).
Sun et al., "FSH Directly Regulates Bone Mass," Cell 125:247-260 (2006).
The Official Journal of the European Calcified Tissue Society, 34th Europena Symposium on Calcified Tissues, May (2007).
Thompson et al., "Structures of an ActRIIB:Activin A Complex Reveal a Novel Binding Mode for TGF-beta Ligand:Receptor Interactions," EMBO J. 22(7): 1555-1566 (2003).
Tsuchida et al. Activin isoforms signal through type I receptor serine/threonine kinase ALK7. Molecular and Cellular Endocrinology. vol. 220 pp. 59-65 (2004).
Weber, et al., "A silent H-bond can be mutationally activated for high-affinity interaction of BMP-2 and activin type IIB receptor," BMC Structural Biology, 7:6, 1-20. (2007).
Wells, J.A., "Additivity of Mutational Effects in Proteins," Biochemistry, 29(37):8509-8517 (1990).
Welt, C.K., et al., "Activin: an endocrine or panacrine agent?," European Journal of Endocrinology, 139:469-471 (1998).
Wiater, et al., "Inhibin is an Antagonist of Bone Morphogenetic Protein Signaling," The Journal of Biological Chemistry 278(10):7934-7941 (2003).
Wolfman, N.M., et al., "Activation of latent myostatin by the BMP-1/tolloid family of metalloproteinases," PNAS, 100(26):15842-15846 (2003).
Yokota, T., et al., "Isolation and characterization of a mouse cDNA clone that expresses mast-cell growth-factor activity in monkey cells," Proc. Natl. Acad. Sci. USA, 81:1070-1074 (1984).
Yu et al., "Specific roles of activin/inhibin in human erythropoiesis in vitro," Annals New York Academy of Sciences, 20(10):1243-1246 (1991).
Yu, J., et al., "Importance of FSH-releasing protein and inhibin in erythrodifferentiation," Nature, 330:765-767 (1987).
Zhao, B., et al., "Transgenic expression of myostatin propeptide prevents diet-induced obesity and insulin resistance," Biochemical and Biophysical Research Communications, 337:248-255 (2005).
Abaza, M.S.I., et al., Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin, Journal of Protein Chemistry, 11(5):433-444 (1992).
Allendorph, G.P., et al., "Structure of the ternary signaling complex of a TGF-β superfamily member," PNAS, 103(20):7643-7648 (2006).
Banks, G.B., et al., "The Value of Mammalian Models for Duchenne Muscular Dystrophy in Developing Therapeutic Strategies," Current Topics in Developmental Biology, 84:431-453 (2008).
Benny Klimek, Margaret E., et al., "Acute inhibition of myostatin-family proteins preserves skeletal muscle in mouse models of cancer cachexia," Biochemical and Biophysical Research Communications, 391:1548-1554 (2010).
Berenson, J.R., "Multiple Myeloma," Multiple Myeloma: Plasma Cell Disorders: Merck Manual Professional, pp. 1-5, Jul. 2008.
Binkert, et al., "Cloning, sequence analysis and expression of a cDNA encoding a novel insulin-like growth factor binding protein (IGFBP-2)," The EMBO Journal, 8(9):2497-2502 (1989).
Bodey, B., et al., "Failure of Cancer Vaccines: The Significant Limitations of this Approach to Immunotherapy," Anticancer Research, 20:2665-2676 (2000).
Bogdanovich, S., et al., "Functional improvement of dystrophic muscle by myostatin blockade," Nature, 420:418-421 (2002).

(56) References Cited

OTHER PUBLICATIONS

Cadena, S.M., et al., "Administration of a Soluble Activin Type IIB Receptor Promotes Skeletal Muscle Growth Independent of Fiber Type," Journal of Applied Physiology, 109:635-642 (2010).

Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).

Chamberlain, R.S., et al., "Innovations and strategies for the development of anticancer vaccines," Expert Opinion on Pharmacotherapy, 1(4):603-614 (2000).

Chamow, S.M., and Ashkenazi, A., "Immunoadhesins: Principles and Applications," Tibtech, 14: 52-60 (1996).

Chapman, B., et al., "Effect of intron A from human cytomegalovirus (Towne) immediate-early gene on heterologous expression in mammalian cells," Nucleic Acids Research, 19(14):3979-3986 (1991).

Collins, C.D., "Problems monitoring response in multiple myeloma," Multidisciplinary Symposium: Haematological Malignancies, Cancer Imaging 5:S119-S126 (2005).

Deal, C., "Potential New Drug Targets for Osteoporosis," Nature Clinical Practice, 5(1):20-27 (2009).

Deconinck, N., et al., "Pathophysiology of Duchenne Muscular Dystrophy: Current Hypotheses," Pediatr. Neurol., 36:1-7 (2007).

Delogu, G., Et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).

DePaolo, L.V., et al., "Passive Immunoneutralization with a Monoclonal Antibody Reveals a Role For Endogenous Activin-B in Mediating FSH Hypersecretion during Estrus and Following Ovariectomy of Hypophysectomized, Pituitary-Grafted Rats," Endocrinology, 130(3):1741-1743 (1992).

Eijken, M., "The Activin A-Follistatin System: Potent Regulator of Human Extracellular Matrix Mineralization," The FASEB Journal, 21:2949-2960 (2007).

Fajardo, R. J., et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).

Gilbert, R., et al., "Prolonged dystrophin expression and functional correction of mdx mouse muscle following gene transfer with a helper-dependent (gutted) adenovirus-encoding murine dystrophin," Human Molecular Genetics, 12(11)1287-1299 (2003).

Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).

Greenwald, et al., "Characterization of the Extracellular Ligand-Binding Domain of the Type II Activin Receptor," Biochemistry, 37(47):16711-16718 (1998).

Greenwald, J., et al., "Three-finger toxin fold for the extracellular ligand-binding domain of the type II activin receptor serine kinase," Nature Structural Biology, 6(1):18-22 (1999).

Gregoriadis, G., et al., "Polysialic acids: potential in drug delivery," FEBS, 315(3):271-276 (1993).

Guo, et al., "Protein Tolerance to Random Amino Acid Change," Proc. Natl. Acad. Sci. USA, 101(25):9205-9210 (Jun. 22, 2004). Epub Jun. 14, 2004.

Harrison, C.A., et al., "An Activin Mutant with Disrupted ALK4 Binding Blocks Signaling via Type II Receptors," The Journal of Biological Chemistry, 279(27):28036-28044 (2004).

Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).

Krag, T.O.B., et al., "Heregulin ameliorates the dystrophic phenotype in mdx mice," PNAS, 101(38):13856-13860 (2004).

Kumar, T.R., et al., "Regulation of FSHbeta and GnRH Receptor Gene Expression in Activin Receptor II Knockout Male Mice," Mol. Cell. Endocrinol., 212(1-2):19-27 (2003).

Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).

Kuntz, "Structure-based strategies for drug design and discovery," Science, 257(5073):1078-1082 (1992).

Lotinun, S., et al., "A Soluble Activin Receptor Type IIa Fusion Protein (ACE-011) Increases Bone Mass Via a Dual Anabolic-Antiresorptive Effect in Cynomolgus Monkeys," Bone, 46:1082-1088 (2010).

Lu, S., et al., "Simian Immunodeficiency Virus DNA Vaccine Trial in Macaques," Journal of Virology, 70(6):3978-3991 (1996).

Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).

Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).

Mathews, L.S., et al., "Expression Cloning of an Activin Receptor, a Predicted Transmembrane Serine Kinase," Cell, 65(6):973-982 (1991).

Matzuk et al., "Cloning of the human activin receptor cDNA reveals high evolutionary conservation," Biochim Biophys Acta, 1130(1):105-108 (1992).

McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).

Menstruation: Absent Periods (Amenorrhea), Website downloaded on Jun. 14, 2010, <http//:adam.about.com/reports/000101_2.htm?p=1> (11 pages).

Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.

Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.

Miller et al., Ligand binding to proteins: the binding landscape model. Protein Sci., 6(10):2166-79 (1997).

Miura, P., et al., "Utrophin upregulation for treating Duchenne or Becker muscular dystrophy: how close are we?" Trends in Molecular Medicine, 12(3):122-129 (2006).

Mosekilde, L., et al., "Emerging Anabolic Treatments in Osteoporosis," Current Drug Safety, 6:62-74 (2011).

Murata, T., et al., "Anti-activin a Antibody (IgY) Specifically Neutralizes Various Activin A Activities," Proceedings of the Society for Experimental Biology & Medicine, 211(1):100-107 (1996).

Patel, K., et al., "The function of Myostatin and strategies of Myostatin blockade—new hope for therapies aimed at promoting growth of skeletal muscle," Neuromuscular Disorders, 15:117-126 (2005).

Perrien, D. S., et al., "Inhibin A Is an Endocrine Stimulator of Bone Mass and Strength," Endocrinology, 148(4):1654-1665 (2007).

Phillips, A.J., "The challenge of gene therapy and DNA delivery," J. Pharm. Pharmacology, 53:1169-1174 (2001).

Pirollo, K.F., et al., "Targeted Delivery of Small Interfering RNA: Approaching Effective Cancer Therapies," Cancer Res., 68(5):1247-1250 (2008).

Qi, Z., et al., "Blockade of type β transforming growth factor signaling prevents liver fibrosis and dysfunction in the rat," PNAS, 96:2345-2349 (1999).

Raju, T.S., "Glycosylation in the Fc domain of IgG increases resistance to proteolytic cleavage by papain," Biochemical and Biophysical Research Communications, 341:797-803 (2006).

(56) References Cited

OTHER PUBLICATIONS

Rodriguez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).

Rosenzweig et al., "Cloning and characterization of a human type II receptor for bone morphogenetic proteins," PNAS, 92:7632-7636 (1995).

Ruckle, J., et al., Single-Dose, Randomized, Double-Blind, Placebo-Controlled Study of ACE-011 (ActRIIA-IgG1) in Postmenopausal Women, Journal of Bone and Mineral Research, 24(4):744-752 (2009).

Sako, D., et al., "Characterization of the Ligand Binding Functionality of the Extracellular Domain of Activin Receptor Type IIB," The Journal of Biological Chemistry, 285(27):21037-21048 (2010).

Schmelzer, C.H., et al., "Purification and Characterization of Recombinant Human Activin B," Biochimica et Biophysica Acta, 1039(2):135-141 (1990).

Thompson, T. B., et al., "Beta A versus beta B: is it merely a matter of expression?" Molecular and Cellular Endocrinology, 225:9-17 (2004).

Tinsley, J., et al., "Expression of full-length utrophin prevents muscular dystrophy in *mdx* mice," Nature Medicine, 4(12):1441-1444 (1998).

Tisdale, M.J., "Cachexia in Cancer Patients," Nat. Rev. Cancer, 2:862-871 (2002).

Tokuriki, N., et al., "Stability effects of mutations and protein evolvability," Current Opinion in Structural Biology, 19:596-604 (2009).

Trivedi, R., et al., "Investigational Anabolic Therapies for Osteoporosis," Expert Opin. Investig. Drugs, 19(8):995-1005 (2010).

Tu, P., et al., "Genetic Disruption of Myostatin Reduces the Development of Proatherogenic Dyslipidemia and Atherogenic Lesions in Ldlr Null Mice," Diabetes, 58:1739-1748 (2009).

Type 2 Diabetes, PubMed Health, Diseases and Conditions, U.S. National Library of Medicine, Bethesda, MD (online), Jun. 28, 2011 [retrieved on Jun. 25, 2012). Retrieved from the Internet:<URL:http://www.ncbi.nlm.nih.gov/pubmedhealth/PMH0001356/>.

Ukkola, et al., "Adiponectin: A Link Between Excess Adiposity and Associated Comorbidities?", Journal of Molecular Medicine, 80(11):696-702 (2002).

Utzschneider, et al., The Role of Insulin Resistance in Nonalcoholoc Fatty Liver Disease, J. Clin. Endocrinol. Metab., 91(12):4753-4761 (Dec. 2006). Epub Sep. 12, 2006.

Vallet, S., et al., "Activin A promotes multiple myeloma-induced osteolysis and is a promising target for myeloma bone disease," PNAS, 107(11):5124-5129 (2010).

Vidal, L., et al., "Making sense of antisense," European Journal of Cancer, 41:2812-2818 (2005).

Wagner, K.R., et al., "A Phase I/II trial of MYO-029 in Adult Subjects with Muscular Dystrophy," Ann. Neurol., 63:561-571 (2008).

Wagner, K.R., et al., "Loss of Myostatin Attenuates Severity of Muscular Dystrophy in mdx Mice," Ann. Neurol., 52:832-836 (2002).

Wagner, K.R., et al., "Muscle regeneration in the prolonged absence of myostatin," PNAS, 102(7):2519-2524 (2005).

Walsh, F. S, et al., "Myostatin: a modulator of skeletal-muscle stems cells," Biochemical Society Transactions, 33(Pt.6):1513-1517 (2005).

Wang, et al., A single amino acid determines lysophospholipid specificity of the S1P1 (EDG1) and LPA1 (EDG2) phospholipid growth factor receptors. JBC 276:49213-49220 (2001).

Wang, W., et al., "GDF-3 is an adipogenic cytokine under high fat dietary condition," Biochemical and Biophysical Research Comm., 321(4):1024-1031 (2004).

\* cited by examiner

| @ 12 weeks | OVX-VEH | OVX-RAP-011 | SHAM-VEH | SHAM-RAP-011 |
|---|---|---|---|---|
| Tb N (mm$^{-1}$) | 2.1 ± 0.3 | 3.5 ± 0.2 ** | 3.0 ± 0.2 | 4.1 ± 0.2 ** |
| Tb Sp (μm) | 486.2 ± 79 | 283.9 ± 21 ** | 332.4 ± 25 | 230.2 ± 12 ** |
| Conn D (mm$^{-3}$) | 8.4 ± 6 | 85.1 ± 13.7 ** | 41.4 ± 14.8 | 131.2 ± 16.5 ** |

** $P < 0.01$ vs VEH

Figure 20

|  | BV/TV (%) | ES/BS (%) | Nob/BPm ( /mm) | Noc/BPm ( /mm) | Ms/Bs (%) | MAR (um/day) | BFR/BSd (um³/um²/day) |
|---|---|---|---|---|---|---|---|
| PBS mean | 7.53 | 17.36 | 49.33 | 7.55 | 4.206 | 0.704 | 0.029 |
| RAP-011 mean | 10.88 | 13.93 | 40.89 | 5.34 | 7.546 | 0.852 | 0.065 |
| *P value* | *0.002* | *0.03* | *0.02* | *0.01* | *0.008* | *0.03* | *0.002* |

Figure 24

METHOD FOR PROMOTING BONE GROWTH USING ACTIVIN-ACTRIIA ANTAGONISTS

RELATED APPLICATIONS

This application is a continuation of U.S. applicaton Ser. No. 12/284,862, filed Sep. 24, 2008, which is a continuation of U.S. application Ser. No. 11/603,485, filed Nov. 22, 2006, which claims the benefit of U.S. Provisional Application Nos. 60/739,462, filed Nov. 23, 2005, 60/783,322, filed Mar, 17, 2006, and 60/844,855, filed Sep, 15, 2006, which applications are hereby incorporated by referenced in their entireties.

SEQUENCE LISTING

The instant application contains a Sequence Listing which has been submitted via EFS-Web and is hereby incorporated by reference in its entirety. Said ASCII copy, created on Nov. 8, 2011, is named PHPHP04019.txt, and is 22,310 bytes in size.

BACKGROUND OF THE INVENTION

Disorders of the bone, ranging from osteoporosis to fractures, represent a set of pathological states for which there are few effective pharmaceutical agents. Treatment instead focuses on physical and behavioral interventions, including immobilization, exercise and changes in diet. It would be beneficial to have therapeutic agents that promote bone growth and increase bone density for the purpose of treating a variety of bone disorders.

Bone growth and mineralization are dependent on the activities of two cell types, osteoclasts and osteoblasts, although chondrocytes and cells of the vasculature also participate in critical aspects of these processes. Developmentally, bone formation occurs through two mechanisms, endochondral ossification and intramembranous ossification, with the former responsible for longitudinal bone formation and the later responsible for the formation of topologically flat bones, such as the bones of the skull. Endochondral ossification requires the sequential formation and degradation of cartilaginous structures in the growth plates that serve as templates for the formation of osteoblasts, osteoclasts, the vasculature and subsequent mineralization. During intramembranous ossification, bone is formed directly in the connective tissues. Both processes require the infiltration of osteoblasts and subsequent matrix deposition.

Fractures and other structural disruptions of bone are healed through a process that, at least superficially, resembles the sequence of developmental events of osteogenesis, including the formation of cartilaginous tissue and subsequent mineralization. The process of fracture healing can occur in two ways. Direct or primary bone healing occurs without callus formation. Indirect or secondary bone healing occurs with a callus precursor stage. Primary healing of fractures involves the reformation of mechanical continuity across a closely-set disruption. Under suitable conditions, bone-resorbing cells surrounding the disruption show a tunnelling resorptive response and establish pathways for the penetration of blood vessels and subsequent healing. Secondary healing of bones follows a process of inflammation, soft callus formation, callus mineralisation and callus remodelling. In the inflammation stage, haematoma and haemorrhage formation results from the disruption of periosteal and endosteal blood vessels at the site of injury. Inflammatory cells invade the area. In soft callus formation stage, the cells produce new vessels, fibroblasts, intracellular material and supporting cells, forming granulation tissue in the space between the fracture fragments. Clinical union across the disruption is established by fibrous or cartilaginous tissue (soft callus). Osteoblasts are formed and mediate the mineralization of soft callus, which is then replaced by lamellar bone and subjected to the normal remodeling processes.

In addition to fractures and other physical disruptions of bone structure, loss of bone mineral content and bone mass can be caused by a wide variety of conditions and may result in significant medical problems. Changes to bone mass occur in a relatively predictable way over the life of an individual. Up to about age 30, bones of both men and women grow to maximal mass through linear growth of the endochondral growth plates and radial growth. After about age 30 (for trabecular bone, e.g., flat bones such as the vertebrae and pelvis) and age 40 (for cortical bone, e.g., long bones found in the limbs), slow bone loss occurs in both men and women. In women, a final phase of substantial bone loss also occurs, probably due to postmenopausal estrogen deficiencies. During this phase, women may lose an additional 10% of bone mass from the cortical bone and 25% from the trabecular compartment. Whether progressive bone loss results in a pathological condition such as osteoporosis depends largely on the initial bone mass of the individual and whether there are exacerbating conditions.

Bone loss is sometimes characterized as an imbalance in the normal bone remodeling process. Healthy bone is constantly subject to remodeling. Remodeling begins with resorption of bone by osteoclasts. The resorbed bone is then replaced by new bone tissue, which is characterized by collagen formation by osteoblasts, and subsequent calcification. In healthy individuals the rates of resorption and formation are balanced. Osteoporosis is a chronic, progressive condition, marked by a shift towards resorption, resulting in an overall decrease in bone mass and bone mineralization. Osteoporosis in humans is preceded by clinical osteopenia (bone mineral density that is greater than one standard deviation but less than 2.5 standard deviations below the mean value for young adult bone). Worldwide, approximately 75 million people are at risk for osteoporosis.

Thus, methods for controlling the balance between osteoclast and osteoblast activity can be useful for promoting the healing of fractures and other damage to bone as well as the treatment of disorders, such as osteoporosis, associated with loss of bone mass and bone mineralization.

With respect to osteoporosis, estrogen, calcitonin, osteocalcin with vitamin K, or high doses of dietary calcium are all used as therapeutic interventions. Other therapeutic approaches to osteoporosis include bisphosphonates, parathyroid hormone, calcimimetics, statins, anabolic steroids, lanthanum and strontium salts, and sodium fluoride. Such therapeutics, however, are often associated with undesirable side effects.

Thus, it is an object of the present disclosure to provide compositions and methods for promoting bone growth and mineralization.

SUMMARY OF THE INVENTION

In part, the disclosure demonstrates that molecules having activin or ActRIIa antagonist activity ("activin antagonists" and "ActRIIa antagonists") can be used to increase bone density, promote bone growth, and/or increase bone strength. In particular, the disclosure demonstrates that a soluble form of ActRIIa acts as an inhibitor of activin-ActRIIa signaling and promotes increased bone density, bone growth, and bone strength in vivo. While most pharmaceutical agents that promote bone growth or inhibit bone loss act as either anti-catabolic agents (also commonly referred to as "catabolic agents") (e.g., bisphosphonates) or anabolic agents (e.g., parathyroid hormone, PTH, when appropriately dosed), the soluble ActRIIa protein exhibits dual activity, having both catabolic and anabolic effects. Thus, the disclosure establishes that antagonists of the activin-ActRIIa signaling pathway may be used to increase bone density and promote bone growth. While soluble ActRIIa may affect bone through a mechanism other than activin antagonism, the disclosure nonetheless demonstrates that desirable therapeutic agents may be selected on the basis of an activin-ActRIIa antagonist activity. Therefore, in certain embodiments, the disclosure provides methods for using activin-ActRIIa antagonists, including, for example, activin-binding ActRIIa polypeptides, anti-activin antibodies, anti-ActRIIa antibodies, activin- or ActRIIa-targeted small molecules and aptamers, and nucleic acids that decrease expression of activin and ActRIIa, to treat disorders associated with low bone density or low bone strength, such as osteoporosis, or to promote bone growth in patients in need thereof, such as in patients having a bone fracture. Additionally, the soluble ActRIIa polypeptide promotes bone growth without causing a consistently measurable increase in muscle mass In certain aspects, the disclosure provides polypeptides comprising a soluble, activin-binding ActRIIa polypeptide that binds to activin. ActRIIa polypeptides may be formulated as a pharmaceutical preparation comprising the activin-binding ActRIIa polypeptide and a pharmaceutically acceptable carrier. Preferably, the activin-binding ActRIIa polypeptide binds to activin with a $K_D$ less than 1 micromolar or less than 100, 10 or 1 nanomolar. Optionally, the activin-binding ActRIIa polypeptide selectively binds activin versus GDF11 and/or GDF8, and preferably with a $K_D$ that is at least 10-fold, 20-fold or 50-fold lower with respect to activin than with respect to GDF11 and/or GDF8. While not wishing to be bound to a particular mechanism of action, it is expected that this degree of selectivity for activin inhibition over GDF11/GDF8 inhibition accounts for the selective effect on bone without a consistently measurable effect on muscle. In many embodiments, an ActRIIa polypeptide will be selected for causing less than 15%, less than 10% or less than 5% increase in muscle at doses that achieve desirable effects on bone. Preferably the composition is at least 95% pure, with respect to other polypeptide components, as assessed by size exclusion chromatography, and more preferably, the composition is at least 98% pure. An activin-binding ActRIIa polypeptide for use in such a preparation may be any of those disclosed herein, such as a polypeptide having an amino acid sequence selected from SEQ ID NOs: 2, 3, 7 or 12, or having an amino acid sequence that is at least 80%, 85%, 90%, 95%, 97% or 99% identical to an amino acid sequence selected from SEQ ID NOs: 2, 3, 7, 12 or 13. An activin-binding ActRIIa polypeptide may include a functional fragment of a natural ActRIIa polypeptide, such as one comprising at least 10, 20 or 30 amino acids of a sequence selected from SEQ ID NOs: 1-3 or a sequence of SEQ ID NO: 2, lacking the C-terminal 10 to 15 amino acids (the "tail").

A soluble, activin-binding ActRIIa polypeptide may include one or more alterations in the amino acid sequence (e.g., in the ligand-binding domain) relative to a naturally occurring ActRIIa polypeptide. Examples of altered ActRIIa polypeptides are provided in WO 2006/012627, pp. 59-60, incorporated by reference herein. The alteration in the amino acid sequence may, for example, alter glycosylation of the polypeptide when produced in a mammalian, insect or other eukaryotic cell or alter proteolytic cleavage of the polypeptide relative to the naturally occurring ActRIIa polypeptide.

An activin-binding ActRIIa polypeptide may be a fusion protein that has, as one domain, an ActRIIa polypeptide (e.g., a ligand-binding portion of an ActRIIa) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. An activin-binding ActRIIa fusion protein may include an immunoglobulin Fc domain (wild-type or mutant) or a serum albumin or other polypeptide portion that provides desirable properties such as improved pharmacokinetics, improved solubility or improved stability. In a preferred embodiment, an ActRIIa-Fc fusion comprises a relatively unstructured linker positioned between the Fc domain and the extracellular ActRIIa domain. This unstructured linker may correspond to the roughly 15 amino acid unstructured region at the C-terminal end of the extracellular domain of ActRIIa (the "tail"), or it may be an artificial sequence of 1, 2, 3, 4 or 5 amino acids or a length of between 5 and 15, 20, 30, 50 or more amino acids that are relatively free of secondary structure, or a mixture of both. A linker may be rich in glycine and proline residues and may, for example, contain a single sequence of threonine/serine and glycines or repeating sequences of threonine/serine and glycines (e.g., $TG_4$ or $SG_4$ singlets or repeats). A fusion protein may include a purification subsequence, such as an epitope tag, a FLAG tag, a polyhistidine sequence, and a GST fusion. Optionally, a soluble ActRIIa polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a bone disorder. Preferably, a pharmaceutical preparation is substantially pyrogen free. In general, it is preferable that an ActRIIa protein be expressed in a mammalian cell line that mediates suitably natural glycosylation of the ActRIIa protein so as to diminish the likelihood of an unfavorable immune response in a patient. Human and CHO cell lines have been used successfully, and it is expected that other common mammalian expression systems will be useful.

As described herein, ActRIIa proteins designated ActRIIa-Fc (a form with a minimal linker between the ActRIIa portion and the Fc portion) have desirable properties, including selective binding to activin versus GDF8 and/or GDF11, high affinity ligand binding and serum half life greater than two weeks in animal models. In certain embodiments the invention provides ActRIIa-Fc polypeptides and pharmaceutical preparations comprising such polypeptides and a pharmaceutically acceptable excipient.

In certain aspects, the disclosure provides nucleic acids encoding a soluble activin-binding ActRIIa polypeptide. An isolated polynucleotide may comprise a coding sequence for a soluble, activin-binding ActRIIa polypeptide, such as described above. For example, an isolated nucleic acid may include a sequence coding for an extracellular domain (e.g., ligand-binding domain) of an ActRIIa and a sequence that would code for part or all of the transmembrane domain and/or the cytoplasmic domain of an ActRIIa, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIa polynucleotide sequence such as SEQ ID NO: 4 or 5, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRIIa. A preferred nucleic acid sequence is SEQ ID NO:14. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble, activin-binding ActRIIa polypeptide. Such a method may include expressing any of the nucleic acids (e.g., SEQ ID NO: 4, 5 or 14) disclosed herein in a suitable cell, such as a Chinese hamster ovary (CHO) cell. Such a method may comprise: a) culturing a cell under conditions suitable for expression of the soluble ActRIIa polypeptide, wherein said cell is transformed with a soluble ActRIIa expression construct; and b) recovering the soluble ActRIIa polypeptide so expressed. Soluble ActRIIa polypeptides may be recovered as crude, partially purified or highly purified fractions. Purification may be achieved by a series of purification steps, including, for example, one, two or three or more of the following, in any order: protein A chromatography, anion exchange chromatography (e.g., Q sepharose), hydrophobic interaction chromatography (e.g., phenylsepharose), size exclusion chromatography, and cation exchange chromatography.

In certain aspects, an activin-ActRIIa antagonist disclosed herein, such as a soluble, activin-binding ActRIIa polypeptide, may be used in a method for promoting bone growth or increasing bone density in a subject. In certain embodiments, the disclosure provides methods for treating a disorder associated with low bone density, or to promote bone growth, in patients in need thereof. A method may comprise administering to a subject in need thereof an effective amount of activin-ActRIIa antagonist. In certain aspects, the disclosure provides uses of activin-ActRIIa antagonist for making a medicament for the treatment of a disorder or condition as described herein.

In certain aspects, the disclosure provides a method for identifying an agent that stimulates growth of, or increased mineralization of, bone. The method comprises: a) identifying a test agent that binds to activin or a ligand-binding domain of an ActRIIa polypeptide; and b) evaluating the effect of the agent on growth of, or mineralization of, bone.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 20 shows the effects of ActrIIa-mFc on trabecular architecture in the distal femur.

FIG. 24 shows bone histomorphometry indicating that ActRIIa-mFc has dual anabolic and anti-resorptive activity.

DETAILED DESCRIPTION OF THE INVENTION

1. Overview

Figure 1:
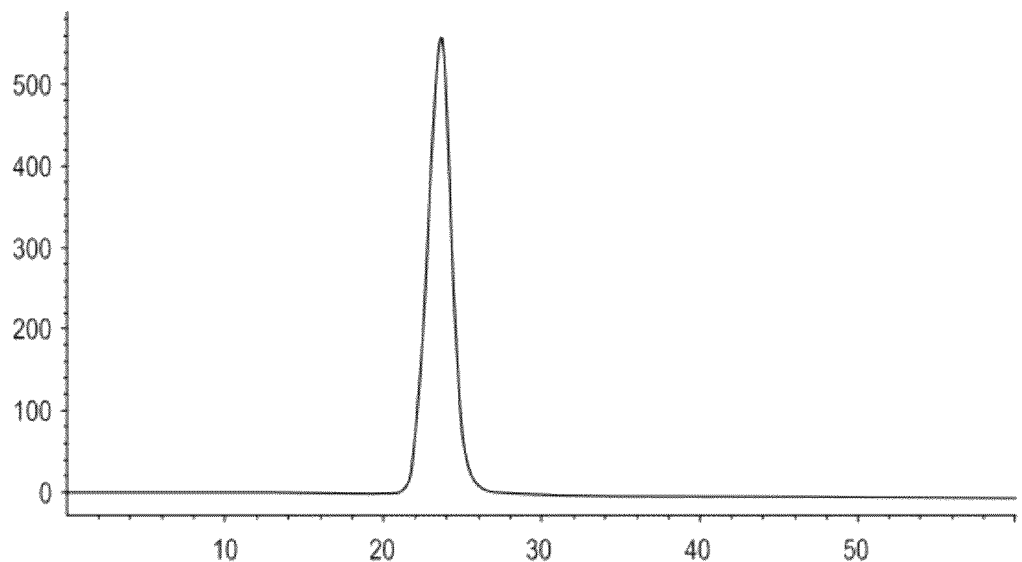
FIG. 1 shows the purification of ActRIIa-hFc expressed in CHO cells. The protein purifies as a single, well-defined peak.
Figure 1:
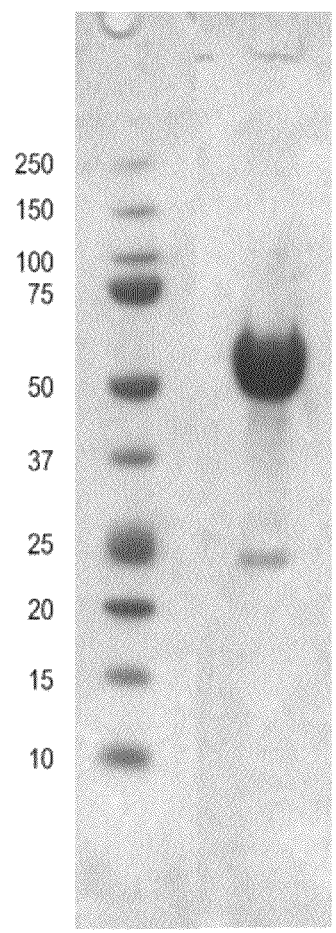

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat. Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Activins are dimeric polypeptide growth factors that belong to the TGF-beta superfamily. There are three principle activin forms (A, B, and AB) that are homo/heterodimers of two closely related β subunits ($\beta_A\beta_A$, $\beta_B\beta_B$, and $\beta_A\beta_B$). The human genome also encodes an activin C and an activin E, which are primarily expressed in the liver. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198: 500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It has been suggested that activin A acts as a natural, positive regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell. Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIa and ActRIIb, have been identified as the type II receptors for activins (Mathews and Vale, 1991, Cell 65:973-982; Attisano et al., 1992, Cell 68: 97-108). Besides activins, ActRIIa and ActRIIb can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell. 7: 949-957; Oh et al., 2002, Genes Dev. 16:2749-54). ALK4 is the primary type I receptor for activins, particularly for activin A, and ALK-7 may serve as a receptor for activins as well, particularly for activin B.

As demonstrated herein, a soluble ActRIIa polypeptide (sActRIIa), which shows substantial preference in binding to activin A as opposed to other TGF-beta family members, such as GDF8 or GDF11, is effective to promote bone growth and increase bone density in vivo. While not wishing to be bound to any particular mechanism, it is expected that the effect of sActRIIa is caused primarily by an activin antagonist effect, given the very strong activin binding (picomolar dissociation constant) exhibited by the particular sActRIIa construct used in these studies. Regardless of mechanism, it is apparent from the data presented herein that ActRIIa-activin antagonists do increase bone density in normal mice and in mouse models for osteoporosis. It should be noted that bone is a dynamic tissue, with growth or shrinkage and increased or decreased density depending on a balance of factors that produce bone and stimulate mineralization (primarily osteoblasts) and factors that destroy and demineralize bone (primarily osteoclasts). Bone growth and mineralization may be increased by increasing the productive factors, by decreasing the destructive factors, or both. The terms "promote bone growth" and "increase bone mineralization" refer to the observable physical changes in bone and are intended to be neutral as to the mechanism by which changes in bone occur.

The mouse models for osteoporosis and bone growth/density that were used in the studies described herein are considered to be highly predictive of efficacy in humans, and therefore, this disclosure provides methods for using ActRIIa polypeptides and other activin-ActRIIa antagonists to promote bone growth and increase bone density in humans. Activin-ActRIIa antagonists include, for example, activin-binding soluble ActRIIa polypeptides, antibodies that bind to activin (particularly the activin A or B subunits, also referred to as βA or βB) and disrupt ActRIIa binding, antibodies that bind to ActRIIa and disrupt activin binding, non-antibody proteins selected for activin or ActRIIa binding (see e.g., WO/2002/088171, WO/2006/055689, WO/2002/032925, WO/2005/037989, US 2003/0133939, and US 2005/0238646 for examples of such proteins and methods for design and selection of same), randomized peptides selected for activin or ActRIIa binding, often affixed to an Fc domain. Two different proteins (or other moieties) with activin or ActRIIa binding activity, especially activin binders that block the type I (e.g., a soluble type I activin receptor) and type II (e.g., a soluble type II activin receptor) binding sites, respectively, may be linked together to create a bifunctional binding molecule. Nucleic acid aptamers, small molecules and other agents that inhibit the activin-ActRIIa signaling axis. Various proteins have activin-ActRIIa antagonist activity, including inhibin (i.e., inhibin alpha subunit), although inhibin does not universally antagonize activin in all tissues, follistatin (e.g., follistatin-288 and follistatin-315), Cerberus, FSRP, endoglin, activin C, alpha(2)-macroglobulin, and an M108A (methionine to alanine change at position 108) mutant activin A. Generally, alternative forms of activin, particularly those with alterations in the type I receptor binding domain can bind to type II receptors and fail to form an active ternary complex, thus acting as antagonists. Additionally, nucleic acids, such as antisense molecules, siRNAs or ribozymes that inhibit activin A, B, C or E, or, particularly, ActRIIa expression, can be used as activin-ActRIIa antagonists. Preferably, the activin-ActRIIa antagonist to be used will exhibit selectivity for inhibiting activin-mediated signaling versus other members of the TGF-beta family, and particularly with respect to GDF8 and GDF11. Soluble ActRIIb proteins do bind to activin, however, the wild type protein does not exhibit significant selectivity in binding to activin versus GDF8/11, and preliminary experiments suggest that this protein does not provide the desired effects on bone, while also causing substantial muscle growth. However, altered forms of ActRIIb with different binding properties have been identified (see, e.g., WO 2006/012627, pp. 55-59, incorporated herein by reference) and these proteins may achieve the desired effects on bone. Native or altered ActRIIb may be given added specificity for activin by coupling with a second, activin-selective binding agent.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Δ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRIIa Polypeptides

In certain aspects, the present invention relates to ActRIIa polypeptides. As used herein, the term "ActRIIa" refers to a family of activin receptor type IIa (ActRIIa) proteins from any species and variants derived from such ActRIIa proteins by mutagenesis or other modification. Reference to ActRIIa herein is understood to be a reference to any one of the currently identified forms. Members of the ActRIIa family are generally transmembrane proteins, composed of a ligand-binding extracellular domain with a cysteine-rich region, a transmembrane domain, and a cytoplasmic domain with predicted serine/threonine kinase activity.

The term "ActRIIa polypeptide" includes polypeptides comprising any naturally occurring polypeptide of an ActRIIa family member as well as any variants thereof (including mutants, fragments, fusions, and peptidomimetic forms) that retain a useful activity. For example, ActRIIa polypeptides include polypeptides derived from the sequence of any known ActRIIa having a sequence at least about 80% identical to the sequence of an ActRIIa polypeptide, and preferably at least 85%, 90%, 95%, 97%, 99% or greater identity. For example, an ActRIIa polypeptide of the invention may bind to and inhibit the function of an ActRIIa protein and/or activin. Preferably, an ActRIIa polypeptide promotes bone growth and bone mineralization. Examples of ActRIIa polypeptides include human ActRIIa precursor polypeptide (SEQ ID NO: 1) and soluble human ActRIIa polypeptides (e.g., SEQ ID NOs: 2, 3, 7 and 12).

The human ActRIIa precursor protein sequence is as follows:

(SEQ ID NO: 1)
MGAAAKLAFAVFLISCSSGAILGRSETQECLFFNANWEKDRTNQTGVE

PCYGDKDKRRHCFATWKNISGSIEIVKQGCWLDDINCYDRTDCVEKKD

SPEVYFCCCEGNMCNEKFSYFPEMEVTQPTSNPVTPKPPYYNILLYSL

VPLMLIAGIVICAFWVYRHHKMAYPPVLVPTQDPGPPPPSPLLGLKPL

QLLEVKARGRFGCVWKAQLLNEYVAVKIFPIQDKQSWQNEYEVYSLPG

MKHENILQFIGAEKRGTSVDVDLWLITAFHEKGSLSDFLKANVVSWNE

LCHIAETMARGLAYLHEDIPGLKDGHKPAISHRDIKSKNVLLKNNLTA

CIADFGLALKFEAGKSAGDTHGQVGTRRYMAPEVLEGAINFQRDAFLR

IDMYAMGLVLWELASRCTAADGPVDEYMLPFEEEIGQHPSLEDMQEVV

VHKKKRPVLRDYWQKHAGMAMLCETIEECWDHDAEARLSAGCVGERIT

QMQRLTNIITTEDIVTVVTMVTNVDFPPKESSL

The signal peptide is single underlined; the extracellular domain is in bold and the potential N-linked glycosylation sites are double underlined.

The human ActRIIa soluble (extracellular), processed polypeptide sequence is as follows:

(SEQ ID NO: 2)
ILGRSETQECLFFNANWEKDRTNQTGVEPCYGDKDKRRHCFATWKNIS

GSIEIVKQGCWLDDINCYDRTDCVEKKDSPEVYFCCCEGNMCNEKFSY

FPEMEVTQPTSNPVTPKPP

The C-terminal "tail" of the extracellular domain is underlined. The sequence with the "tail" deleted (a Δ15 sequence) is as follows:

(SEQ ID NO: 3)
ILGRSETQECLFFNANWEKDRTNQTGVEPCYGDKDKRRHCFATWKNIS

GSIEIVKQGCWLDDINCYDRTDCVEKKDSPEVYFCCCEGNMCNEKFSY

FPEM

The nucleic acid sequence encoding human ActRIIa precursor protein is as follows (nucleotides 164-1705 of Genbank entry NM_001616):

(SEQ ID NO: 4)
ATGGGAGCTGCTGCAAAGTTGGCGTTTGCCGTCTTTCTTATCTCCTGT

TCTTCAGGTGCTATACTTGGTAGATCAGAAACTCAGGAGTGTCTTTTC

TTTAATGCTAATTGGGAAAAGACAGAACCAATCAAACTGGTGTTGAA

CCGTGTTATGGTGACAAAGATAAACGGCGGCATTGTTTTGCTACCTGG

AAGAATATTTCTGGTTCCATTGAAATAGTGAAACAAGGTTGTTGGCTG

GATGATATCAACTGCTATGACAGGACTGATTGTGTAGAAAAAAAAGAC

AGCCCTGAAGTATATTTTTGTTGCTGTGAGGGCAATATGTGTAATGAA

AAGTTTTCTTATTTTCCAGAGATGGAAGTCACACAGCCCACTTCAAAT

CCAGTTACACCTAAGCCACCCTATTACAACATCCTGCTCTATTCCTTG

GTGCCACTTATGTTAATTGCGGGATTGTCATTTGTGCATTTTGGGTG

TACAGGCATCACAAGATGGCCTACCCTCCTGTACTTGTTCCAACTCAA

GACCCAGGACCACCCCCACCTTCTCCATTACTAGGGTTGAAACCACTG

CAGTTATTAGAAGTGAAAGCAAGGGGAAGATTTGGTTGTGTCTGGAAA

GCCCAGTTGCTTAACGAATATGTGGCTGTCAAATATTTCCAATACAG

GACAAACAGTCATGGCAAAATGAATACGAAGTCTACAGTTTGCCTGGA

ATGAAGCATGAGAACATATTACAGTTCATTGGTGCAGAAAAACGAGGC

ACCAGTGTTGATGTGGATCTTTGGCTGATCACAGCATTTCATGAAAAG

GGTTCACTATCAGACTTTCTTAAGGCTAATGTGGTCTCTTGGAATGAA

CTGTGTCATATTGCAGAAACCATGGCTAGAGGATTGGCATATTTACAT

GAGGATATACCTGGCCTAAAAGATGGCCACAAACCTGCCATATCTCAC

AGGGACATCAAAAGTAAAAATGTGCTGTTGAAAAACAACCTGACAGCT

TGCATTGCTGACTTTGGGTTGGCCTTAAAATTTGAGGCTGGCAAGTCT

GCAGGCGATACCCATGGACAGGTTGGTACCCGGAGGTACATGGCTCCA

GAGGTATTAGAGGGTGCTATAAACTTCCAAAGGGATGCATTTTTGAGG

ATAGATATGTATGCCATGGGATTAGTCCTATGGGAACTGGCTTCTCGC

TGTACTGCTGCAGATGGACCTGTAGATGAATACATGTTGCCATTTGAG

GAGGAAATTGGCCAGCATCCATCTCTTGAAGACATGCAGGAAGTTGTT

GTGCATAAAAAAAAGAGGCCTGTTTTAAGAGATTATTGGCAGAAACAT

GCTGGAATGGCAATGCTCTGTGAAACCATTGAAGAATGTTGGGATCAC

GACGCAGAAGCCAGGTTATCAGCTGGATGTGTAGGTGAAAGAATTACC

CAGATGCAGAGACTAACAAATATTATTACCACAGAGGACATTGTAACA

GTGGTCACAATGGTGACAAATGTTGACTTTCCTCCCAAAGAATCTAGT

CTATGA

The nucleic acid sequence encoding a human ActRIIa soluble (extracellular) polypeptide is as follows:

(SEQ ID NO: 5)
ATACTTGGTAGATCAGAAACTCAGGAGTGTCTTTTCTTTAATGCTAAT

TGGGAAAAAGACAGAACCAATCAAACTGGTGTTGAACCGTGTTATGGT

GACAAAGATAAACGGCGGCATTGTTTTGCTACCTGGAAGAATATTTCT

GGTTCCATTGAAATAGTGAAACAAGGTTGTTGGCTGGATGATATCAAC

TGCTATGACAGGACTGATTGTGTAGAAAAAAAAGACAGCCCTGAAGTA

TATTTTTGTTGCTGTGAGGGCAATATGTGTAATGAAAAGTTTTCTTAT

TTTCCAGAGATGGAAGTCACACAGCCCACTTCAAATCCAGTTACACCT

AAGCCACCC

In a specific embodiment, the invention relates to soluble ActRIIa polypeptides. As described herein, the term "soluble ActRIIa polypeptide" generally refers to polypeptides comprising an extracellular domain of an ActRIIa protein. The term "soluble ActRIIa polypeptide," as used herein, includes any naturally occurring extracellular domain of an ActRIIa protein as well as any variants thereof (including mutants, fragments and peptidomimetic forms). An activin-binding ActRIIa polypeptide is one that retains the ability to bind to activin, particularly activin AA, AB or BB. Preferably, an activin-binding ActRIIa polypeptide will bind to activin AA with a dissociation constant of 1 nM or less. Amino acid sequences of human ActRIIa precursor protein is provided below. The extracellular domain of an ActRIIa protein binds to activin and is generally soluble, and thus can be termed a soluble, activin-binding ActRIIa polypeptide. Examples of soluble, activin-binding ActRIIa polypeptides include the soluble polypeptide illustrated in SEQ ID NOs: 2, 3, 7, 12 and 13. SEQ ID NO:7 is referred to as ActRIIa-hFc, and is described further in the Examples. Other examples of soluble, activin-binding ActRIIa polypeptides comprise a signal sequence in addition to the extracellular domain of an ActRIIa protein, for example, the honey bee mellitin leader sequence (SEQ ID NO: 8), the tissue plaminogen activator (TPA) leader (SEQ ID NO: 9) or the native ActRIIa leader (SEQ ID NO: 10). The ActRIIa-hFc polypeptide illustrated in SEQ ID NO:13 uses a TPA leader.

Functionally active fragments of ActRIIa polypeptides can be obtained by screening polypeptides recombinantly produced from the corresponding fragment of the nucleic acid encoding an ActRIIa polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIa protein or signaling mediated by activin.

Functionally active variants of ActRIIa polypeptides can be obtained by screening libraries of modified polypeptides recombinantly produced from the corresponding mutagenized nucleic acids encoding an ActRIIa polypeptide. The variants can be produced and tested to identify those that can function as antagonists (inhibitors) of ActRIIa protein or signaling mediated by activin. In certain embodiments, a functional variant of the ActRIIa polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated by modifying the structure of an ActRIIa polypeptide for such purposes as enhancing therapeutic efficacy, or stability (e.g., ex vivo shelf life and resistance to proteolytic degradation in vivo). Such modified ActRIIa polypeptides when selected to retain activin binding, are considered functional equivalents of the naturally-occurring ActRIIa polypeptides. Modified ActRIIa polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIa polypeptide results in a functional homolog can be readily determined by assessing the ability of the variant ActRIIa polypeptide to produce a response in cells in a fashion similar to the wild-type ActRIIa polypeptide.

In certain embodiments, the present invention contemplates specific mutations of the ActRIIa polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIa polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIa polypeptide is by chemical or enzymatic coupling of glycosides to the ActRIIa polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIa polypeptide may be accomplished chemically and/or enzymatically. Chemical deglycosylation may involve, for example, exposure of the ActRIIa polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIa polypeptides can be achieved by the use of a variety of endo- and exo-glycosidases as described by Thotakura et al. (1987) Meth. Enzymol. 138:350. The sequence of an ActRIIa polypeptide may be adjusted, as appropriate, depending on the type of expression system used, as mammalian, yeast, insect and plant cells may all introduce differing glycosylation patterns that can be affected by the amino acid sequence of the peptide. In general, ActRIIa proteins for use in humans will be expressed in a mammalian cell line that provides proper glycosylation, such as HEK293 or CHO cell lines, although other mammalian expression cell lines, yeast cell lines with engineered glycosylation enzymes and insect cells are expected to be useful as well.

This disclosure further contemplates a method of generating mutants, particularly sets of combinatorial mutants of an ActRIIa polypeptide, as well as truncation mutants; pools of combinatorial mutants are especially useful for identifying functional variant sequences. The purpose of screening such combinatorial libraries may be to generate, for example, ActRIIa polypeptide variants which can act as either agonists or antagonist, or alternatively, which possess novel activities all together. A variety of screening assays are provided below, and such assays may be used to evaluate variants. For example, an ActRIIa polypeptide variant may be screened for ability to bind to an ActRIIa ligand, to prevent binding of an ActRIIa ligand to an ActRIIa polypeptide or to interfere with signaling caused by an ActRIIa ligand.

The activity of an ActRIIa polypeptide or its variants may also be tested in a cell-based or in vivo assay. For example, the effect of an ActRIIa polypeptide variant on the expression of genes involved in bone production or bone destruction may be assessed. This may, as needed, be performed in the presence of one or more recombinant ActRIIa ligand proteins (e.g., activin), and cells may be transfected so as to produce an ActRIIa polypeptide and/or variants thereof, and optionally, an ActRIIa ligand. Likewise, an ActRIIa polypeptide may be administered to a mouse or other animal, and one or more bone properties, such as density or volume may be assessed.

The healing rate for bone fractures may also be evaluated. Dual-energy x-ray absorptiometry (DEXA) is a well-established, non-invasive, quantitative technique for assessing bone density in an animal. In humans central DEXA systems may be used to evaluate bone density in the spine and pelvis. These are the best predictors of overall bone density. Peripheral DEXA systems may be used to evaluate bone density in peripheral bones, including, for example, the bones of the hand, wrist, ankle and foot. Traditional x-ray imaging systems, including CAT scans, may be used to evaluate bone growth and fracture healing. The mechanical strength of bone may also be evaluated.

Combinatorially-derived variants can be generated which have a selective or generally increased potency relative to a naturally occurring ActRIIa polypeptide. Likewise, mutagenesis can give rise to variants which have intracellular half-lives dramatically different than the corresponding a wild-type ActRIIa polypeptide. For example, the altered protein can be rendered either more stable or less stable to proteolytic degradation or other cellular processes which result in destruction of, or otherwise inactivation of a native ActRIIa polypeptide. Such variants, and the genes which encode them, can be utilized to alter ActRIIa polypeptide levels by modulating the half-life of the ActRIIa polypeptides. For instance, a short half-life can give rise to more transient biological effects and can allow tighter control of recombinant ActRIIa polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIa polypeptide sequences. For instance, a mixture of synthetic oligonucleotides can be enzymatically ligated into gene sequences such that the degenerate set of potential ActRIIa polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIa polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIa polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIa polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, the ActRIIa polypeptides of the invention may further comprise post-translational modifications in addition to any that are naturally present in the ActRIIa polypeptides. Such modifications include, but are not limited to, acetylation, carboxylation, glycosylation, phosphorylation, lipidation, and acylation. As a result, the modified ActRIIa polypeptides may contain non-amino acid elements, such as polyethylene glycols, lipids, poly- or monosaccharide, and phosphates. Effects of such non-amino acid elements on the functionality of a ActRIIa polypeptide may be tested as described herein for other ActRIIa polypeptide variants. When an ActRIIa polypeptide is produced in cells by cleaving a nascent form of the ActRIIa polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIa polypeptides.

In certain aspects, functional variants or modified forms of the ActRIIa polypeptides include fusion proteins having at least a portion of the ActRIIa polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) fusion partners. As another example, a fusion domain may be selected so as to facilitate detection of the ActRIIa polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIa polypeptide is fused with a domain that stabilizes the ActRIIa polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

As a specific example, the present invention provides a fusion protein comprising a soluble extracellular domain of ActRIIa fused to an Fc domain (e.g., SEQ ID NO: 6).

THTCPPCPAPELLGGPSVFLFPPKPKDTLMISRTPEVTCVVVD(A)VS

HEDPEVKFNWYVDGVEVHNAKTKPREEQYNSTYRVVSVLTVLHQDWLN

GKEYKCK(A)VSNKALPVPIEKTISKAKGQPREPQVYTLPPSREEMTK

NQVSLTCLVKGFYPSDIAVEWESNGQPENNYKTTPPVLDSDGPFFLYS

KLTVDKSRWQQGNVFSCSVMHEALHN(A)HYTQKSLSLSPGK*

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ActRIIa polypeptide may be placed C-terminal to a heterologous domain, or, alternatively, a heterologous domain may be placed C-terminal to an ActRIIa polypeptide. The ActRIIa polypeptide domain and the heterologous domain need not be adjacent in a fusion protein, and additional domains or amino acid sequences may be included C- or N-terminal to either domain or between the domains.

In certain embodiments, the ActRIIa polypeptides of the present invention contain one or more modifications that are capable of stabilizing the ActRIIa polypeptides. For example, such modifications enhance the in vitro half life of the ActRIIa polypeptides, enhance circulatory half life of the ActRIIa polypeptides or reduce proteolytic degradation of the ActRIIa polypeptides. Such stabilizing modifications include, but are not limited to, fusion proteins (including, for example, fusion proteins comprising an ActRIIa polypeptide and a stabilizer domain), modifications of a glycosylation site (including, for example, addition of a glycosylation site to an ActRIIa polypeptide), and modifications of carbohydrate moiety (including, for example, removal of carbohydrate moieties from an ActRIIa polypeptide). In the case of fusion proteins, an ActRIIa polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the ActRIIa polypeptides, which are isolated from, or otherwise substantially free of, other proteins. ActRIIa polypeptides will generally be produced by expression from recombinant nucleic acids.

3. Nucleic Acids Encoding ActRIIa Polypeptides

In certain aspects, the invention provides isolated and/or recombinant nucleic acids encoding any of the ActRIIa polypeptides (e.g., soluble ActRIIa polypeptides), including fragments, functional variants and fusion proteins disclosed herein. For example, SEQ ID NO: 4 encodes the naturally occurring human ActRIIa precursor polypeptide, while SEQ ID NO: 5 encodes the processed extracellular domain of ActRIIa. The subject nucleic acids may be single-stranded or double stranded. Such nucleic acids may be DNA or RNA molecules. These nucleic acids may be used, for example, in methods for making ActRIIa polypeptides or as direct therapeutic agents (e.g., in a gene therapy approach).

In certain aspects, the subject nucleic acids encoding ActRIIa polypeptides are further understood to include nucleic acids that are variants of SEQ ID NO: 4 or 5. Variant nucleotide sequences include sequences that differ by one or more nucleotide substitutions, additions or deletions, such as allelic variants.

In certain embodiments, the invention provides isolated or recombinant nucleic acid sequences that are at least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 4 or 5, complement sequence of SEQ ID NO: 4 or 5, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 4 or 5 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIa polypeptide and operably linked to at least one regulatory sequence. Regulatory sequences are art-recognized and are selected to direct expression of the ActRIIa polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIa polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIa polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In a preferred embodiment, a vector will be designed for production of the subject ActRIIa polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIa polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 4 or 5) for one or more of the subject ActRIIa polypeptides. The host cell may be any prokaryotic or eukaryotic cell. For example, an ActRIIa polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ActRIIa polypeptides. For example, a host cell transfected with an expression vector encoding an ActRIIa polypeptide can be cultured under appropriate conditions to allow expression of the ActRIIa polypeptide to occur. The ActRIIa polypeptide may be secreted and isolated from a mixture of cells and medium containing the ActRIIa polypeptide. Alternatively, the ActRIIa polypeptide may be retained cytoplasmically or in a membrane fraction and the cells harvested, lysed and the protein isolated. A cell culture includes host cells, media and other byproducts. Suitable media for cell culture are well known in the art. The subject ActRIIa polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIa polypeptides and affinity purification with an agent that binds to a domain fused to the ActRIIa polypeptide (e.g., a protein A column may be used to purify an ActRIIa-Fc fusion). In a preferred embodiment, the ActRIIa polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIa-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ActRIIa polypeptide, can allow purification of the expressed fusion protein by affinity chromatography using a $Ni^{2+}$ metal resin. The purification leader sequence can then be subsequently removed by treatment with enterokinase to provide the purified ActRIIa polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Alternative Activin and ActRIIa Antagonists

The data presented herein demonstrates that antagonists of activin-ActRIIa signaling can be used to promote bone growth and bone mineralization. Although soluble ActRIIa polypeptides, and particularly ActrIIa-Fc, are preferred antagonists, and although such antagonists may affect bone through a mechanism other than activin antagonism (e.g., activin inhibition may be an indicator of the tendency of an agent to inhibit the activities of a spectrum of molecules, including, perhaps, other members of the TGF-beta superfamily, and such collective inhibition may lead to the desired effect on bone), other types of activin-ActRIIa antagonists are expected to be useful, including anti-activin (e.g., A, B, C or E) antibodies, anti-ActRIIa antibodies, antisense, RNAi or ribozyme nucleic acids that inhibit the production of ActRIIa and other inhibitors of activin or ActRIIa, particularly those that disrupt activin-ActRIIa binding.

An antibody that is specifically reactive with an ActRIIa polypeptide (e.g., a soluble ActRIIa polypeptide) and which either binds competitively to ligand with the ActRIIa polypeptide or otherwise inhibits ActRIIa-mediated signaling may be used as an antagonist of ActRIIa polypeptide activities. Likewise, an antibody that is specifically reactive with an activin A polypeptide and which disrupts ActRIIa binding may be used as an antagonist.

By using immunogens derived from an ActRIIa polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRIIa polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRIIa or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRIIa polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRIIa polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, chimeric, humanized and fully human molecules having affinity for an ActRIIa or activin polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human $V_H$ proteins or camelid $V_{HH}$ proteins). In certain embodiments, an antibody of the invention is a monoclonal antibody, and in certain embodiments, the invention makes available methods for generating novel antibodies. For example, a method for generating a monoclonal antibody that binds specifically to an ActRIIa polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRIIa polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less. Given the extraordinarily tight binding between activin and ActRIIa, it is expected that a neutralizing anti-activin or anti-ActRIIa antibody would generally have a dissociation constant of $10^{-10}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are activin or ActRIIa antagonists include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length ActRIIa nucleic acid sequence or activin 13A or activin 13B nucleic acid sequence. The region of complementarity will preferably be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, bone growth and mineralization.

5. Screening Assays

In certain aspects, the present invention relates to the use of ActRIIa polypeptides (e.g., soluble ActRIIa polypeptides)

and activin polypeptides to identify compounds (agents) which are agonist or antagonists of the activin-ActRIIa signaling pathway. Compounds identified through this screening can be tested to assess their ability to modulate bone growth or mineralization in vitro. Optionally, these compounds can further be tested in animal models to assess their ability to modulate tissue growth in vivo.

There are numerous approaches to screening for therapeutic agents for modulating tissue growth by targeting activin and ActRIIa polypeptides. In certain embodiments, high-throughput screening of compounds can be carried out to identify agents that perturb activin or ActRIIa-mediated effects on bone. In certain embodiments, the assay is carried out to screen and identify compounds that specifically inhibit or reduce binding of an ActRIIa polypeptide to activin. Alternatively, the assay can be used to identify compounds that enhance binding of an ActRIIa polypeptide to activin. In a further embodiment, the compounds can be identified by their ability to interact with an activin or ActRIIa polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIa polypeptide and activin.

Merely to illustrate, in an exemplary screening assay of the present invention, the compound of interest is contacted with an isolated and purified ActRIIa polypeptide which is ordinarily capable of binding to activin. To the mixture of the compound and ActRIIa polypeptide is then added a composition containing an ActRIIa ligand. Detection and quantification of ActRIIa/activin complexes provides a means for determining the compound's efficacy at inhibiting (or potentiating) complex formation between the ActRIIa polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIa polypeptide, and the formation of ActRIIa/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIa polypeptide and activin may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIa polypeptide or activin, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIa polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIa polypeptide and its binding protein. See for example, U.S. Pat. No. 5,283,317; Zervos et al. (1993) Cell 72:223-232; Madura et al. (1993) J Biol Chem 268: 12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRIIa polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRIIa or activin polypeptide of the invention. The interaction between the compound and the ActRIIa or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIa polypeptide. This may include a solid phase or fluid phase binding event. Alternatively, the gene encoding an activin or ActRIIa polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) bone formation and increasing bone mass. Therefore, any compound identified can be tested in whole cells or tissues, in vitro or in vivo, to confirm their ability to modulate bone growth or mineralization. Various methods known in the art can be utilized for this purpose.

For example, the effect of the ActRIIa or activin polypeptides or test compounds on bone or cartilage growth can be determined by measuring induction of Msx2 or differentiation of osteoprogenitor cells into osteoblasts in cell based assays (see, e.g., Daluiski et al., Nat. Genet. 2001, 27(1):84-8; Hino et al., Front Biosci. 2004, 9:1520-9). Another example of cell-based assays includes analyzing the osteogenic activity of the subject ActRIIa or activin polypeptides and test compounds in mesenchymal progenitor and osteoblastic cells. To illustrate, recombinant adenoviruses expressing an activin or ActRIIa polypeptide can be constructed to infect pluripotent mesenchymal progenitor $C3H_{10}T1/2$ cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8):1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. Andersson et al., J. Endocrinol. 170:529-537 describe a mouse osteoporosis model in which mice are ovariectomized, which causes the mice to lose substantial bone mineral content and bone mineral density, with the trabecular bone losing roughly 50% of bone mineral density. Bone density could be increased in the ovariectomized mice by administration of factors such as parathyroid hormone. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

6. Exemplary Therapeutic Uses

In certain embodiments, activin-ActRIIa antagonists (e.g., ActRIIa polypeptides) of the present invention can be used for treating or preventing a disease or condition that is associated with bone damage, whether, e.g., through breakage, loss or demineralization. In certain embodiments, the present invention provides methods of treating or preventing bone damage in an individual in need thereof through administering to the individual a therapeutically effective amount of an activin-ActRIIa antagonist, particularly an ActRIIa polypeptide. In certain embodiments, the present invention provides methods of promoting bone growth or mineralization in an individual in need thereof through administering to the individual a therapeutically effective amount of an activin-ActRIIa antagonist, particularly an ActRIIa polypeptide. These methods are preferably aimed at therapeutic and prophylactic treatments of animals, and more preferably, humans. In certain embodiments, the disclosure provides for the use of activin-ActRIIa antagonists (particularly soluble ActRIIa polypeptides and neutralizing antibodies targeted to activin or ActRIIa) for the treatment of disorders associated with low bone density or decreased bone strength.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician and the intended result of administration of the therapeutic agent.

The disclosure provides methods of inducing bone and/or cartilage formation, preventing bone loss, increasing bone mineralization or preventing the demineralization of bone. For example, the subject activin-ActRIIa antagonists have application in treating osteoporosis and the healing of bone fractures and cartilage defects in humans and other animals. ActRIIa or activin polypeptides may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. In certain cases, the subject activin-ActRIIa antagonists may provide an environment to attract bone-forming cells, stimulate growth of bone-forming cells or induce differentiation of progenitors of bone-forming cells. Activin-ActRIIa antagonists of the invention may also be useful in the treatment of osteoporosis.

Methods and compositions of the invention can be applied to conditions characterized by or causing bone loss, such as osteoporosis (including secondary osteoporosis), hyperparathyroidism, Cushing's disease, Paget's disease, thyrotoxicosis, chronic diarrheal state or malabsorption, renal tubular acidosis, or anorexia nervosa.

Osteoporosis may be caused by, or associated with, various factors. Being female, particularly a post-menopausal female, having a low body weight, and leading a sedentary lifestyle are all risk factors for osteoporosis (loss of bone mineral density, leading to fracture risk). Persons having any of the following profiles may be candidates for treatment with an ActRIIa antagonist: a post-menopausal woman and not taking estrogen or other hormone replacement therapy; a person with a personal or maternal history of hip fracture or smoking; a post-menopausal woman who is tall (over 5 feet 7 inches) or thin (less than 125 pounds); a man with clinical conditions associated with bone loss; a person using medications that are known to cause bone loss, including corticosteroids such as Prednisone™, various anti-seizure medications such as Dilantin™ and certain barbiturates, or high-dose thyroid replacement drugs; a person having type 1 diabetes, liver disease, kidney disease or a family history of osteoporosis; a person having high bone turnover (e.g., excessive collagen in urine samples); a person with a thyroid condition, such as hyperthyroidism; a person who has experienced a fracture after only mild trauma; a person who has had x-ray evidence of vertebral fracture or other signs of osteoporosis.

As noted above, osteoporosis can also result as a condition associated with another disorder or from the use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenyloin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Bone loss resulting from cancer therapy is widely recognized and termed cancer therapy induced bone loss (CTIBL). Bone metastases can create cavities in the bone that may be corrected by treatment with activin-ActRIIa antagonists.

In a preferred embodiment, activin-ActRIIa antagonists, particularly a soluble ActRIIa, disclosed herein may be used in cancer patients. Patients having certain tumors (e.g. prostate, breast, multiple myeloma or any tumor causing hyperparathyroidism) are at high risk for bone loss due to tumor-induced bone loss as well as bone metastases and therapeutic agents. Such patients may be treated with activin-ActRIIa antagonists even in the absence of evidence of bone loss or bone metastases. Patients may also be monitored for evidence of bone loss or bone metastases, and may be treated with activin-ActRIIa antagonists in the event that indicators suggest an increased risk. Generally, DEXA scans are employed to assess changes in bone density, while indicators of bone remodeling may be used to assess the likelihood of bone metastases. Serum markers may be monitored. Bone specific alkaline phosphatase (BSAP) is an enzyme that is present in osteoblasts. Blood levels of BSAP are increased in patients with bone metastasis and other conditions that result in increased bone remodeling. Osteocalcin and procollagen peptides are also associated with bone formation and bone metastases. Increases in BSAP have been detected in patients with bone metastasis caused by prostate cancer, and to a lesser degree, in bone metastases from breast cancer. Bone Morphogenetic Protein-7 (BMP-7) levels are high in prostate cancer that has metastasized to bone, but not in bone metastases due to bladder, skin, liver, or lung cancer. Type I Carboxy-terminal telopeptide (ICTP) is a crosslink found in collagen that is formed during to the resorption of bone. Since bone is constantly being broken down and reformed, ICTP will be found throughout the body. However, at the site of bone metastasis, the level will be significantly higher than in an area of normal bone. ICTP has been found in high levels in bone metastasis due to prostate, lung, and breast cancer. Another collagen crosslink, Type 1 N-terminal telopeptide (NTx), is produced along with ICTP during bone turnover. The amount of NTx is increased in bone metastasis caused by many different types of cancer including lung, prostate, and breast cancer. Also, the levels of NTx increase with the progression of the bone metastasis. Therefore, this marker can be used to both detect metastasis as well as measure the extent of the disease. Other markers of resorption include pyridinoline and deoxypyridinoline. Any increase in resorption markers or markers of bone metastases indicate the need for activin-ActRIIa antagonist therapy in a patient.

Activin-ActRIIa antagonists may be conjointly administered with other pharmaceutical agents. Conjoint administration may be accomplished by administration of a single co-formulation, by simultaneous administration or by administration at separate times. Activin-ActRIIa antagonists may be particularly advantageous if administered with other bone-active agents. A patient may benefit from conjointly receiving activin-ActRIIa antagonist and taking calcium supplements, vitamin D, appropriate exercise and/or, in some cases, other medication. Examples of other medications incude, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation. Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily). Estrogen therapy (ET)/Hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called Selective Estrogen Receptor Modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

7. Pharmaceutical Compositions

In certain embodiments, activin-ActRIIa antagonists (e.g., ActRIIa polypeptides) of the present invention are formulated with a pharmaceutically acceptable carrier. For example, an ActRIIa polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally as an implant or device. When administered, the therapeutic composition for use in this invention is, of course, in a pyrogen-free, physiologically acceptable form. Therapeutically useful agents other than the ActRIIa antagonists which may also optionally be included in the composition as described above, may be administered simultaneously or sequentially with the subject compounds (e.g., ActRIIa polypeptides) in the methods of the invention.

Typically, ActRIIa antagonists will be administered parenterally. Pharmaceutical compositions suitable for parenteral administration may comprise one or more ActRIIa polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone). In certain embodiments, compositions of the present invention may include a matrix capable of delivering one or more therapeutic compounds (e.g., ActRIIa polypeptides) to a target tissue site (e.g., bone), providing a structure for the developing tissue and optimally capable of being resorbed into the body. For example, the matrix may provide slow release of the ActRIIa polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3)

humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIa polypeptides). The various factors include, but are not limited to, amount of bone weight desired to be formed, the degree of bone density loss, the site of bone damage, the condition of the damaged bone, the patient's age, sex, and diet, the severity of any disease that may be contributing to bone loss, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

Experiments with mice have demonstrated that effects of ActRIIa-Fc on bone are detectable when the compound is dosed at intervals and amounts sufficient to achieve serum concentrations of 0.2 µg/kg or greater, and serum levels of 1 µg/kg or 2 µg/kg or greater are desirable for achieving significant effects on bone density and strength. Although there is no indication that higher doses of ActRIIa-Fc are undesirable due to side effects, dosing regimens may be designed to reach serum concentrations of between 0.2 and 15 µg/kg, and optionally between 1 and 5 µg/kg. In humans, serum levels of 0.2 µg/kg may be achieved with a single dose of 0.1 mg/kg or greater and serum levels of 1 µg/kg may be achieved with a single dose of 0.3 mg/kg or greater. The observed serum half-life of the molecule is between about 20 and 30 days, substantially longer than most Fc fusion proteins, and thus a sustained effective serum level may be achieved, for example, by dosing with 0.2-0.4 mg/kg on a weekly or biweekly basis, or higher doses may be used with longer intervals between dosings. For example, doses of 1-3 mg/kg might be used on a monthly or bimonthly basis, and the effect on bone may be sufficiently durable that dosing is necessary only once every 3, 4, 5, 6, 9, 12 or more months.

In certain embodiments, the present invention also provides gene therapy for the in vivo production of ActRIIa polypeptides. Such therapy would achieve its therapeutic effect by introduction of the ActRIIa polynucleotide sequences into cells or tissues having the disorders as listed above. Delivery of ActRIIa polynucleotide sequences can be achieved using a recombinant expression vector such as a chimeric virus or a colloidal dispersion system. Preferred for therapeutic delivery of ActRIIa polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIa polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIa polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

ActRIIa-Fc Fusion Proteins

Applicants constructed a soluble ActRIIa fusion protein that has the extracellular domain of human ActRIIa fused to a human or mouse Fc domain with a minimal linker in between. The constructs are referred to as ActRIIa-hFc and ActRIIa-mFc, respectively.

ActRIIa-hFc is shown below as purified from CHO cell lines (SEQ ID NO: 7):

```
ILGRSETQECLFFNANWEKDRTNQTGVEPCYGDKDKRRHCFATWKNIS
GSIEIVKQGCWLDDINCYDRTDCVEKKDSPEVYFCCCEGNMCNEKFSY
FPEMEVTQPTSNPVTPKPPTGGGTHTCPPCPAPELLGGPSVFLFPPKP
KDTLMISRTPEVTCVVVDVSHEDPEVKFNWYVDGVEVHNAKTKPREEQ
YNSTYRVVSVLTVLHQDWLNGKEYKCKVSNKALPVPIEKTISKAKGQP
REPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQK
SLSLSPGK
```

The ActRIIa-hFc and ActRIIa-mFc proteins were expressed in CHO cell lines. Three different leader sequences were considered:

```
(i) Honey bee mellitin (HBML):
MKFLVNVALVFMVVYISYIYA       (SEQ ID NO: 8)

(ii)
Tissue Plasminogen Activator (TPA):
MDAMKRGLCCVLLLCGAVFVSP      (SEQ ID NO: 9)

(iii) Native:
MGAAAKLAFAVFLISCSSGA.       (SEQ ID NO: 10)
```

The selected form employs the TPA leader and has the following unprocessed amino acid sequence:

```
                                      (SEQ ID NO: 13)
MDAMKRGLCCVLLLCGAVFVSPGAAILGRSETQECLFFNANWEKDRTN
QTGVEPCYGDKDKRRHCFATWKNISGSIEIVKQGCWLDDINCYDRTDC
VEKKDSPEVYFCCCEGNMCNEKFSYFPEMEVTQPTSNPVTPKPPTGGG
THTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKE
YKCKVSNKALPVPIEKTISKAKGQPREPQVYTLPPSREEMTKNQVSLT
CLVKGFYPSDIAVEWESNGQPENNYKTTPPVLDSDGSFFLYSKLTVDK
SRWQQGNVFSCSVMHEALHNHYTQKSLSLSPGK
```

This polypeptide is encoded by the following nucleic acid sequence:

```
                                      (SEQ ID NO: 14)
ATGGATGCAATGAAGAGAGGGCTCTGCTGTGTGCTGCTGCTGTGTGGA
GCAGTCTTCGTTTCGCCCGGCGCCGCTATACTTGGTAGATCAGAAACT
CAGGAGTGTCTTTTTTTAATGCTAATTGGGAAAAAGACAGAACCAATC
AAACTGGTGTTGAACCGTGTTATGGTGACAAAGATAAACGGCGGCATT
GTTTTGCTACCTGGAAGAATATTTCTGGTTCCATTGAATAGTGAAACA
AGGTTGTTGGCTGGATGATATCAACTGCTATGACAGGACTGATTGTGT
AGAAAAAAAAGACAGCCCTGAAGTATATTTCTGTTGCTGTGAGGGCAA
TATGTGTAATGAAAAGTTTTCTTATTTTCCGGAGATGGAAGTCACACA
GCCCACTTCAAATCCAGTTACACCTAAGCCACCCACCGGTGGTGGAAC
TCACACATGCCCACCGTGCCCAGCACCTGAACTCCTGGGGGGACCGTC
AGTCTTCCTCTTCCCCCCAAAACCCAAGGACACCCTCATGATCTCCCG
GACCCCTGAGGTCACATGCGTGGTGGTGGACGTGAGCCACGAAGACCC
TGAGGTCAAGTTCAACTGGTACGTGGACGGCGTGGAGGTGCATAATGC
CAAGACAAAGCCGCGGGAGGAGCAGTACAACAGCACGTACCGTGTGGT
CAGCGTCCTCACCGTCCTGCACCAGGACTGGCTGAATGGCAAGGAGTA
CAAGTGCAAGGTCTCCAACAAAGCCCTCCCAGTCCCCATCGAGAAAAC
CATCTCCAAAGCCAAAGGGCAGCCCCGAGAACCACAGGTGTACACCCT
GCCCCCATCCCGGGAGGAGATGACCAAGAACCAGGTCAGCCTGACCTG
CCTGGTCAAAGGCTTCTATCCCAGCGACATCGCCGTGGAGTGGGAGAG
CAATGGGCAGCCGGAGAACAACTACAAGACCACGCCTCCCGTGCTGGA
CTCCGACGGCTCCTTCTTCCTCTATAGCAAGCTCACCGTGGACAAGAG
CAGGTGGCAGCAGGGGAACGTCTTCTCATGCTCCGTGATGCATGAGGC
TCTGCACAACCACTACACGCAGAAGAGCCTCTCCCTGTCTCCGGGTAA
ATGAGAATTC
```

Both ActRIIa-hFc and ActRIIa-mFc were remarkably amenable to recombinant expression. As shown in FIG. 1, the protein was purified as a single, well-defined peak of protein. N-terminal sequencing revealed a single sequence of –ILGRSETQE (SEQ ID NO: 11). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIa-hFc protein was purified to a purity of >98% as determined by size exclusion chromatography and >95% as determined by SDS PAGE.

Figure 2:
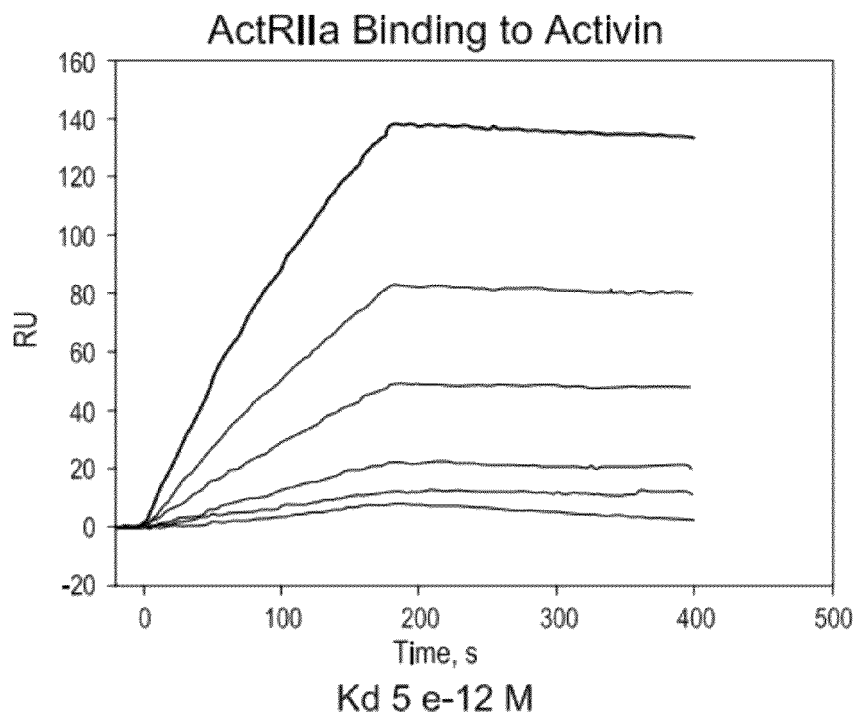
FIG. 2 shows the binding of ActRIIa-hFc to activin and GDF-11, as measured by BiaCore™ assay.
Figure 2:
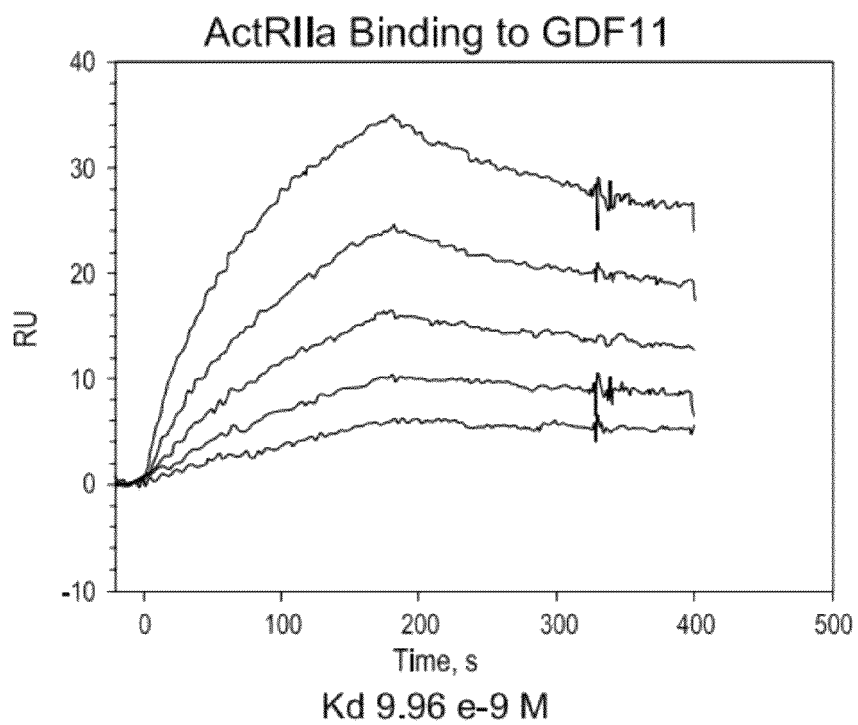

ActRIIa-hFc and ActRIIa-mFc showed a high affinity for ligands, particularly activin A. GDF-11 or Activin A ("ActA") were immobilized on a Biacore CM5 chip using standard amine coupling procedure. ActRIIa-hFc and ActRIIa-mFc proteins were loaded onto the system, and binding was measured. ActRIIa-hFc bound to activin with a dissociation constant ($K_D$) of $5 \times 10^{-12}$, and the protein bound to GDF11 with a $K_D$ of $9.96 \times 10^{-9}$. See FIG. 2. ActRIIa-mFc behaved similarly.

Figure 3:
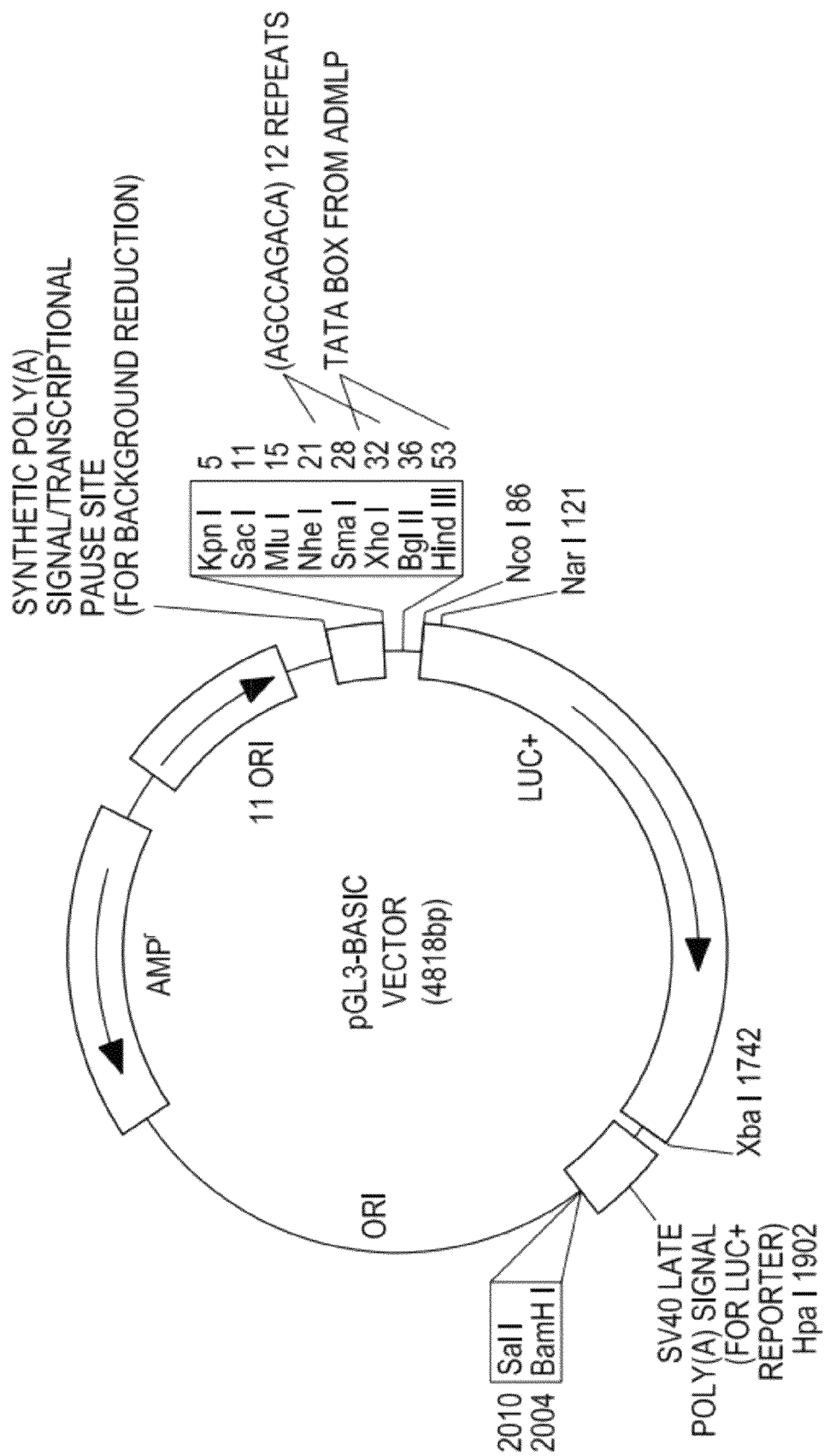
FIG. 3 shows a schematic for the A-204 Reporter Gene Assay. The figure shows the Reporter vector: pGL3(CAGA) 12 (described in Dennler et al, 1998, EMBO 17: 3091-3100.) The CAGA12 motif is present in TGF-Beta responsive genes (PAI-1 gene), so this vector is of general use for factors signaling through Smad 2 and 3.

An A-204 Reporter Gene Assay was used to evaluate the effects of ActRIIa-hFc proteins on signaling by GDF-11 and Activin A. Cell line: Human Rhabdomyosarcoma (derived from muscle). Reporter vector: pGL3(CAGA)12 (Described in Dennler et al, 1998, EMBO 17: 3091-3100.) See FIG. 3. The CAGA12 motif is present in TGF-Beta responsive genes (PAI-1 gene), so this vector is of general use for factors signaling through Smad2 and 3.

Day 1: Split A-204 cells into 48-well plate.

Day 2: A-204 cells transfected with 10 μg pGL3(CAGA)12 or pGL3(CAGA)12 (10 μg)+pRLCMV (1 μg) and Fugene.

Day 3: Add factors (diluted into medium+0.1% BSA). Inhibitors need to be preincubated with Factors for 1 hr before adding to cells. 6 hrs later, cells rinsed with PBS, and lyse cells.

This is followed by a Luciferase assay. Typically in this assay, in the absence of any inhibitors, Activin A shows roughly 10 fold stimulation of reporter gene expression and an ED50~2 ng/ml. GDF-11: 16 fold stimulation, ED50: ~1.5 ng/ml. GDF-8 shows an effect similar to GDF-11.

Figure 4:
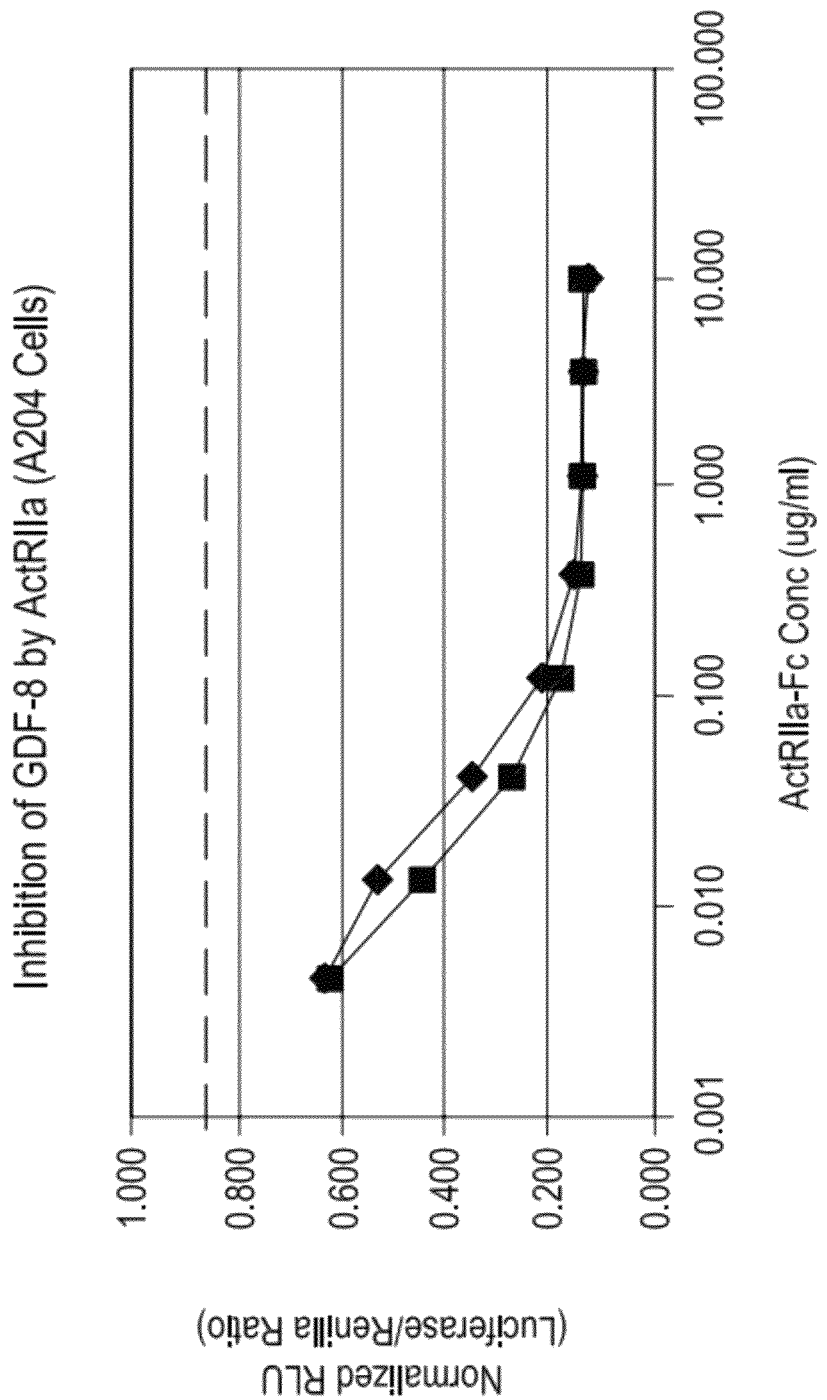
FIG. 4 shows the effects of ActRIIa-hFc (diamonds) and ActRIIa-mFc (squares) on GDF-8 signaling in the A-204 Reporter Gene Assay. Both proteins exhibited substantial inhibition of GDF-8 mediated signaling at picomolar concentrations.
Figure 5:
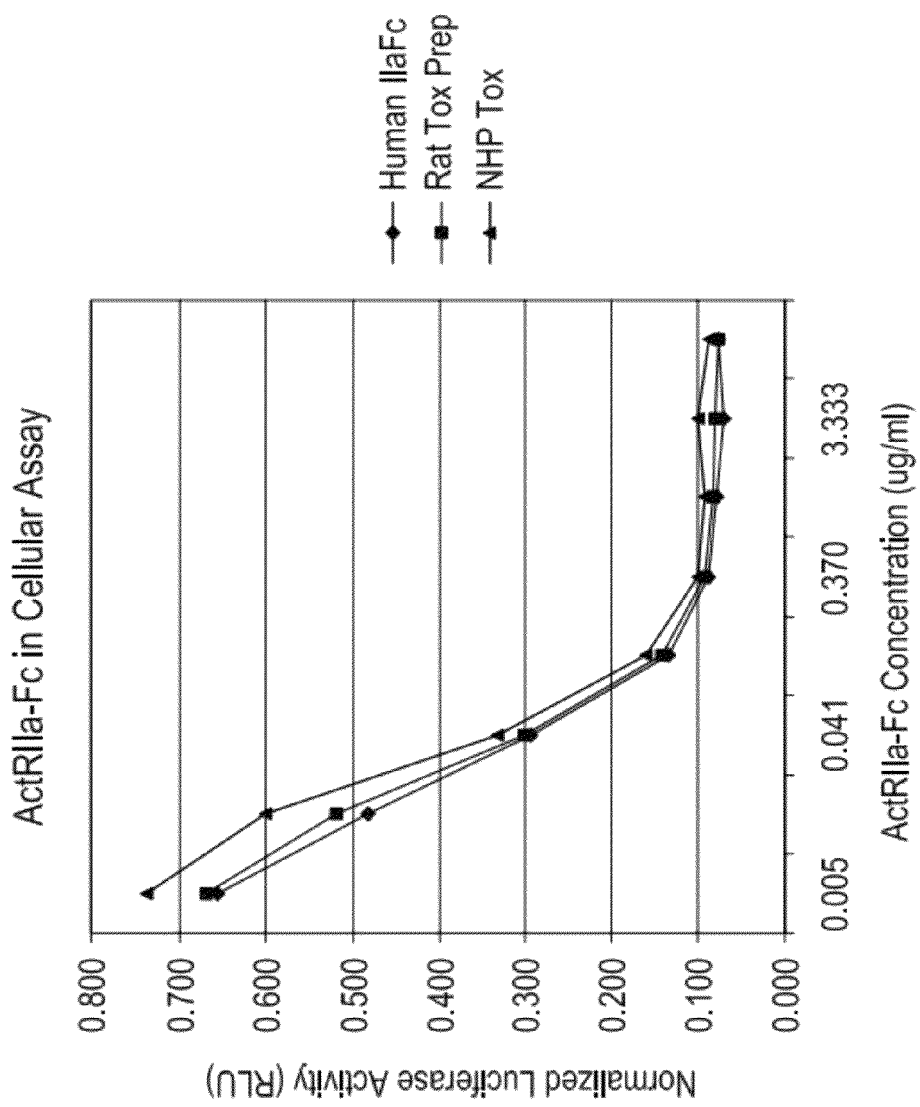
FIG. 5 shows the effects of three different preparations of ActRIIa-hFc on GDF-11 signaling in the A-204 Reporter Gene Assay.

As shown in FIG. 4, ActRIIa-hFc and ActRIIa-mFc inhibit GDF-8 mediated signaling at picomolar concentrations. As shown in FIG. 5, three different preparations of ActRIIa-hFc inhibited GDF-11 signaling with an IC50 of approximately 200 pM.

The ActRIIa-hFc was very stable in pharmacokinetic studies. Rats were dosed with 1 mg/kg, 3 mg/kg or 10 mg/kg of ActRIIa-hFc protein and plasma levels of the protein were measured at 24, 48, 72, 144 and 168 hours. In a separate study, rats were dosed at 1 mg/kg, 10 mg/kg or 30 mg/kg. In rats, ActRIIa-hFc had an 11-14 day serum half life and circulating levels of the drug were quite high after two weeks (11 μg/ml, 110 μg/ml or 304 μg/ml for initial administrations of 1 mg/kg, 10 mg/kg or 30 mg/kg, respectively.) In cynomolgus monkeys, the plasma half life was substantially greater than 14 days and circulating levels of the drug were 25 μg/ml, 304 μg/ml or 1440 μg/ml for initial administrations of 1 mg/kg, 10 mg/kg or 30 mg/kg, respectively. Preliminary results in humans suggests that the serum half life is between about 20 and 30 days.

Example 2

ActRIIa-mFc Promotes Bone Growth In Vivo

Figure 6:
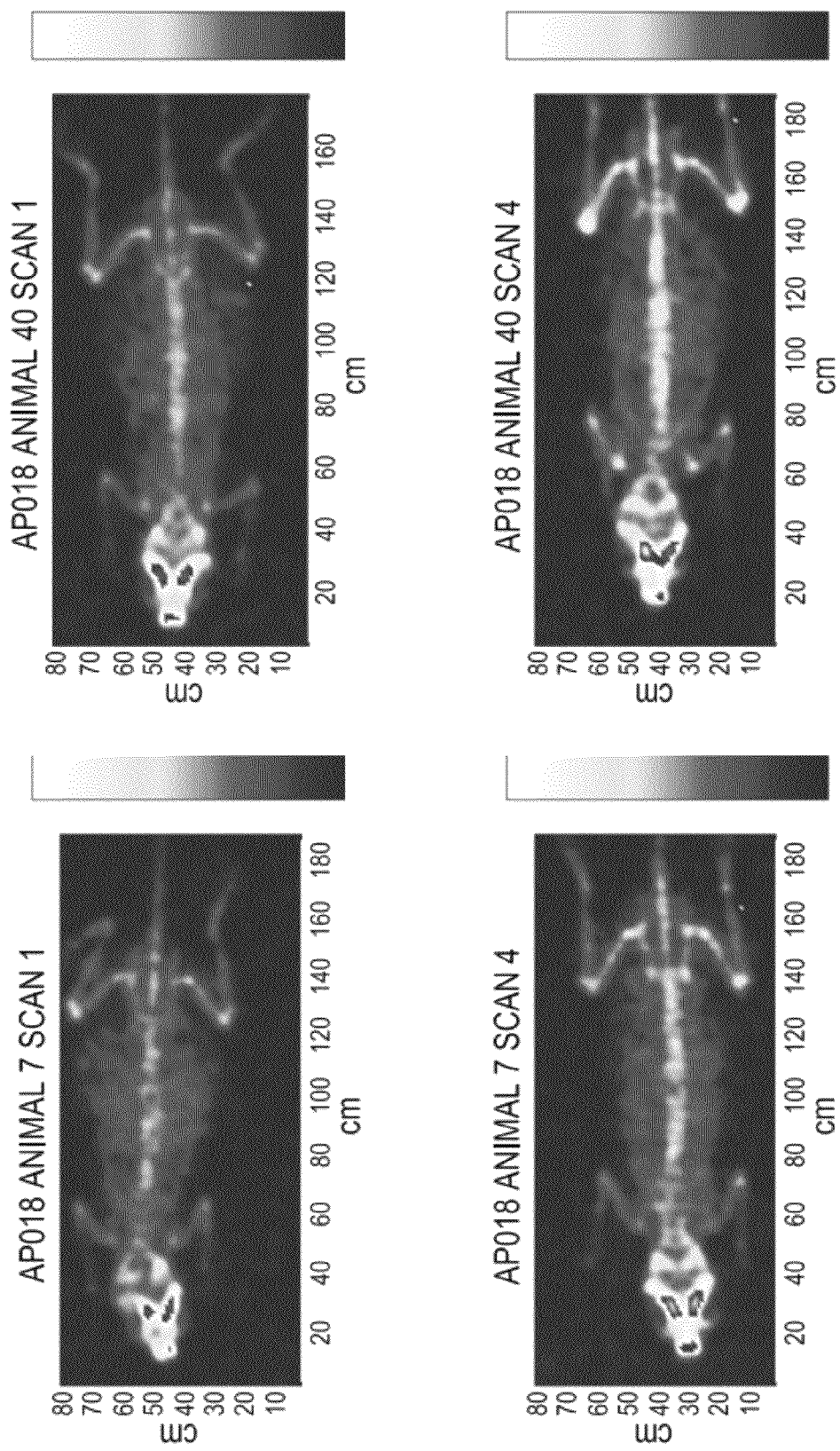
FIG. 6 shows examples of DEXA images of control- and ActRIIa-mFc-treated BALB/c mice, before (top panels) and after (bottom panels) the 12-week treatment period. Paler shading indicates increased bone density.

Normal female mice (BALB/c) were dosed with ActRIIa-mFc at a level of 1 mg/kg/dose, 3 mg/kg/dose or 10 mg/kg/dose, with doses given twice weekly. Bone mineral density and bone mineral content were determined by DEXA, see FIG. 6.

Figure 7:
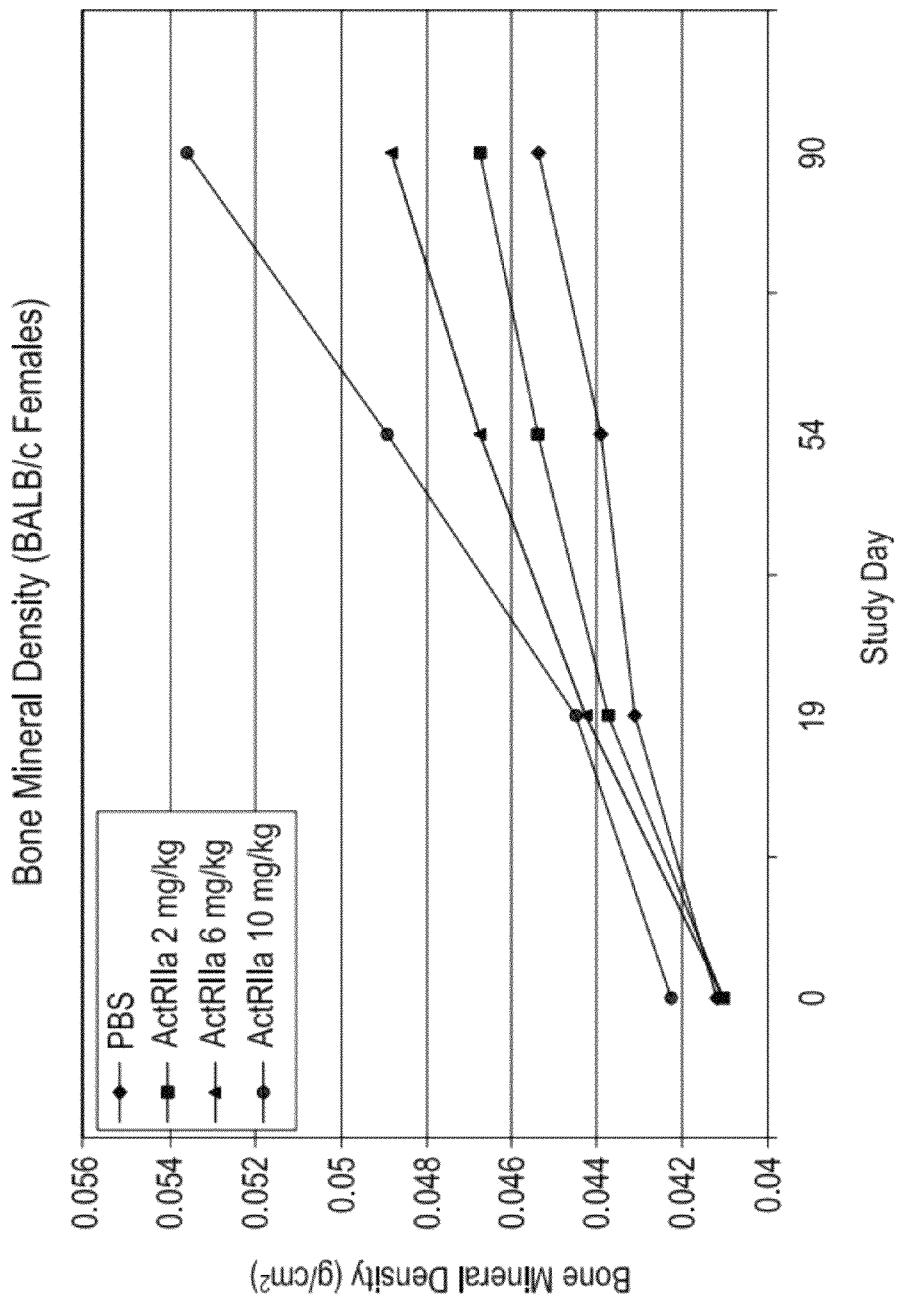
FIG. 7 shows a quantification of the effects of ActRIIa-mFc on bone mineral density in BALB/c mice over the 12-week period. Treatments were control (diamonds), 2 mg/kg dosing of ActRIIa-mFc (squares), 6 mg/kg dosing of ActRIIa-mFc (triangles) and 10 mg/kg dosing of ActRIIa-mFc (circles).
Figure 8:
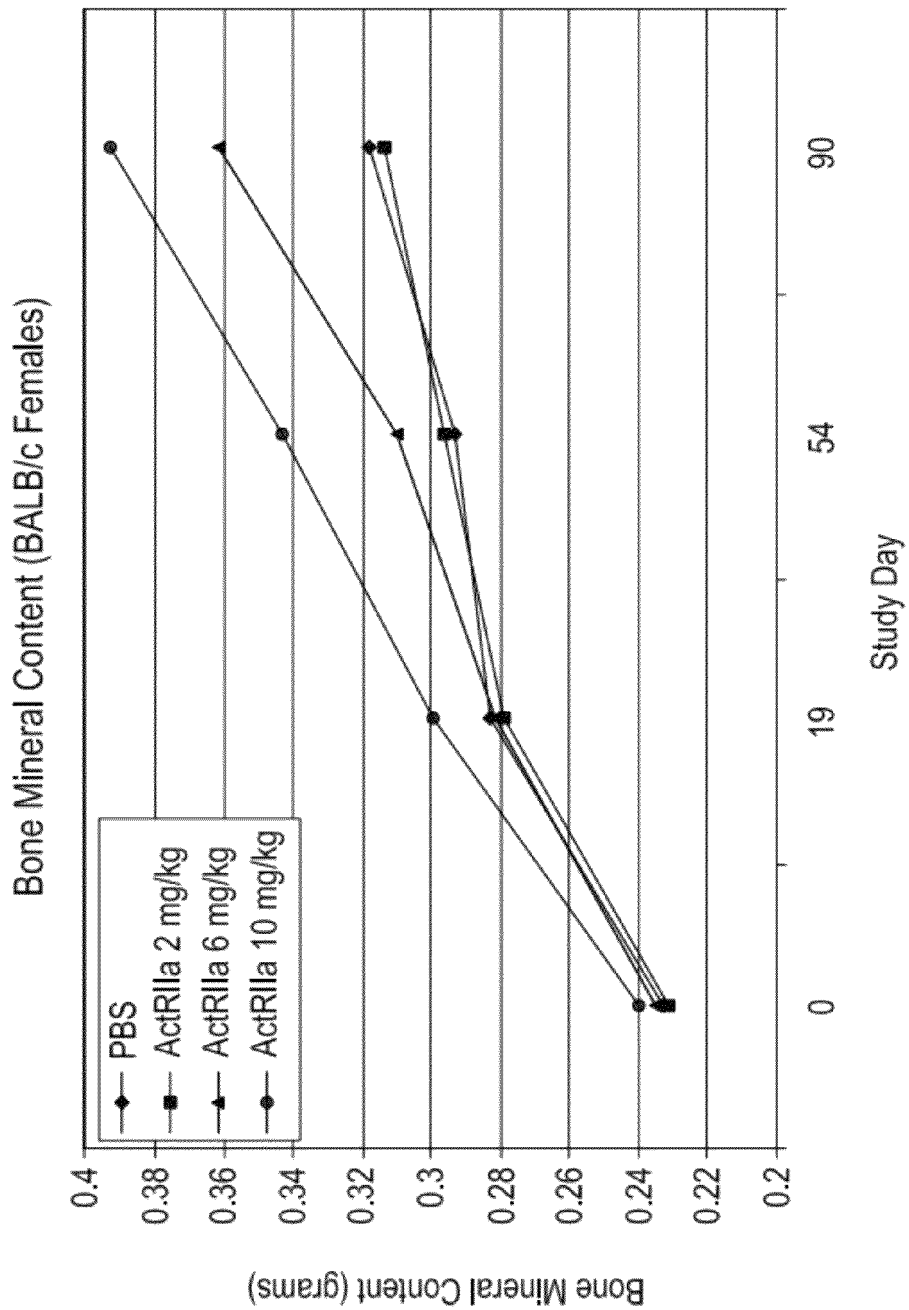
FIG. 8 shows a quantification of the effects of ActRIIa-mFc on bone mineral content in BALB/c mice over the 12-week period. Treatments were control (diamonds), 2 mg/kg dosing of ActRIIa-mFc (squares), 6 mg/kg dosing of ActRIIa-mFc (triangles) and 10 mg/kg dosing of ActRIIa-mFc (circles).

In BALB/c female mice, DEXA scans showed a significant increase (>20%) in bone mineral density and content as a result of ActRIIa-mFc treatment. See FIGS. 7 and 8.

Thus, antagonism of ActRIIa caused increased bone density and content in normal female mice. As a next step, the effect of ActRIIa-mFc on bone in a mouse model for osteoporosis was tested.

Andersson et al. (2001), established that ovariectomized mice suffered substantial bone loss (rougly 50% loss of trabecular bone six weeks post-operation), and that bone loss in these mice could be corrected with candidate therapeutic agents, such as parathyroid hormone.

Applicants used C57BL6 female mice that were ovariectomized (OVX) or sham operated at 4-5 weeks of age. Eight weeks after surgery, treatment with ActRIIa-mFc (10 mg/kg, twice weekly) or control (PBS) was initiated. Bone density was measured by CT scanner.

Figure 9:
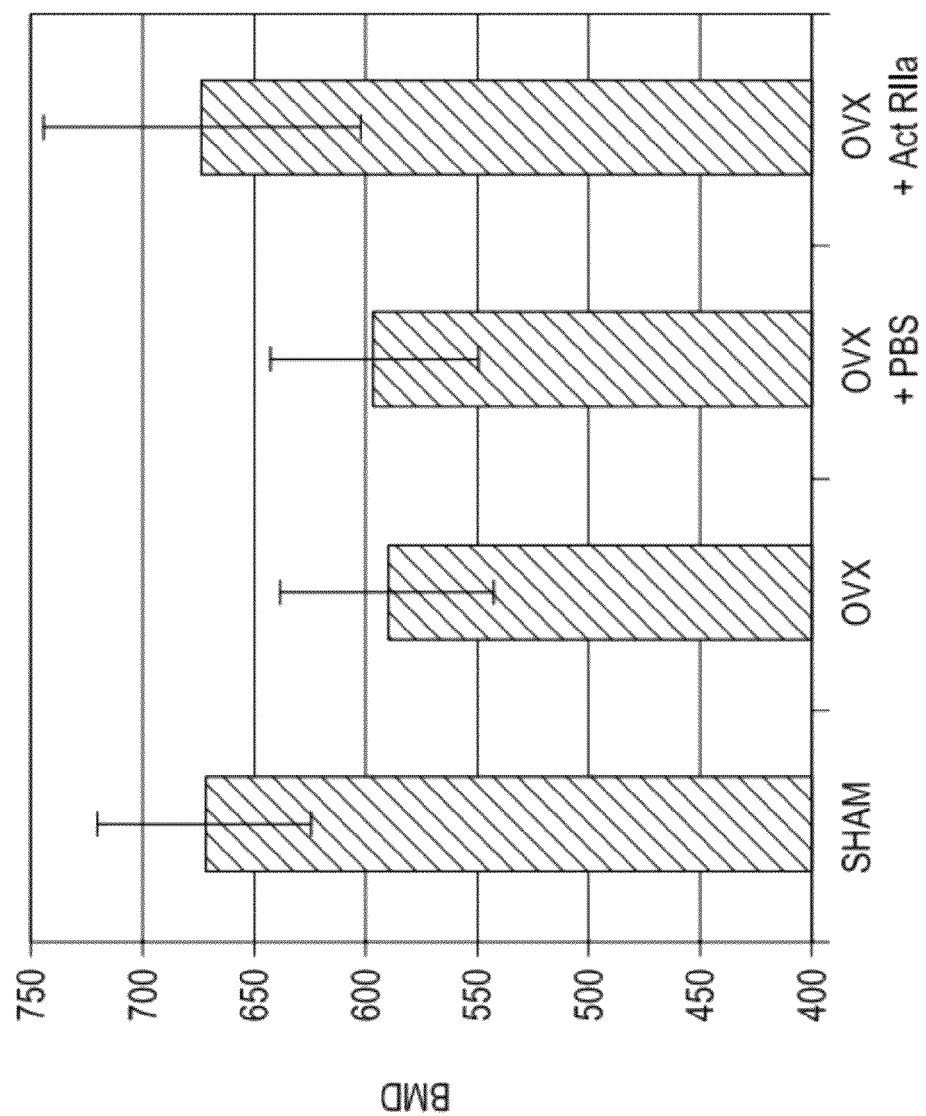
FIG. 9 shows a quantification of the effects of ActRIIa-mFc on bone mineral density of the trabecular bone in ovariectomized (OVX) or sham operated (SHAM) C57BL6 mice over after a 6-week period. Treatments were control (PBS) or 10 mg/kg dosing of ActRIIa-mFc (ActRIIa).
Figure 10:
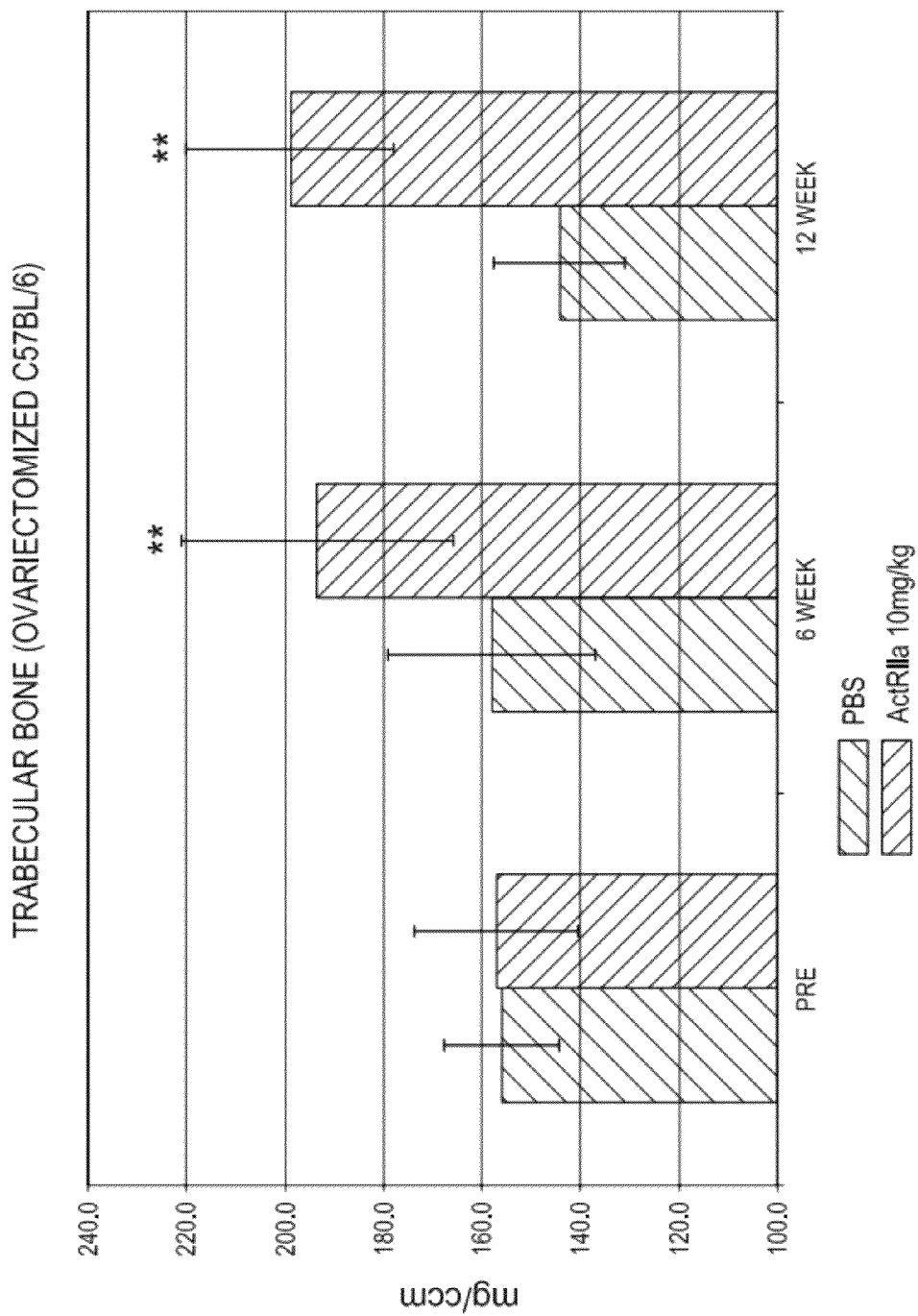
FIG. 10 shows a quantification of the effects of ActRIIa-mFc on the trabecular bone in ovariectomized (OVX) C57BL6 mice over a 12-week period. Treatments were control (PBS; pale bars) or 10 mg/kg dosing of ActRIIa-mFc (ActRIIa; dark bars).

As shown in FIG. 9, untreated, ovariectomized mice showed substantial loss of trabecular bone density relative to the sham controls after six weeks. ActRIIa-mFc treatment restored bone density to the level of the sham operated mice. At 6 and 12 weeks of the treatment, ActRIIa-mFc caused substantial increase in trabecular bone of OVX mice. See FIG. 10. After 6 weeks of treatment, bone density increased by 24% relative to PBS controls. After 12 weeks, the increase was 27%.

Figure 11:
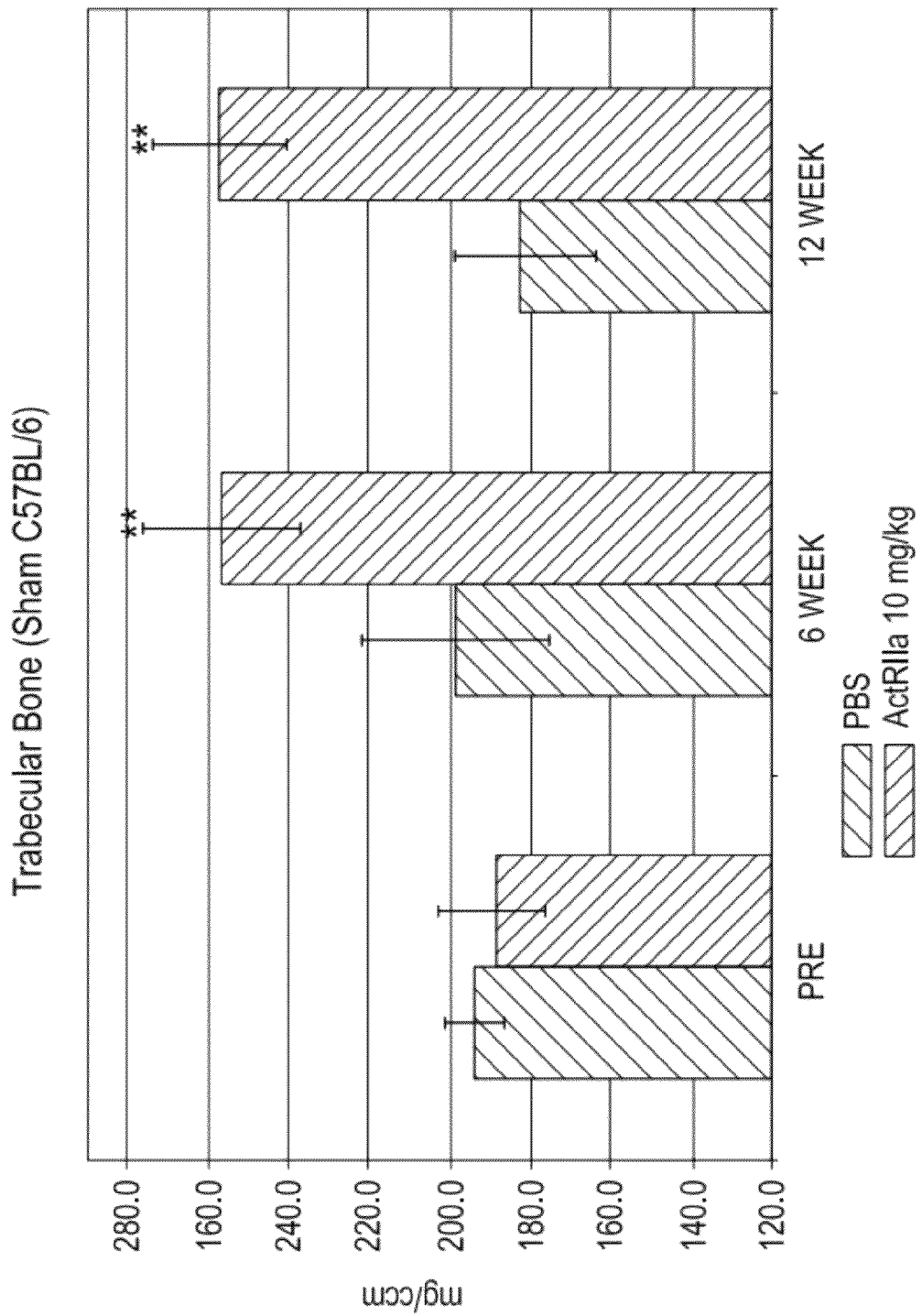
FIG. 11 shows a quantification of the effects of ActRIIa-mFc on the trabecular bone in sham operated C57BL6 mice after 6 or 12 weeks of treatment period. Treatments were control (PBS; pale bars) or 10 mg/kg dosing of ActRIIa-mFc (ActRIIa; dark bars).

In the sham operated mice, ActRIIa-mFc also caused a substantial increase in trabecular bone. See FIG. 11. After 6 and 12 weeks, the treatment produced a 35% increase relative to controls.

Figure 12:
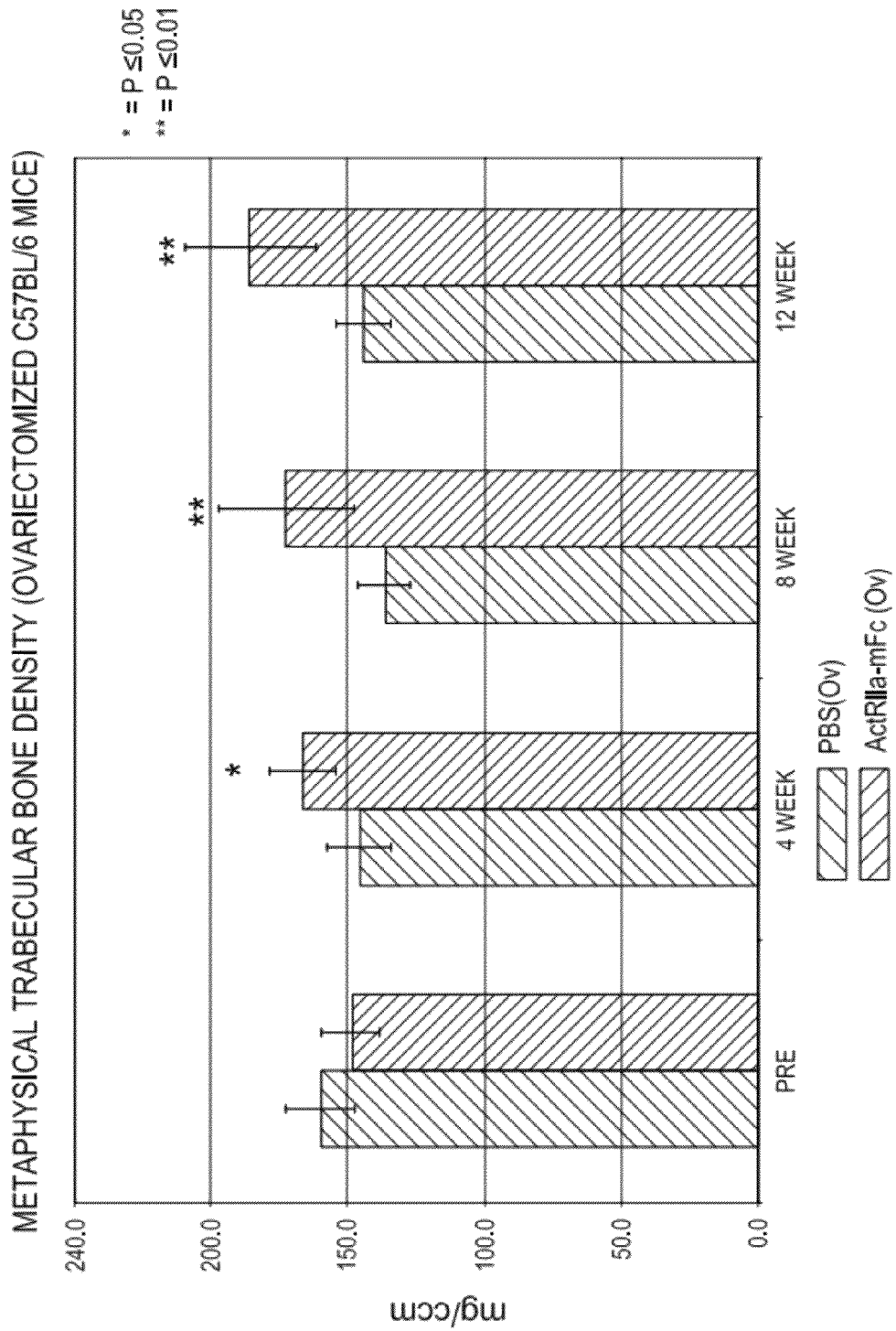
FIG. 12 shows the results of pQCT analysis of bone density in ovariectomized mice over 12 weeks of treatment. Treatments were control (PBS; pale bars) or ActRIIa-mFc (dark bars). y-axis: mg/ccm
Figure 13:
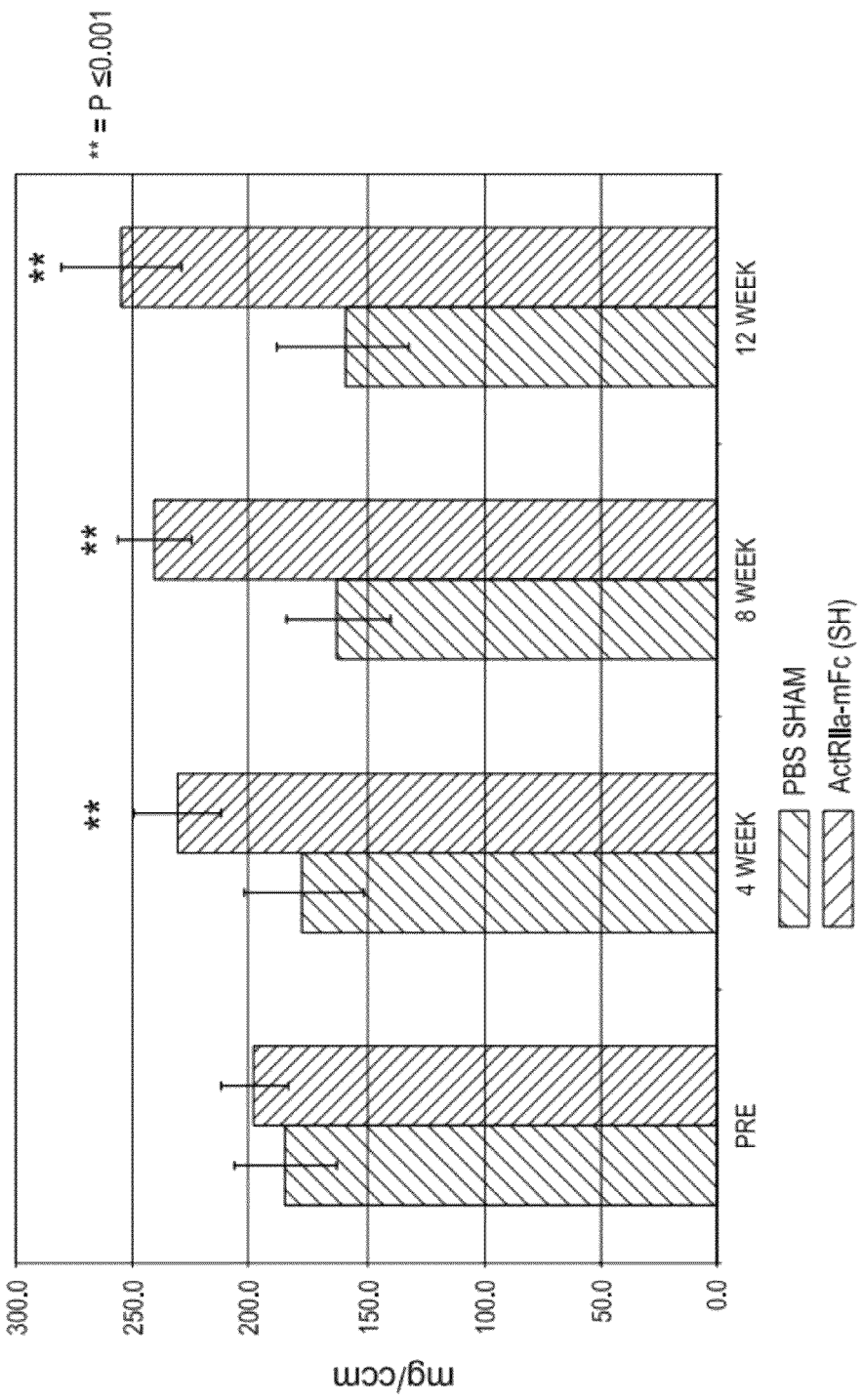
FIG. 13 depicts the results of pQCT analysis of bone density in sham operated mice over 12 weeks of treatment. Treatments were control (PBS; pale bars) or ActRIIa-mFc (dark bars). y-axis: mg/ccm

In an additional set of experiments, ovariectomized (OVX) or sham operated mice as described above were treated with ActRIIa-mFc (10 mg/kg, twice weekly) or control (PBS) over twelve weeks. Similar to the results described above for ActRIIa-mFc, OVX mice receiving ActRIIa-mFc exhibited an increase in trabecular bone density of 15% by as early as four weeks and 25% after 12 weeks of treatment (FIG. 12). Sham operated mice receiving ActRIIa-mFc similarly showed an increase in trabecular bone density of 22% by as early as four weeks and of 32% after 12 weeks of treatment (FIG. 13).

Figure 14B:
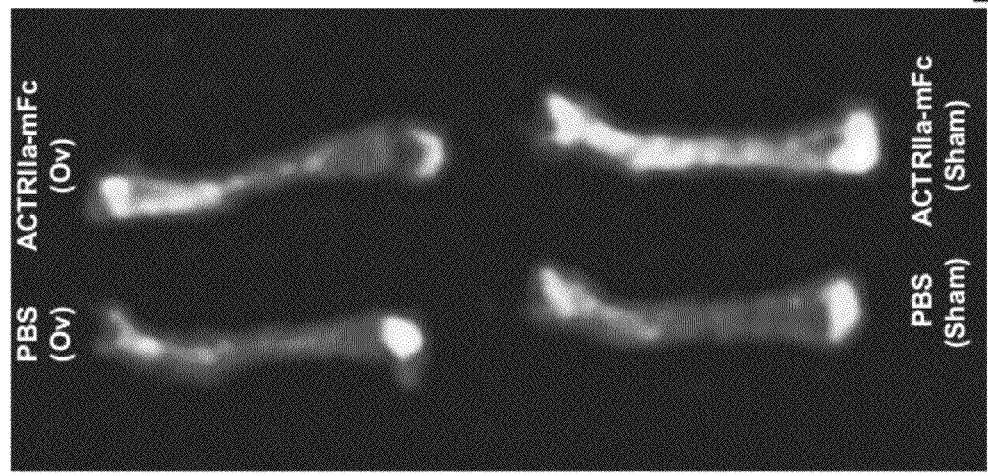
FIGS. 14A and 14B show whole body DEXA analysis after 12 weeks of treatment (A) and ex vivo analysis of femurs (B). Light areas depict areas of high bone density.
Figure 14A:
Figure 14A:
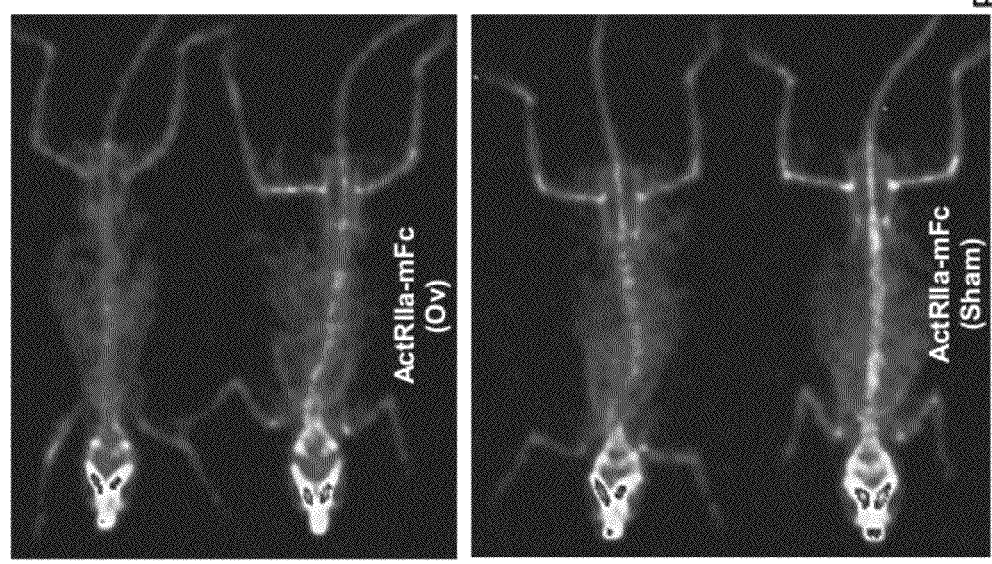
Figure 15:
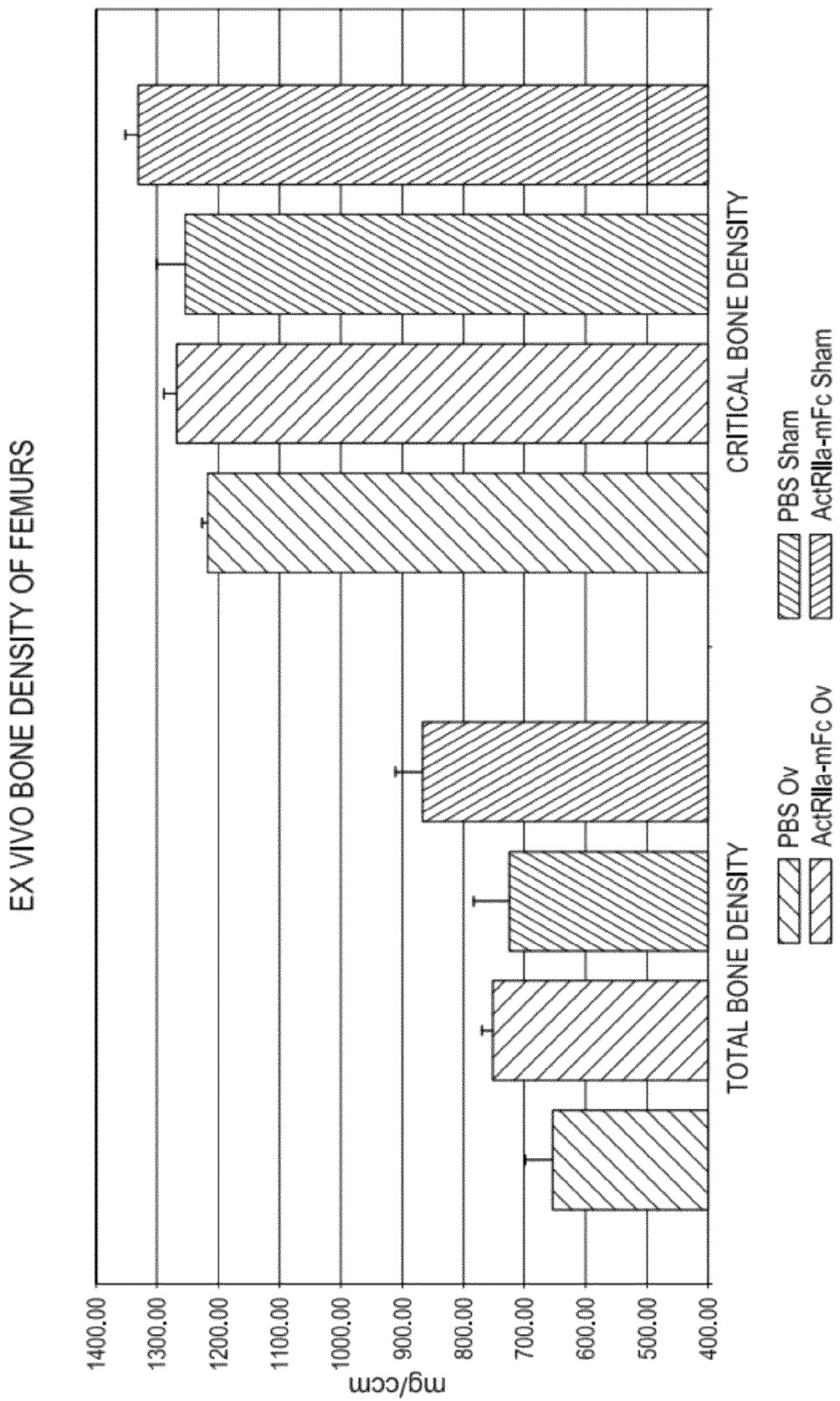
FIG. 15 shows ex vivo pQCT analysis of the femoral midshaft after twelve weeks of treatment. Treatments were vehicle control (PBS, dark bars) and ActRIIa-mFc (pale bars). The four bars to the left show total bone density while the four bars to the right show cortical bone density. The first pair of bars in each set of four bars represent data from ovariectomized mice while the second pair of bars represent data from sham operated mice.
Figure 16:
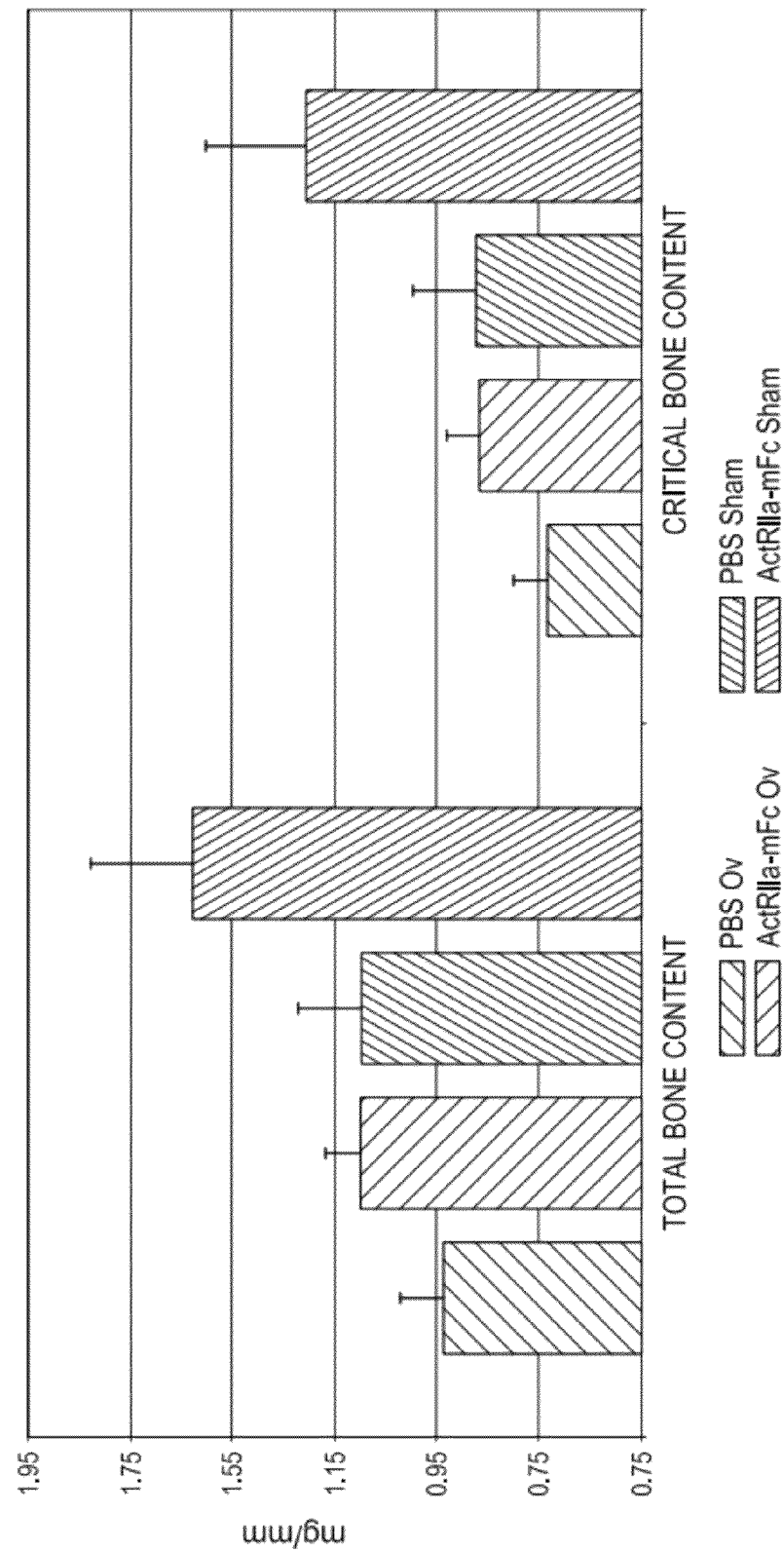
FIG. 16 shows ex vivo pQCT analysis and diaphyseal bone content of the femoral midshaft after twelve weeks of treatment. Treatments were vehicle control (PBS, dark bars) or ActRIIa-mFc (pale bars). The four bars to the left show total bone content while the four bars to the right show cortical bone content. The first pair of bars in each set of four bars represent data from ovariectomized mice while the second pair of bars represent data from sham operated mice.
Figure 17:
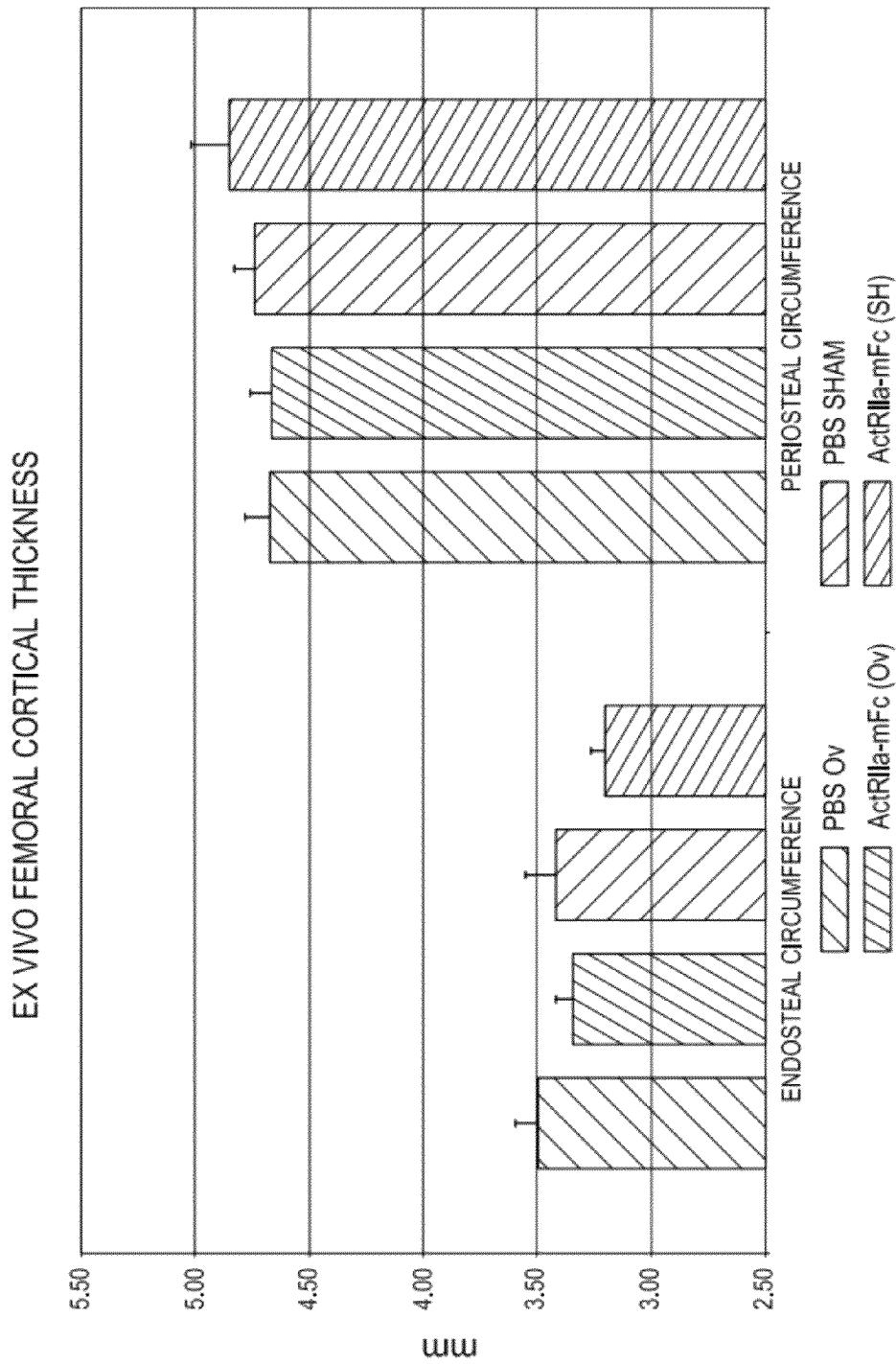
FIG. 17 shows ex vivo pQCT analysis of the femoral midshaft and femoral cortical thickness. Treatments were control (PBS, dark bars) and ActRIIa-mFc (pale bars). The four bars to the left show endosteal circumference while the four bars to the right show periosteal circumference. The first pair of bars in each set of four bars represent data from ovariectomized mice while the second pair of bars represent data from sham operated mice.

After twelve weeks of treatment with ActRIIa-mFc, whole body and ex vivo femur DEXA analysis showed that treatment induces an increase in bone density in both ovariectomized and sham operated mice (FIGS. 14A and 14B, respectively). These results are also supported by ex vivo pQCT analysis of the femoral midshaft which demonstrated a significant increase in both total and cortical bone density after twelve weeks of treatment with ActRIIa-mFc. Vehicle-treated control ovariectomized mice exhibited bone densities that were comparable to vehicle-treated control sham operated mice (FIG. 15). In addition to bone density, bone content increased following ActRIIa-mFC treatment. Ex vivo pQCT analysis of the femoral midshaft demonstrated a significant increase in both total and cortical bone content after twelve weeks of treatment with ActRIIa-mFc while both ovariectomized and sham operated vehicle control-treated mice exhibited comparable bone content (FIG. 16). Ex vivo pQCT analysis of the femoral midshaft also showed that ActRIIa-mFc treated mice did not show a change in periosteal circumference; however ActRIIa-mFc treatment resulted in a decrease in endosteal circumference indicating an increase in cortical thickness due to growth on the inner surface of the femur (FIG. 17).

Figure 18:
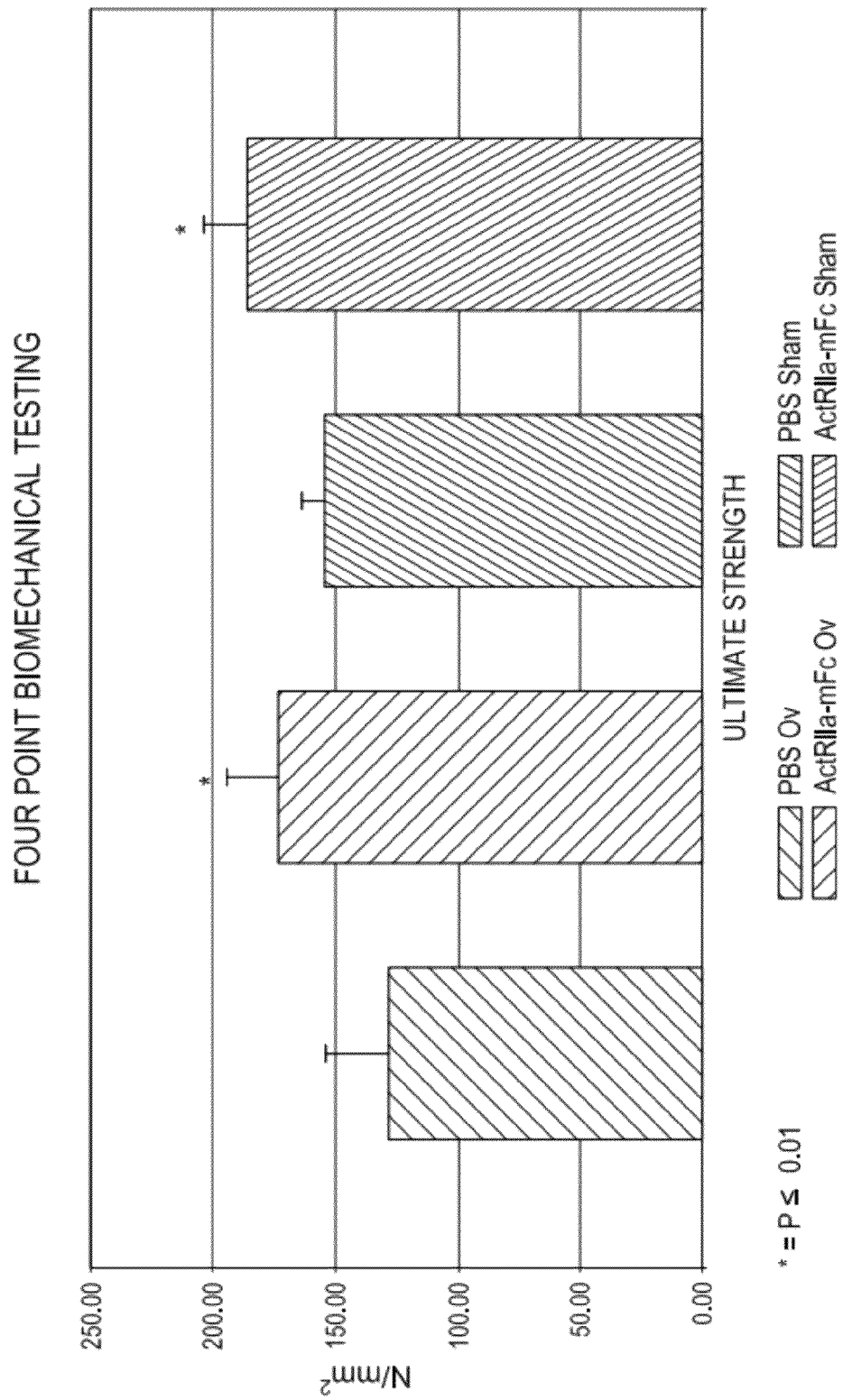
FIG. 18 depicts the results of mechanical testing of femurs after twelve weeks of treatment. Treatments were control (PBS, dark bars) and ActRIIa-mFc (pale bars). The two bars to the left represent data from ovariectomized mice while the last two bars represent data from sham operated mice.

Mechanical testing of femurs determined that ActRIIa-mFc was able to increase the extrinsic characteristics of the bone (maximal load, stiffness and energy to break) which contributed to a significant increase in the intrinsic properties (ultimate strength) of the bones. Ovariectomized mice treated with ActRIIa-mFc exhibited increased bone strength to levels beyond sham operated, vehicle treated controls, indicating a complete reversal of the osteoporotic phenotype (FIG. 18).

These data demonstrate that an activin-ActRIIa antagonist can increase bone density in normal female mice and, furthermore, correct defects in bone density, bone content, and ultimately bone strength, in a mouse model of osteoporosis.

Figure 19:
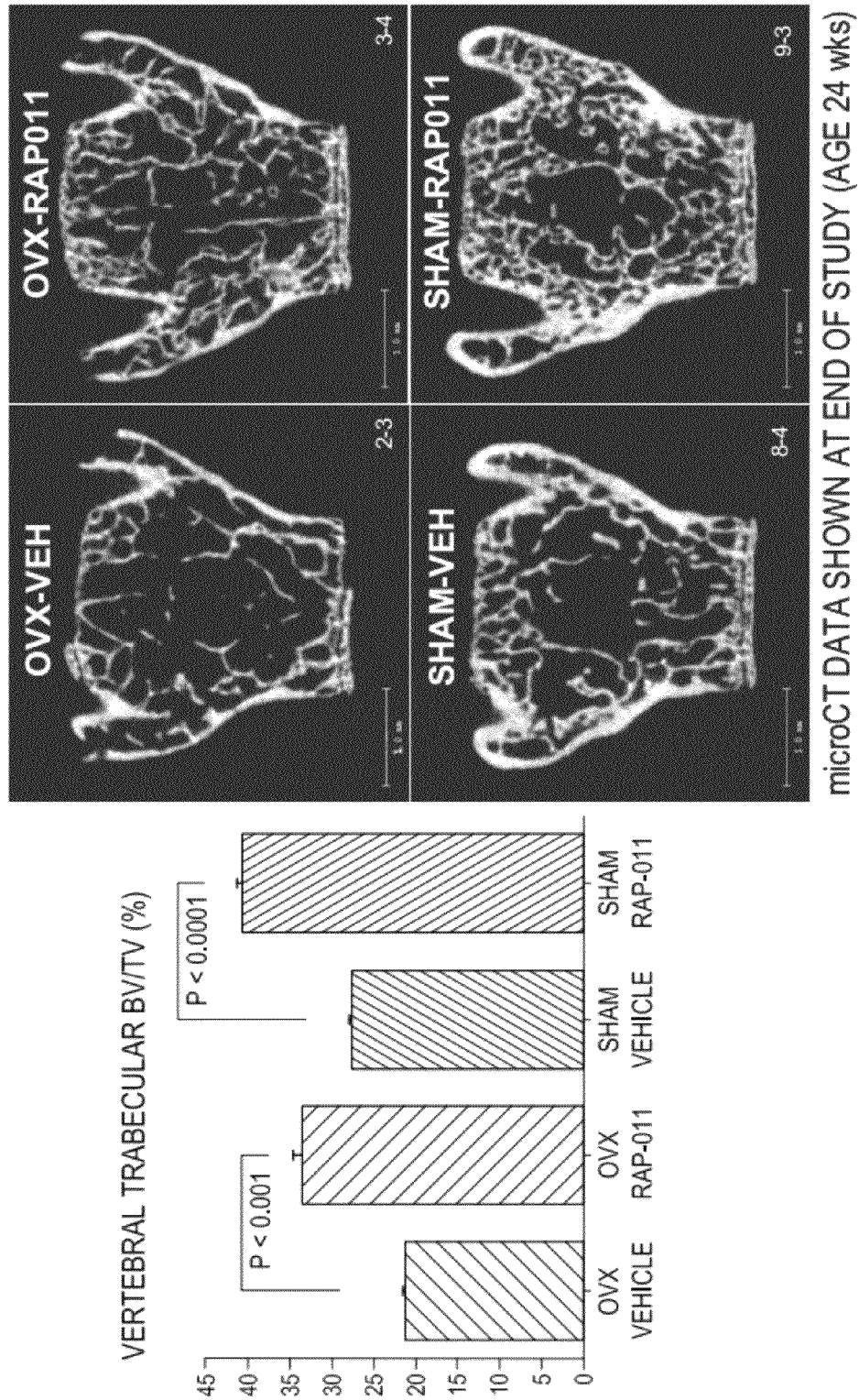
FIG. 19 shows the effects of ActrIIa-mFc on trabecular bone volume.
Figure 21:
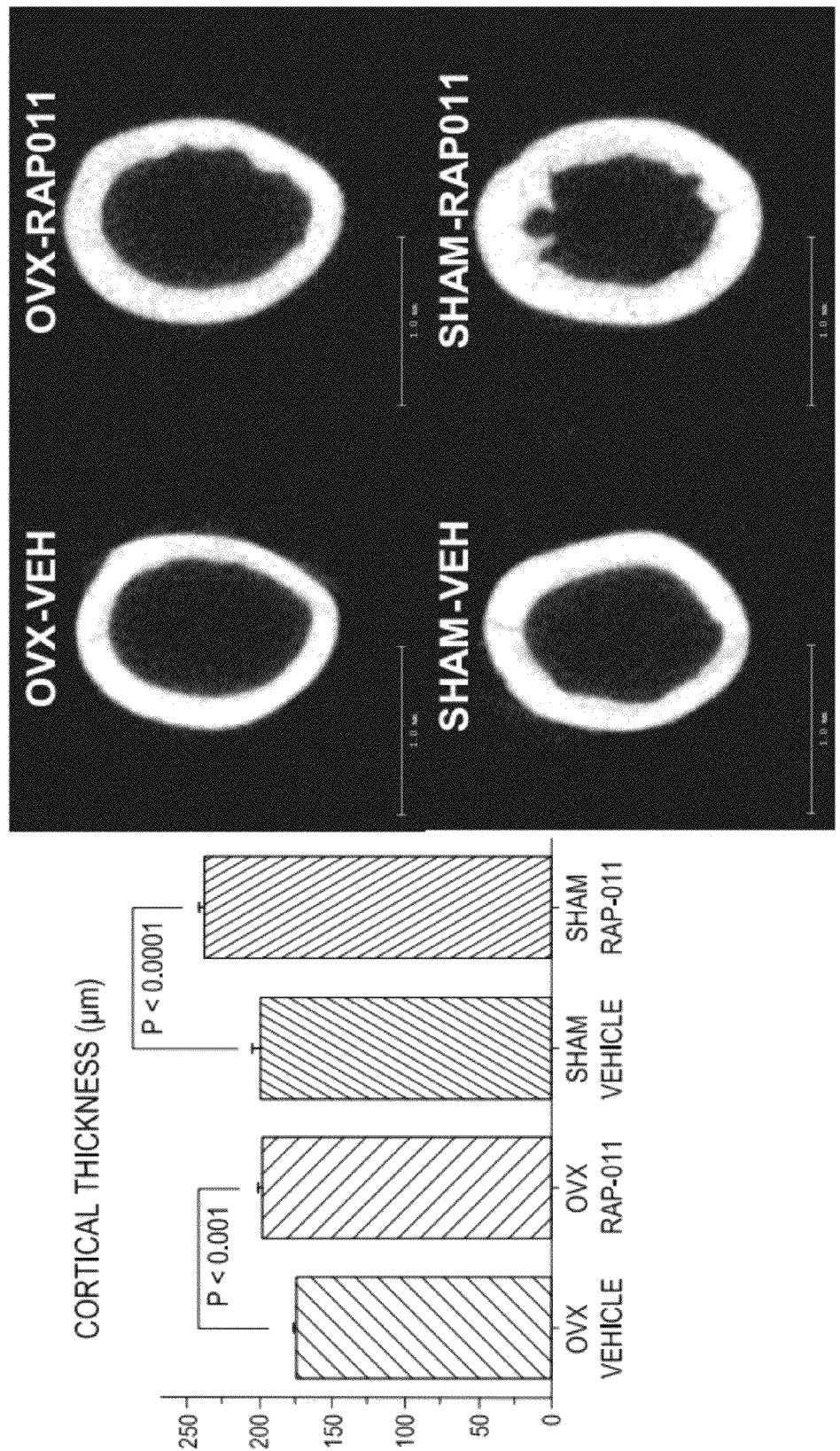
FIG. 21 shows the effects of ActrIIa-mFc on cortical bone.
Figure 22:
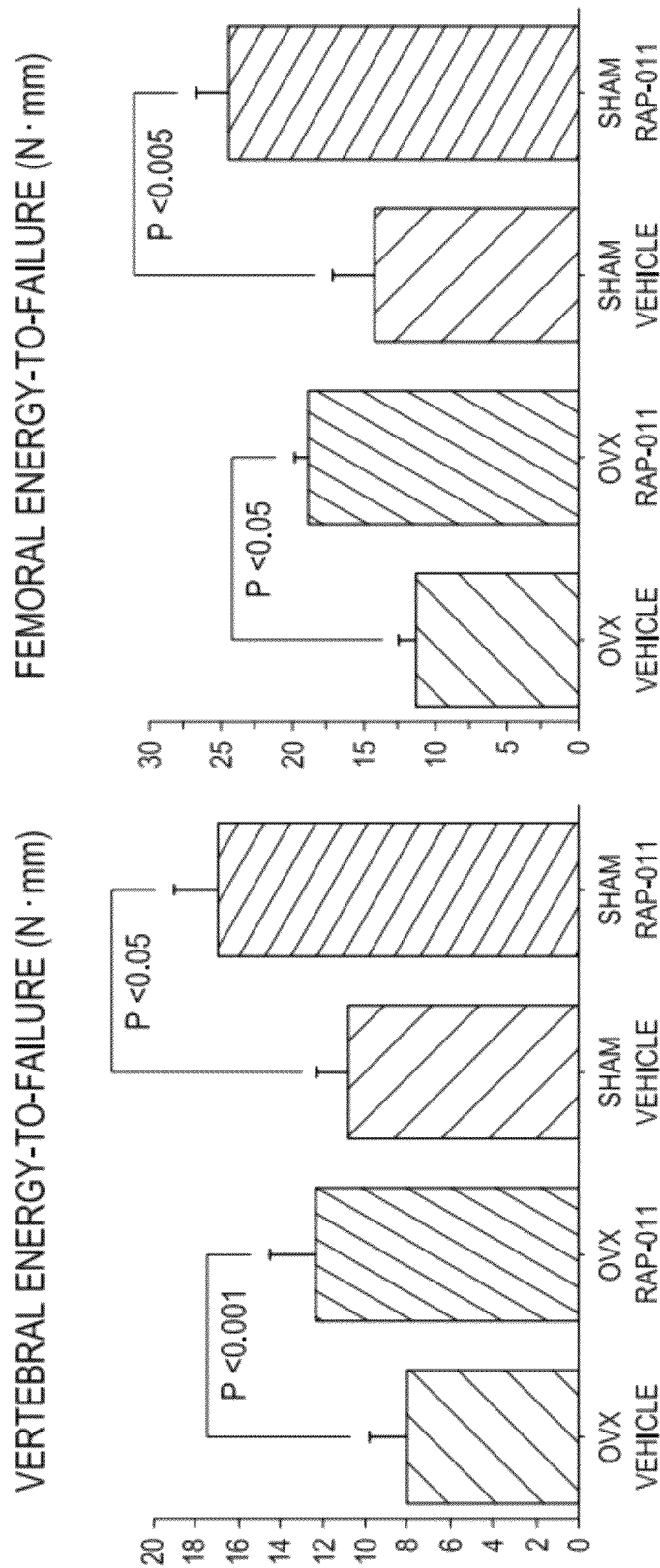
FIG. 22 shows the effects of ActrIIa-mFc on the mechanical strength of bone.
Figure 23:
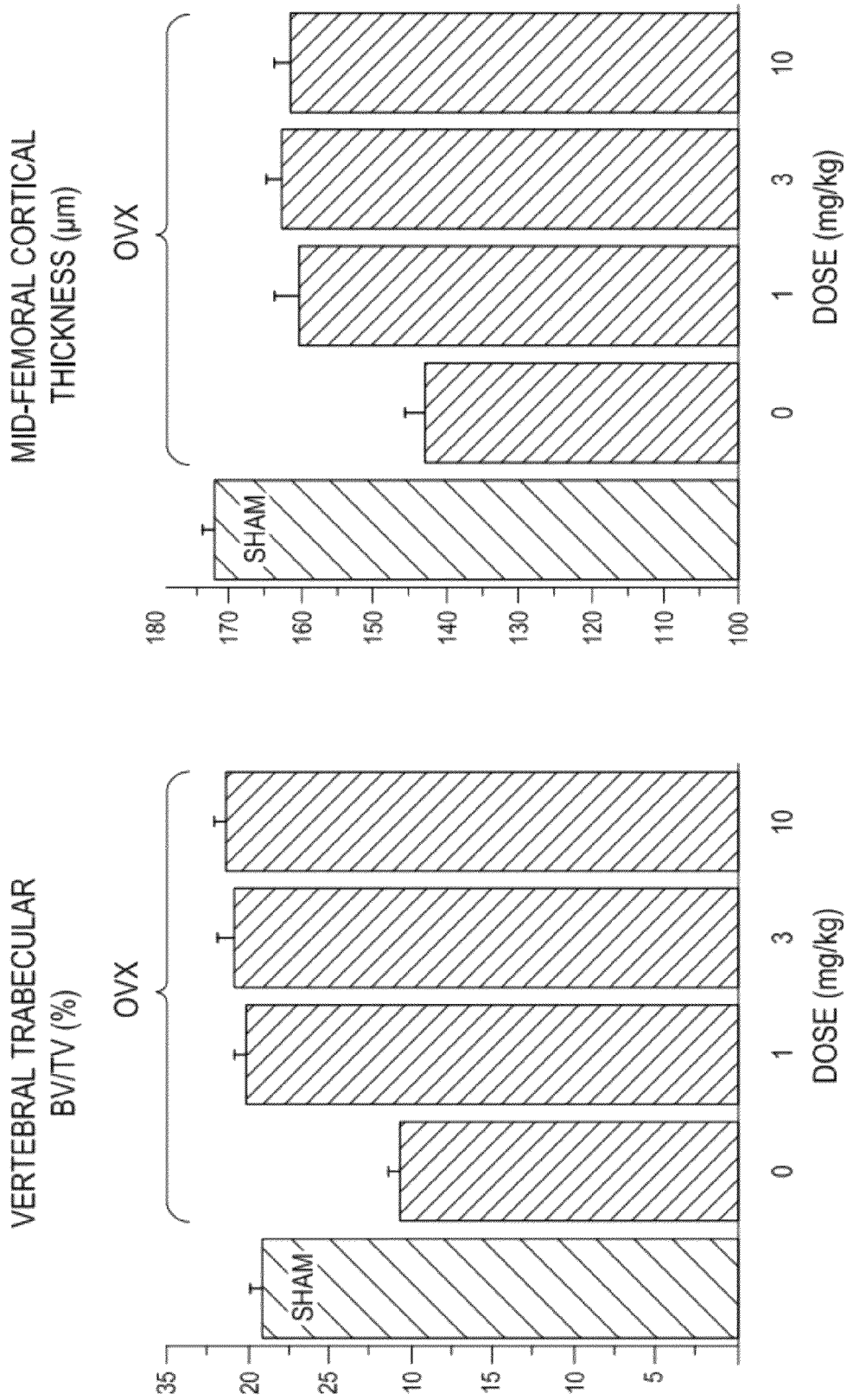
FIG. 23 shows the effects of different doses of ActRIIa-mFc on bone characteristics at three different dosages.

In a further set of experiments, mice were ovariectomized or sham operated at 4 weeks, and beginning at 12 weeks received either placebo or ActRIIa-mFc (2 times/week, 10 mg/kg) (also referred to as RAP-11 in FIGS. 19-24), for a further period of 12 weeks. A variety of bone parameters were evaluated. As shown in FIG. 19, ActRIIa-mFc increased vertebral trabecular bone volume to total volume ratios (BV/TV) in both the OVX and SHAM operated mice. ActRIIa-mFc also improved the trabecular architecture (FIG. 20), increased cortical thickness (FIG. 21) and improved bone strength (FIG. 22). As shown in FIG. 23, ActRIIa-mFc produced desirable effects at a range of doses from 1 mg/kg to 10 mg/kg.

Bone histomorphometry was conducted at a 2 week time point in sham operated mice. These data, presented in FIG. 24, demonstrate that ActRIIa-mFc has a dual effect, both inhibiting bone resorption and promoting bone growth. Thus ActRIIa-mFc stimulates bone growth (anabolic effect) and inhibits bone resorption (anti-catabolic effect).

Example 4

Alternative ActRIIa-Fc Proteins

An alternative construct may have a deletion of the C-terminal tail (the final 15 amino acids of the extracellular domain of ActRIIa. The sequence for such a construct is presented below (Fc portion underlined) (SEQ ID NO: 12):

```
ILGRSETQECLFFNANWEKDRTNQTGVEPCYGDKDKRRHCFATWKNIS
GSIEIVKQGCWLDDINCYDRTDCVEKKDSPEVYFCCCEGNMCNEKFSY
FPEMTGGGTHTCPPCPAPELLGGPSVFLFPPKPKDTLMISRTPEVTCV
VVDVSHEDPEVKFNWYVDGVEVHNAKTKPREEQYNSTYRVVSVLTVLH
QDWLNGKEYKCKVSNKALPVPIEKTISKAKGQPREPQVYTLPPSREEM
TKNQVSLTCLVKGFYPSDIAVEWESNGQPENNYKTTPPVLDSDGSFFL
YSKLTVDKSRWQQGNVFSCSVMHEALHNHYTQKSLSLSPGK
```

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating bone fractures, comprising administering to a subject in need thereof an effective amount of a polypeptide comprising an amino acid sequence that is at least 95% identical to SEQ ID NO: 2.

2. The method of claim 1, further comprising administering a second bone active-agent.

3. The method of claim 2, wherein the bone active-agent is selected from a bisphosphonate, an estrogen, a selective estrogen receptor modulator, a parathyroid hormone, a calcitonin, a calcium supplement, and a vitamin D supplement.

4. The method of claim 2, wherein the second bone active-agent is administered conjointly with the polypeptide.

5. The method of claims 4, wherein the polypeptide and the second bone active-agent are administered as a single co-formulation.

6. The method of claim 4, wherein the polypeptide and the second bone active-agent are administered simultaneously.

7. The method of claim 4, wherein the polypeptide and the second bone active-agent are administered at separate times.

8. The method of claim 1, wherein the polypeptide includes one or more modified amino acid residues selected from a glycosylated amino acid, a PEGylated amino acid, a farnesylated amino acid, an acetylated amino acid, a biotinylated amino acid, or an amino acid conjugated to a lipid moiety.

9. The method of claim 1, wherein the polypeptide is administered no more frequently than once per month.

10. The method of claim 1, wherein the polypeptide is administered no more frequently than once every three months.

11. The method of claim 1, wherein the polypeptide is administered no more frequently than once every six months.

12. The method of claim 1, wherein the polypeptide is at least 98% pure as determined by size-exclusion chromatography.

13. The method of claim 1, wherein the polypeptide comprises an amino acid sequence that is at least 97% identical to SEQ ID NO: 2.

14. The method of claim 1, wherein the polypeptide comprises an amino acid sequence that is at least 99% identical to SEQ ID NO: 2.

15. The method of claim 1, wherein the polypeptide comprises the amino acid sequence of SEQ ID NO: 2.

16. The method of claim 1, wherein the polypeptide is glycosylated and has a glycosylation pattern identical to a glycosylation pattern obtained by expressing the polypeptide in a Chinese hamster ovary (CHO) cell line.

17. The method of claim 1, wherein the N-terminus of the polypeptide is ILGRSETQE (SEQ ID NO: 11).

18. The method of claim 1, wherein the polypeptide further comprises a domain that enhances one or more of in vivo stability, in vivo half-life, uptake/administration, tissue localization or distribution, or formation of protein complexes.

19. The method of claim 18, wherein the domain is an immunoglobulin Fc domain.

20. The method of claim 18, wherein the domain is serum albumin.

21. The method of claim 1, wherein the serum half-life of the polypeptide is greater than two weeks.

22. The method of claim 1, wherein the serum half-life of the polypeptide is 20-30 days.

23. The method of claim 1, wherein the polypeptide has one or more of the following characteristics: (i) binds to an ActRIIa ligand with a $K_D$ of at least $10^{-7}$ M; and (ii) inhibits ActRIIa signaling.

24. The method of claim 1, wherein the polypeptide is soluble.

25. The method of claim 1, wherein the polypeptide is an antagonist of activin A.

26. The method of claim 1, wherein the polypeptide comprises an amino acid sequence that is at least 95% identical to SEQ ID NO: 7.

27. The method of claim 1, wherein the polypeptide comprises an amino acid sequence that is at least 97% identical to SEQ ID NO: 7.

28. The method of claim 1, wherein the polypeptide comprises an amino acid sequence that is at least 99% identical to SEQ ID NO: 7.

29. The method of claim 1, wherein the polypeptide comprises the amino acid sequence of SEQ ID NO: 7.

30. The method of claim 1, wherein the polypeptide binds to activin.

31. The method of claim 1, wherein the polypeptide is recombinantly expressed using a Tissue Plasminogen Activator (TPA) leader sequence.

32. The method of claim 31, wherein the TPA leader sequence comprises the amino acid sequence of SEQ ID NO:9.

33. A method for increasing bone strength, comprising administering to a subject in need thereof an effective amount of a polypeptide comprising an amino acid sequence that is at least 95% identical to SEQ ID NO: 2.

34. The method of claim 33, further comprising administering a second bone active-agent.

35. The method of claim 34, wherein the bone active-agent is selected from a bisphosphonate, an estrogen, a selective estrogen receptor modulator, a parathyroid hormone, a calcitonin, a calcium supplement, and a vitamin D supplement.

36. The method of claim 34, wherein the second bone active-agent is administered conjointly with the polypeptide.

37. The method of claims 34, wherein the polypeptide and the second bone active-agent are administered as a single co-formulation.

38. The method of claim 34, wherein the polypeptide and the second bone active-agent are administered simultaneously.

39. The method of claim 34, wherein the polypeptide and the second bone active-agent are administered at separate times.

40. The method of claim 33, wherein the polypeptide includes one or more modified amino acid residues selected from a glycosylated amino acid, a PEGylated amino acid, a farnesylated amino acid, an acetylated amino acid, a biotinylated amino acid, or an amino acid conjugated to a lipid moiety.

41. The method of claim 33, wherein the polypeptide is administered no more frequently than once per month.

42. The method of claim 33, wherein the polypeptide is administered no more frequently than once every three months.

43. The method of claim 33, wherein the polypeptide is administered no more frequently than once every six months.

44. The method of claim 33, wherein the polypeptide is at least 98% pure as determined by size-exclusion chromatography.

45. The method of claim 33, wherein the polypeptide comprises an amino acid sequence that is at least 97% identical to SEQ ID NO: 2.

46. The method of claim 33, wherein the polypeptide comprises an amino acid sequence that is at least 99% identical to SEQ ID NO: 2.

47. The method of claim 33, wherein the polypeptide comprises the amino acid sequence of SEQ ID NO: 2.

48. The method of claim 33, wherein the polypeptide is glycosylated and has a glycosylation pattern identical to a glycosylation pattern obtained by expressing the polypeptide in a Chinese hamster ovary (CHO) cell line.

49. The method of claim 33, wherein the N-terminus of the polypeptide is ILGRSETQE (SEQ ID NO: 11).

50. The method of claim 33, wherein the polypeptide further comprises a domain that enhances one or more of in vivo stability, in vivo half-life, uptake/administration, tissue localization or distribution, or formation of protein complexes.

51. The method of claim 50, wherein the domain is an immunoglobulin Fc domain.

52. The method of claim 50, wherein the domain is serum albumin.

53. The method of claim 33, wherein the serum half-life of the polypeptide is greater than two weeks.

54. The method of claim 33, wherein the serum half-life of the polypeptide is 20-30 days.

55. The method of claim 33, wherein the polypeptide has one or more of the following characteristics: (i) binds to an ActRIIa ligand with a $K_D$ of at least $10^{-7}$ M; and (ii) inhibits ActRIIa signaling.

56. The method of claim 33, wherein the polypeptide is soluble.

57. The method of claim 33, wherein the polypeptide binds to activin.

58. The method of claim 33, wherein the polypeptide is an antagonist of activin A.

59. The method of claim 33, wherein the polypeptide comprises an amino acid sequence that is at least 95% identical to SEQ ID NO: 7.

60. The method of claim 33, wherein the polypeptide comprises an amino acid sequence that is at least 97% identical to SEQ ID NO: 7.

61. The method of claim 33, wherein the polypeptide comprises an amino acid sequence that is at least 99% identical to SEQ ID NO: 7.

62. The method of claim 33, wherein the polypeptide comprises the amino acid sequence of SEQ ID NO: 7.

63. The method of claim 33, wherein the polypeptide is recombinantly expressed using a Tissue Plasminogen Activator (TPA) leader sequence.

64. The method of claim 63, wherein the TPA leader sequence comprises the amino acid sequence of SEQ ID NO:9.

65. A method for increasing bone mineral density comprising administering to a subject in need thereof an effective amount of a polypeptide comprising an amino acid sequence that is at least 95% identical to SEQ ID NO: 2.

66. The method of claim 65, further comprising administering a second bone active-agent.

67. The method of claim 66, wherein the bone-active agent is selected from a bisphosphonate, an estrogen, a selective estrogen receptor modulator, a parathyroid hormone, a calcitonin, a calcium supplement, and a vitamin D supplement.

68. The method of claim 66, wherein the second bone active-agent is administered conjointly with the polypeptide.

69. The method of claims 66, wherein the polypeptide and the second bone active-agent are administered as a single co-formulation.

70. The method of claim 66, wherein the polypeptide and the second bone active-agent are administered simultaneously.

71. The method of claim 66, wherein the polypeptide and the second bone active-agent are administered at separate times.

72. The method of claim 65, wherein the polypeptide includes one or more modified amino acid residues selected from a glycosylated amino acid, a PEGylated amino acid, a farnesylated amino acid, an acetylated amino acid, a biotinylated amino acid, or an amino acid conjugated to a lipid moiety.

73. The method of claim 65, wherein the polypeptide is administered no more frequently than once per month.

74. The method of claim 65, wherein the polypeptide is administered no more frequently than once every three months.

75. The method of claim 65, wherein the polypeptide is administered no more frequently than once every six months.

76. The method of claim 65, wherein the polypeptide is at least 98% pure as determined by size-exclusion chromatography.

77. The method of claim 65, wherein the polypeptide comprises an amino acid sequence that is at least 97% identical to SEQ ID NO: 2.

78. The method of claim 65, wherein the polypeptide comprises an amino acid sequence that is at least 99% identical to SEQ ID NO: 2.

79. The method of claim 65, wherein the polypeptide comprises the amino acid sequence of SEQ ID NO: 2.

80. The method of claim 65, wherein the polypeptide is glycosylated and has a glycosylation pattern identical to a glycosylation pattern obtained by expressing the polypeptide in a Chinese hamster ovary (CHO) cell line.

81. The method of claim 65, wherein the N-terminus of the polypeptide is ILGRSETQE (SEQ ID NO: 11).

82. The method of claim 65, wherein the polypeptide further comprises a domain that enhances one or more of in vivo stability, in vivo half-life, uptake/administration, tissue localization or distribution, or formation of protein complexes.

83. The method of claim 82, wherein the domain is an immunoglobulin Fc domain.

84. The method of claim 82, wherein the domain is serum albumin.

85. The method of claim 65, wherein the serum half-life of the polypeptide is greater than two weeks.

86. The method of claim 65, wherein the serum half-life of the polypeptide is 20-30 days.

87. The method of claim 65, wherein the polypeptide has one or more of the following characteristics: (i) binds to an ActRIIa ligand with a $K_D$ of at least $10^{-7}$ M; and (ii) inhibits ActRIIa signaling.

88. The method of claim 65, wherein the polypeptide is soluble.

89. The method of claim 65, wherein the polypeptide binds to activin.

90. The method of claim 65, wherein the polypeptide is an antagonist of activin A.

91. The method of claim 65, wherein the polypeptide comprises an amino acid sequence that is at least 95% identical to SEQ ID NO: 7.

92. The method of claim 65, wherein the polypeptide comprises an amino acid sequence that is at least 97% identical to SEQ ID NO: 7.

93. The method of claim 65, wherein the polypeptide comprises an amino acid sequence that is at least 99% identical to SEQ ID NO: 7.

94. The method of claim 65, wherein the polypeptide comprises the amino acid sequence of SEQ ID NO: 7.

95. The method of claim 65, wherein the polypeptide is recombinantly expressed using a Tissue Plasminogen Activator (TPA) leader sequence.

96. The method of claim 95, wherein the TPA leader sequence comprises the amino acid sequence of SEQ ID NO:9.

97. A method for treating a bone-related disorder, comprising administering to a subject in need thereof an effective amount of a polypeptide comprising an amino acid sequence that is at least 95% identical to SEQ ID NO: 2, wherein the bone-related disorder is associated with low bone density or decreased bone strength.

98. The method of claim 97, wherein the bone-related disorder is selected from osteoporosis, hypogonadal bone loss, tumor-induced bone loss, cancer therapy-induced bone loss, bony metastases, hyperparathyroidism, Cushing's disease, thyrotoxicosis, chronic diarrheal state or malabsorption, renal tubular acidosis, anorexia nervosa, and Paget's disease.

99. The method of claim 97, further comprising administering a second bone active-agent.

100. The method of claim 99, wherein the bone active-agent is selected from a bisphosphonate, an estrogen, a selective estrogen receptor modulator, a parathyroid hormone, a calcitonin, a calcium supplement, and a vitamin D supplement.

101. The method of claim 99, wherein the second bone active-agent is administered conjointly with the polypeptide.

102. The method of claims 99, wherein the polypeptide and the second bone active-agent are administered as a single co-formulation.

103. The method of claim 99, wherein the polypeptide and the second bone active-agent are administered simultaneously.

104. The method of claim 99, wherein the polypeptide and the second bone active-agent are administered at separate times.

105. The method of claim 97, wherein the polypeptide includes one or more modified amino acid residues selected from a glycosylated amino acid, a PEGylated amino acid, a farnesylated amino acid, an acetylated amino acid, a biotinylated amino acid, or an amino acid conjugated to a lipid moiety.

106. The method of claim 97, wherein the polypeptide is administered no more frequently than once per month.

107. The method of claim 97, wherein the polypeptide is administered no more frequently than once every three months.

108. The method of claim 97, wherein the polypeptide is administered no more frequently than once every six months.

109. The method of claim 97, wherein the polypeptide is at least 98% pure as determined by size-exclusion chromatography.

110. The method of claim 97, wherein the polypeptide comprises an amino acid sequence that is at least 97% identical to SEQ ID NO: 2.

111. The method of claim 97, wherein the polypeptide comprises an amino acid sequence that is at least 99% identical to SEQ ID NO: 2.

112. The method of claim 97, wherein the polypeptide comprises the amino acid sequence of SEQ ID NO: 2.

113. The method of claim 97, wherein the polypeptide is glycosylated and has a glycosylation pattern identical to a glycosylation pattern obtained by expressing the polypeptide in a Chinese hamster ovary (CHO) cell line.

114. The method of claim 97, wherein the N-terminus of the polypeptide is ILGRSETQE (SEQ ID NO: 11).

115. The method of claim 97, wherein the polypeptide further comprises a domain that enhances one or more of in vivo stability, in vivo half-life, uptake/administration, tissue localization or distribution, or formation of protein complexes.

116. The method of claim 115, wherein the domain is an immunoglobulin Fc domain.

117. The method of claim 115, wherein the domain is serum albumin.

118. The method of claim 97, wherein the serum half-life of the polypeptide is greater than two weeks.

119. The method of claim 97, wherein the serum half-life of the polypeptide is 20-30 days.

120. The method of claim 97, wherein the polypeptide has one or more of the following characteristics: (i) binds to an ActRIIa ligand with a $K_D$ of at least $10^{-7}$ M; and (ii) inhibits ActRIIa signaling.

121. The method of claim 97, wherein the polypeptide is soluble.

122. The method of claim 97, wherein the polypeptide binds to activin.

123. The method of claim 97, wherein the polypeptide is an antagonist of activin A.

124. The method of claim 97, wherein the polypeptide comprises an amino acid sequence that is at least 95% identical to SEQ ID NO: 7.

125. The method of claim 97, wherein the polypeptide comprises an amino acid sequence that is at least 97% identical to SEQ ID NO: 7.

126. The method of claim 97, wherein the polypeptide comprises an amino acid sequence that is at least 99% identical to SEQ ID NO: 7.

127. The method of claim 97, wherein the polypeptide comprises the amino acid sequence of SEQ ID NO: 7.

128. The method of claim 97, wherein the polypeptide is recombinantly expressed using a Tissue Plasminogen Activator (TPA) leader sequence.

129. The method of claim 128, wherein the TPA leader sequence comprises the amino acid sequence of SEQ ID NO:9.

* * * * *

SEQUENCE LISTING

```
<160> NUMBER OF SEQ ID NOS: 14

<210> SEQ ID NO 1
<211> LENGTH: 513
<212> TYPE: PRT
<213> ORGANISM: Homo sapiens

<400> SEQUENCE: 1

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160
```

Tyr Arg His His Lys Met Ala Tyr Pro Pro Val Leu Val Pro Thr Gln
            165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
            195                 200                 205

Ala Gln Leu Leu Asn Glu Tyr Val Ala Val Lys Ile Phe Pro Ile Gln
210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
            245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
            275                 280                 285

Leu Cys His Ile Ala Glu Thr Met Ala Arg Gly Leu Ala Tyr Leu His
            290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
            325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
            355                 360                 365

Glu Val Leu Glu Gly Ala Ile Asn Phe Gln Arg Asp Ala Phe Leu Arg
            370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
            405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
            435                 440                 445

Ala Gly Met Ala Met Leu Cys Glu Thr Ile Glu Glu Cys Trp Asp His
450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
            485                 490                 495

Val Val Thr Met Val Thr Asn Val Asp Phe Pro Pro Lys Glu Ser Ser
            500                 505                 510

Leu

<210> SEQ ID NO 2
<211> LENGTH: 115
<212> TYPE: PRT
<213> ORGANISM: Homo sapiens

<400> SEQUENCE: 2

Ile Leu Gly Arg Ser Glu Thr Gln Glu Cys Leu Phe Phe Asn Ala Asn
1               5                   10                  15

```
Trp Glu Lys Asp Arg Thr Asn Gln Thr Gly Val Glu Pro Cys Tyr Gly
         20                  25                  30

Asp Lys Asp Lys Arg Arg His Cys Phe Ala Thr Trp Lys Asn Ile Ser
             35                  40                  45

Gly Ser Ile Glu Ile Val Lys Gln Gly Cys Trp Leu Asp Asp Ile Asn
 50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
                100                 105                 110

Lys Pro Pro
        115

<210> SEQ ID NO 3
<211> LENGTH: 100
<212> TYPE: PRT
<213> ORGANISM: Homo sapiens

<400> SEQUENCE: 3

Ile Leu Gly Arg Ser Glu Thr Gln Glu Cys Leu Phe Phe Asn Ala Asn
 1               5                  10                  15

Trp Glu Lys Asp Arg Thr Asn Gln Thr Gly Val Glu Pro Cys Tyr Gly
         20                  25                  30

Asp Lys Asp Lys Arg Arg His Cys Phe Ala Thr Trp Lys Asn Ile Ser
             35                  40                  45

Gly Ser Ile Glu Ile Val Lys Gln Gly Cys Trp Leu Asp Asp Ile Asn
 50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met
            100

<210> SEQ ID NO 4
<211> LENGTH: 1542
<212> TYPE: DNA
<213> ORGANISM: Homo sapiens

<400> SEQUENCE: 4
atgggagctg ctgcaaagtt ggcgtttgcc gtctttctta tctcctgttc ttcaggtgct    60
atacttggta gatcagaaac tcaggagtgt cttttcttta tgctaattg ggaaaaagac    120 agaaccaatc aaactggtgt tgaaccgtgt tatggtgaca agataaacg gcggcattgt    180 tttgctacct ggaagaatat ttctggttcc attgaaatag tgaaacaagg ttgttggctg    240
gatgatatca actgctatga caggactgat tgtgtagaaa aaaagacag ccctgaagta    300 tattttgtt gctgtgaggg caatatgtgt aatgaaaagt tttcttattt tccagagatg    360
gaagtcacac agcccacttc aaatccagtt acacctaagc caccctatta caacatcctg    420
ctctattcct tggtgccact tatgttaatt gcgggattg tcatttgtgc attttgggtg    480
tacaggcatc acaagatggc ctaccctcct gtacttgttc aactcaaga cccaggacca    540 cccccacctt ctccattact agggttgaaa ccactgcagt tattagaagt gaaagcaagg    600
ggaagatttg gttgtgtctg gaaagcccag ttgcttaacg aatatgtggc tgtcaaaata    660
```

```
tttccaatac aggacaaaca gtcatggcaa aatgaatacg aagtctacag tttgcctgga      720
atgaagcatg agaacatatt acagttcatt ggtgcagaaa aacgaggcac cagtgttgat      780
gtggatcttt ggctgatcac agcatttcat gaaaagggtt cactatcaga ctttcttaag      840
gctaatgtgg tctcttggaa tgaactgtgt catattgcag aaaccatggc tagaggattg      900
gcatatttac atgaggatat acctggccta aaagatggcc acaaacctgc catatctcac      960
agggacatca aaagtaaaaa tgtgctgttg aaaaacaacc tgacagcttg cattgctgac     1020
tttgggttgg ccttaaaatt tgaggctggc aagtctgcag gcgataccca tggacaggtt     1080
ggtacccgga ggtacatggc tccagaggta ttagagggtg ctataaactt ccaaagggat     1140
gcatttttga ggatagatat gtatgccatg ggattagtcc tatgggaact ggcttctcgc     1200
tgtactgctg cagatggacc tgtagatgaa tacatgttgc catttgagga ggaaattggc     1260
cagcatccat ctcttgaaga catgcaggaa gttgttgtgc ataaaaaaaa gaggcctgtt     1320
ttaagagatt attggcagaa acatgctgga atggcaatgc tctgtgaaac cattgaagaa     1380
tgttgggatc acgacgcaga agccaggtta tcagctggat gtgtaggtga agaattacc     1440 cagatgcaga gactaacaaa tattattacc acagaggaca ttgtaacagt ggtcacaatg     1500
gtgacaaatg ttgactttcc tcccaaagaa tctagtctat ga                        1542

<210> SEQ ID NO 5
<211> LENGTH: 345
<212> TYPE: DNA
<213> ORGANISM: Homo sapiens

<400> SEQUENCE: 5
atacttggta gatcagaaac tcaggagtgt cttttcttta atgctaattg ggaaaaagac       60
agaaccaatc aaactggtgt tgaaccgtgt tatggtgaca aagataaacg gcggcattgt      120
tttgctacct ggaagaatat ttctggttcc attgaaatag tgaaacaagg ttgttggctg      180
gatgatatca actgctatga caggactgat tgtgtagaaa aaaagacag ccctgaagta      240 tattttttgtt gctgtgaggg caatatgtgt aatgaaaagt tttccttattt tccagagatg      300 gaagtcacac agcccacttc aaatccagtt acacctaagc caccc                      345

<210> SEQ ID NO 6
<211> LENGTH: 225
<212> TYPE: PRT
<213> ORGANISM: Homo sapiens
<220> FEATURE:
<221> NAME/KEY: VARIANT
<222> LOCATION: 43
<223> OTHER INFORMATION: Xaa can represent either Asp or Ala
<220> FEATURE:
<221> NAME/KEY: VARIANT
<222> LOCATION: 100
<223> OTHER INFORMATION: Xaa can represent either Lys or Ala
<220> FEATURE:
<221> NAME/KEY: VARIANT
<222> LOCATION: 212
<223> OTHER INFORMATION: Xaa can represent either Asn or Ala

<400> SEQUENCE: 6

Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Xaa Val Ser His Glu Asp
         35                  40                  45

Pro Glu Val Lys Phe Asn Trp Tyr Val Asp Gly Val Glu Val His Asn
```

```
            50                  55                  60
Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Xaa Val Ser Asn Lys Ala Leu Pro Val Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Xaa His Tyr Thr Gln Lys Ser Leu Ser Leu Ser Pro Gly
210                 215                 220

Lys
225

<210> SEQ ID NO 7
<211> LENGTH: 344
<212> TYPE: PRT
<213> ORGANISM: Homo sapiens

<400> SEQUENCE: 7

Ile Leu Gly Arg Ser Glu Thr Gln Glu Cys Leu Phe Phe Asn Ala Asn
 1               5                  10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
 50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met Glu Val Thr Gln Pro Thr Ser Asn Pro Val Thr Pro
                100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
```

```
                195                 200                 205
Asp Trp Leu Asn Gly Lys Glu Tyr Lys Cys Lys Val Ser Asn Lys Ala
210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
                275                 280                 285

Lys Thr Thr Pro Pro Val Leu Asp Ser Asp Gly Ser Phe Phe Leu Tyr
                290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
                340

<210> SEQ ID NO 8
<211> LENGTH: 21
<212> TYPE: PRT
<213> ORGANISM: Apis mellifera

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Homo sapiens

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 20
<212> TYPE: PRT
<213> ORGANISM: Homo sapiens

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Homo sapiens

<400> SEQUENCE: 11

Ile Leu Gly Arg Ser Glu Thr Gln Glu
1               5
```

<210> SEQ ID NO 12
<211> LENGTH: 329
<212> TYPE: PRT
<213> ORGANISM: Homo sapiens

<400> SEQUENCE: 12

```
Ile Leu Gly Arg Ser Glu Thr Gln Glu Cys Leu Phe Phe Asn Ala Asn
  1               5                  10                  15

Trp Glu Lys Asp Arg Thr Asn Gln Thr Gly Val Glu Pro Cys Tyr Gly
             20                  25                  30

Asp Lys Asp Lys Arg Arg His Cys Phe Ala Thr Trp Lys Asn Ile Ser
         35                  40                  45

Gly Ser Ile Glu Ile Val Lys Gln Gly Cys Trp Leu Asp Asp Ile Asn
     50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 13
<211> LENGTH: 369
<212> TYPE: PRT
<213> ORGANISM: Homo sapiens

<400> SEQUENCE: 13

```
Met Asp Ala Met Lys Arg Gly Leu Cys Cys Val Leu Leu Leu Cys Gly
  1               5                  10                  15

Ala Val Phe Val Ser Pro Gly Ala Ala Ile Leu Gly Arg Ser Glu Thr
             20                  25                  30

Gln Glu Cys Leu Phe Phe Asn Ala Asn Trp Glu Lys Asp Arg Thr Asn
             35                  40                  45

Gln Thr Gly Val Glu Pro Cys Tyr Gly Asp Lys Asp Lys Arg Arg His
         50                  55                  60

Cys Phe Ala Thr Trp Lys Asn Ile Ser Gly Ser Ile Glu Ile Val Lys
 65                  70                  75                  80

Gln Gly Cys Trp Leu Asp Asp Ile Asn Cys Tyr Asp Arg Thr Asp Cys
                 85                  90                  95

Val Glu Lys Lys Asp Ser Pro Glu Val Tyr Phe Cys Cys Cys Glu Gly
             100                 105                 110

Asn Met Cys Asn Glu Lys Phe Ser Tyr Phe Pro Glu Met Glu Val Thr
             115                 120                 125

Gln Pro Thr Ser Asn Pro Val Thr Pro Lys Pro Pro Thr Gly Gly Gly
             130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                 165                 170                 175

Arg Thr Pro Glu Val Thr Cys Val Val Val Asp Val Ser His Glu Asp
             180                 185                 190

Pro Glu Val Lys Phe Asn Trp Tyr Val Asp Gly Val Glu Val His Asn
             195                 200                 205

Ala Lys Thr Lys Pro Arg Glu Glu Gln Tyr Asn Ser Thr Tyr Arg Val
         210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                 245                 250                 255

Thr Ile Ser Lys Ala Lys Gly Gln Pro Arg Glu Pro Gln Val Tyr Thr
             260                 265                 270

Leu Pro Pro Ser Arg Glu Glu Met Thr Lys Asn Gln Val Ser Leu Thr
             275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                 325                 330                 335

Ser Arg Trp Gln Gln Gly Asn Val Phe Ser Cys Ser Val Met His Glu
             340                 345                 350

Ala Leu His Asn His Tyr Thr Gln Lys Ser Leu Ser Leu Ser Pro Gly
             355                 360                 365

Lys

<210> SEQ ID NO 14
<211> LENGTH: 1114
<212> TYPE: DNA
<213> ORGANISM: Homo sapiens

<400> SEQUENCE: 14
```

-continued

| | | | | | |
|---|---|---|---|---|---|
| atggatgcaa | tgaagagagg | gctctgctgt | gtgctgctgc | tgtgtggagc | agtcttcgtt | 60 |
| tcgcccggcg | ccgctatact | tggtagatca | gaaactcagg | agtgtctttt | tttaatgcta | 120 |
| attgggaaaa | agacagaacc | aatcaaactg | gtgttgaacc | gtgttatggt | gacaaagata | 180 |
| aacggcggca | ttgttttgct | acctggaaga | atatttctgg | ttccattgaa | tagtgaaaca | 240 |
| aggttgttgg | ctggatgata | tcaactgcta | tgacaggact | gattgtgtag | aaaaaaaaga | 300 |
| cagccctgaa | gtatatttct | gttgctgtga | gggcaatatg | tgtaatgaaa | agttttctta | 360 |
| ttttccggag | atggaagtca | cacagcccac | ttcaaatcca | gttacaccta | agccacccac | 420 |
| cggtggtgga | actcacacat | gcccaccgtg | cccagcacct | gaactcctgg | ggggaccgtc | 480 |
| agtcttcctc | ttccccccaa | aacccaagga | caccctcatg | atctcccgga | ccctgaggt | 540 |
| cacatgcgtg | gtggtggacg | tgagccacga | agaccctgag | gtcaagttca | actggtacgt | 600 |
| ggacggcgtg | gaggtgcata | atgccaagac | aaagccgcgg | gaggagcagt | acaacagcac | 660 |
| gtaccgtgtg | gtcagcgtcc | tcaccgtcct | gcaccaggac | tggctgaatg | gcaaggagta | 720 |
| caagtgcaag | gtctccaaca | aagccctccc | agtccccatc | gagaaaacca | tctccaaagc | 780 |
| caaagggcag | ccccgagaac | cacaggtgta | caccctgccc | ccatcccggg | aggagatgac | 840 |
| caagaaccag | gtcagcctga | cctgcctggt | caaaggcttc | tatcccagcg | acatcgccgt | 900 |
| ggagtgggag | agcaatgggc | agccggagaa | caactacaag | accacgcctc | ccgtgctgga | 960 |
| ctccgacggc | tccttcttcc | tctatagcaa | gctcaccgtg | gacaagagca | ggtggcagca | 1020 |
| ggggaacgtc | ttctcatgct | ccgtgatgca | tgaggctctg | cacaaccact | acacgcagaa | 1080 |
| gagcctctcc | ctgtctccgg | gtaaatgaga | attc | | | 1114 |